United States Patent
Catalano et al.

(10) Patent No.: US 10,787,442 B2
(45) Date of Patent: Sep. 29, 2020

(54) MODULATORS OF INDOLEAMINE 2,3-DIOXYGENASE

(71) Applicant: GLAXOSMITHKLINE INTELLECTUAL PROPERTY DEVELOPMENT LIMITED, Brentford, Middlesex (GB)

(72) Inventors: John G. Catalano, Research Triangle Park, NC (US); Martha Alicia De La Rosa, Research Triangle Park, NC (US); Wieslaw Mieczyslaw Kazmierski, Research Triangle Park, NC (US); Vicente Samano, Research Triangle Park, NC (US)

(73) Assignee: GLAXOSMITHKLINE INTELLECTUAL PROPERTY DEVELOPMENT LIMITED, Brentford, Middlesex (GB)

( * ) Notice: Subject to any disclaimer, the term of this patent is extended or adjusted under 35 U.S.C. 154(b) by 0 days.

(21) Appl. No.: 16/464,795

(22) PCT Filed: Dec. 15, 2017

(86) PCT No.: PCT/IB2017/058015
§ 371 (c)(1),
(2) Date: May 29, 2019

(87) PCT Pub. No.: WO2018/116108
PCT Pub. Date: Jun. 28, 2018

(65) Prior Publication Data
US 2019/0322652 A1    Oct. 24, 2019

Related U.S. Application Data

(60) Provisional application No. 62/436,659, filed on Dec. 20, 2016.

(51) Int. Cl.
*C07D 405/14*    (2006.01)
*C07D 401/12*    (2006.01)
*C07D 417/12*    (2006.01)
*C07D 417/14*    (2006.01)

(52) U.S. Cl.
CPC ......... *C07D 405/14* (2013.01); *C07D 401/12* (2013.01); *C07D 417/12* (2013.01); *C07D 417/14* (2013.01)

(58) Field of Classification Search
CPC .................................................. C07D 405/14
USPC .......................................................... 514/333
See application file for complete search history.

(56) References Cited

U.S. PATENT DOCUMENTS

2016/0289171 A1    10/2016 Balog

FOREIGN PATENT DOCUMENTS

WO    WO 2017/139414 A1    8/2017

*Primary Examiner* — Taofiq A Solola
(74) *Attorney, Agent, or Firm* — Robert H. Brink; Duke M. Fitch; Edward R. Gimmi

(57) ABSTRACT

Provided are IDO inhibitor compounds of Formula I and pharmaceutically acceptable salts thereof, their pharmaceutical compositions, their methods of preparation, and methods for their use in the prevention and/or treatment of diseases.

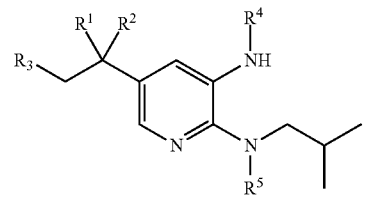

2 Claims, 2 Drawing Sheets

MODULATORS OF INDOLEAMINE 2,3-DIOXYGENASE

This application is a § 371 of International Application No. PCT/IB2017/058015, filed 15 Dec. 2017, which claims the benefit of U.S. Provisional Application No. 62/436,659, filed Dec. 2016.

FIELD OF THE INVENTION

Compounds, methods and pharmaceutical compositions for the prevention and/or treatment of HIV; including the prevention of the progression of AIDS and general immunosuppression, by administering certain indoleamine 2,3-dioxygenase compounds in therapeutically effective amounts are disclosed. Methods for preparing such compounds and methods of using the compounds and pharmaceutical compositions thereof are also disclosed.

BACKGROUND OF THE INVENTION

Indoleamine-2,3-dioxygenase 1 (IDO1) is a heme-containing enzyme that catalyzes the oxidation of the indole ring of tryptophan to produce N-formyl kynurenine, which is rapidly and constitutively converted to kynurenine (Kyn) and a series of downstream metabolites. IDO1 is the rate limiting step of this kynurenine pathway of tryptophan metabolism and expression of IDO1 is inducible in the context of inflammation. Stimuli that induce IDO1 include viral or bacterial products, or inflammatory cytokines associated with infection, tumors, or sterile tissue damage. Kyn and several downstream metabolites are immunosuppressive: Kyn is antiproliferative and proapoptotic to T cells and NK cells (Munn, Shafizadeh et al. 1999, Frumento, Rotondo et al. 2002) while metabolites such as 3-hydroxy anthranilic acid (3-HAA) or the 3-HAA oxidative dimerization product cinnabarinic acid (CA) inhibit phagocyte function (Sekkai, Guittet et al. 1997), and induce the differentiation of immunosuppressive regulatory T cells (Treg) while inhibiting the differentiation of gut-protective IL-17 or IL-22-producing CD4+ T cells (Th17 and Th22) (Favre, Mold et al. 2010). IDO1 induction, among other mechanisms, is likely important in limiting immunopathology during active immune responses, in promoting the resolution of immune responses, and in promoting fetal tolerance. However in chronic settings, such as cancer, or chronic viral or bacterial infection, IDO1 activity prevents clearance of tumor or pathogen and if activity is systemic, IDO1 activity may result in systemic immune dysfunction (Boasso and Shearer 2008, Li, Huang et al. 2012). In addition to these immunomodulatory effects, metabolites of IDO1 such as Kyn and quinolinic acid are also known to be neurotoxic and are observed to be elevated in several conditions of neurological dysfunction and depression. As such, IDO1 is a therapeutic target for inhibition in a broad array of indications, such as to promote tumor clearance, enable clearance of intractable viral or bacterial infections, decrease systemic immune dysfunction manifest as persistent inflammation during HIV infection or immunosuppression during sepsis, and prevent or reverse neurological conditions.

IDO1 and Persistent Inflammation in HIV Infection:

Despite the success of antiretroviral therapy (ART) in suppressing HIV replication and decreasing the incidence of AIDS-related conditions, HIV-infected patients on ART have a higher incidence of non-AIDS morbidities and mortality than their uninfected peers. These non-AIDS conditions include cancer, cardiovascular disease, osteoporosis, liver disease, kidney disease, frailty, and neurocognitive dysfunction (Deeks 2011). Several studies indicate that non-AIDS morbidity/mortality is associated with persistent inflammation, which remains elevated in HIV-infected patients on ART as compared to peers (Deeks 2011). As such, it is hypothesized that persistent inflammation and immune dysfunction despite virologic suppression with ART is a cause of these non-AIDS-defining events (NA-DEs).

HIV infects and kills CD4+ T cells, with particular preference for cells like those CD4+ T cells that reside in the lymphoid tissues of the mucosal surfaces (Mattapallil, Douek et al. 2005). The loss of these cells combined with the inflammatory response to infection result in a perturbed relationship between the host and all pathogens, including HIV itself, but extending to pre-existing or acquired viral infections, fungal infections, and resident bacteria in the skin and mucosal surfaces. This dysfunctional host:pathogen relationship results in the over-reaction of the host to what would typically be minor problems as well as permitting the outgrowth of pathogens among the microbiota. The dysfunctional host:pathogen interaction therefore results in increased inflammation, which in turn leads to deeper dysfunction, driving a vicious cycle. As inflammation is thought to drive non-AIDS morbidity/mortality, the mechanisms governing the altered host:pathogen interaction are therapeutic targets.

IDO1 expression and activity are increased during untreated and treated HIV infection as well as in primate models of SIV infection (Boasso, Vaccari et al. 2007, Favre, Lederer et al. 2009, Byakwaga, Boum et al. 2014, Hunt, Sinclair et al. 2014, Tenorio, Zheng et al. 2014). IDO1 activity, as indicated by the ratio of plasma levels of enzyme substrate and product (Kyn/Tryp or K:T ratio), is associated with other markers of inflammation and is one of the strongest predictors of non-AIDS morbidity/mortality (Byakwaga, Boum et al. 2014, Hunt, Sinclair et al. 2014, Tenorio, Zheng et al. 2014). In addition, features consistent with the expected impact of increased IDO1 activity on the immune system are major features of HIV and SIV induced immune dysfunction, such as decreased T cell proliferative response to antigen and imbalance of Treg:Th17 in systemic and intestinal compartments (Favre, Lederer et al. 2009, Favre, Mold et al. 2010). As such, we and others hypothesize that IDO1 plays a role in driving the vicious cycle of immune dysfunction and inflammation associated with non-AIDS morbidity/mortality. Thus, we propose that inhibiting IDO1 will reduce inflammation and decrease the risk of NADEs in ART-suppressed HIV-infected persons.

IDO1 and Persistent Inflammation Beyond HIV

As described above, inflammation associated with treated chronic HIV infection is a likely driver of multiple end organ diseases [Deeks 2011]. However, these end organ diseases are not unique to HIV infection and are in fact the common diseases of aging that occur at earlier ages in the HIV-infected population. In the uninfected general population inflammation of unknown etiology is a major correlate of morbidity and mortality [Pinti, 2016 #88]. Indeed many of the markers of inflammation are shared, such as IL-6 and CRP. If, as hypothesized above, IDO1 contributes to persistent inflammation in the HIV-infected population by inducing immune dysfunction in the GI tract or systemic tissues, then IDO1 may also contribute to inflammation and therefore end organ diseases in the broader population. These inflammation associated end organ diseases are exemplified by cardiovascular diseases, metabolic syndrome, liver disease (NAFLD, NASH), kidney disease, osteoporosis, and neurocognitive impairment. Indeed, the IDO1 pathway has links in the literature to liver disease (Vivoli abstracts at Italian Assoc. for the Study of the Liver Conference 2015], diabetes [Baban, 2010 #89], chronic kidney disease [Schefold, 2009 #90], cardiovascular disease [Mangge, 2014 #92; Mangge, 2014 #91], as well as general aging and all cause mortality [Pertovaara, 2006 #93]. As such, inhibition of IDO1 may have application in decreasing inflammation in the general population to decrease the incidence of specific end organ diseases associated with inflammation and aging.

IDO1 and Oncology

IDO expression can be detected in a number of human cancers (for example; melanoma, pancreatic, ovarian, AML, CRC, prostate and endometrial) and correlates with poor prognosis (Munn 2011). Multiple immunosuppressive roles have been ascribed to the action of IDO, including the induction of Treg differentiation and hyper-activation, suppression of Teff immune response, and decreased DC function, all of which impair immune recognition and promote tumor growth (Munn 2011). IDO expression in human brain tumors is correlated with reduced survival. Orthotropic and transgenic glioma mouse models demonstrate a correlation between reduced IDO expression and reduced Treg infiltration and a increased long term survival (Wainwright, Balyasnikova et al. 2012). In human melanoma a high proportion of tumors (33 of 36 cases) displayed elevated IDO suggesting an important role in establishing an immunosuppressive tumor microenvironment (TME) characterized by the expansion, activation and recruitment of MDSCs in a Treg-dependent manner (Holmgaard, Zamarin et al. 2015). Additionally, host IDO expressing immune cells have been identified in the draining lymph nodes and in the tumors themselves (Mellor and Munn 2004). Hence, both tumor and host-derived IDO are believed to contribute to the immune suppressed state of the TME.

The inhibition of IDO was one of the first small molecule drug strategies proposed for re-establishment of an immunogenic response to cancer (Mellor and Munn 2004). The d-enantiomer of 1-methyl tryptophan (D-1MTor indoximod) was the first IDO inhibitor to enter clinical trials. While this compound clearly does inhibit the activity of IDO, it is a very weak inhibitor of the isolated enzyme and the in vivo mechanism(s) of action for this compound are still being elucidated. Investigators at Incyte optimized a hit compound obtained from a screening process into a potent and selective inhibitor with sufficient oral exposure to demonstrate a delay in tumor growth in a mouse melanoma model (Yue, Douty et al. 2009). Further development of this series led to INCB204360 which is a highly selective for inhibition of IDO-1 over IDO-2 and TDO in cell lines transiently transfected with either human or mouse enzymes (Liu, Shin et al. 2010). Similar potency was seen for cell lines and primary human tumors which endogenously express IDO1 (IC50s~3-20 nM). When tested in co-culture of DCs and naïve CD4$^+$CD25$^-$ T cells, INCB204360 blocked the conversion of these T cells into CD4$^+$FoxP3$^+$ Tregs. Finally, when tested in a syngeneic model (PAN02 pancreatic cells) in immunocompetent mice, orally dosed INCB204360 provided a significant dose-dependent inhibition of tumor growth, but was without effect against the same tumor implanted in immune-deficient mice. Additional studies by the same investigators have shown a correlation of the inhibition of IDO1 with the suppression of systemic kynurenine levels and inhibition of tumor growth in an additional syngeneic tumor model in immunocompetent mice. Based upon these preclinical studies, INCB24360 entered clinical trials for the treatment of metastatic melanoma (Beatty, O'Dwyer et al. 2013).

In light of the importance of the catabolism of tryptophan in the maintenance of immune suppression, it is not surprising that overexpression of a second tryptophan metabolizing enzyme, TDO2, by multiple solid tumors (for example, bladder and liver carcinomas, melanomas) has also been detected. A survey of 104 human cell lines revealed 20/104 with TDO expression, 17/104 with IDO1 and 16/104 expressing both (Pilotte, Larrieu et al. 2012). Similar to the inhibition of IDO1, the selective inhibition of TDO2 is effective in reversing immune resistance in tumors overexpressing TDO2 (Pilotte, Larrieu et al. 2012). These results support TDO2 inhibition and/or dual TDO2/IDO1 inhibition as a viable therapeutic strategy to improve immune function.

Multiple pre-clinical studies have demonstrated significant, even synergistic, value in combining IDO-1 inhibitors in combination with T cell checkpoint modulating mAbs to CTLA-4, PD-1, and GITR. In each case, both efficacy and related PD aspects of improved immune activity/function were observed in these studies across a variety of murine models (Balachandran, Cavnar et al. 2011, Holmgaard, Zamarin et al. 2013, M. Mautino 2014, Wainwright, Chang et al. 2014). The Incyte IDO1 inhibitor (INCB204360, epacadostat) has been clinically tested in combination with a CTLA4 blocker (ipilimumab), but it is unclear that an effective dose was achieved due to dose-limited adverse events seen with the combination. In contrast recently released data for an on-going trial combining epacadostat with Merck's PD-1 mAb (pembrolizumab) demonstrated improved tolerability of the combination allowing for higher doses of the IDO1 inhibitor. There have been several clinical responses across various tumor types which is encouraging. However, it is not yet known if this combination is an improvement over the single agent activity of pembrolizumab (Gangadhar, Hamid et al. 2015). Similarly, Roche/Genentech are advancing NGL919/GDC-0919 in combination with both mAbs for PD-L1 (MPDL3280A, Atezo) and OX-40 following the recent completion of a phase 1a safety and PK/PD study in patients with advanced tumors.

IDO1 and Chronic Infections

IDO1 activity generates kynurenine pathway metabolites such as Kyn and 3-HAA that impair at least T cell, NK cell, and macrophage activity (Munn, Shafizadeh et al. 1999, Frumento, Rotondo et al. 2002) (Sekkai, Guittet et al. 1997, Favre, Mold et al. 2010). Kyn levels or the Kyn/Tryp ratio are elevated in the setting of chronic HIV infection (Byakwaga, Boum et al. 2014, Hunt, Sinclair et al. 2014, Tenorio, Zheng et al. 2014), HBV infection (Chen, Li et al. 2009), HCV infection (Larrea, Riezu-Boj et al. 2007, Asghar, Ashiq et al. 2015), and TB infection (Suzuki, Suda et al. 2012) and are associated with antigen-specific T cell dysfunction (Boasso, Herbeuval et al. 2007, Boasso, Hardy et al. 2008, Loughman and Hunstad 2012, Ito, Ando et al. 2014, Lepiller, Soulier et al. 2015). As such, it is thought that in these cases of chronic infection, IDO1-mediated inhibition of the pathogen-specific T cell response plays a role in the persistence of infection, and that inhibition of IDO1 may have a benefit in promoting clearance and resolution of infection.

IDO1 and Sepsis

IDO1 expression and activity are observed to be elevated during sepsis and the degree of Kyn or Kyn/Tryp elevation corresponded to increased disease severity, including mortality (Tattevin, Monnier et al. 2010, Darcy, Davis et al. 2011). In animal models, blockade of IDO1 or IDO1 genetic knockouts protected mice from lethal doses of LPS or from mortality in the cecal ligation/puncture model (Jung, Lee et al. 2009, Hoshi, Osawa et al. 2014). Sepsis is characterized by an immunosuppressive phase in severe cases (Hotchkiss, Monneret et al. 2013), potentially indicating a role for IDO1 as a mediator of immune dysfunction, and indicating that pharmacologic inhibition of IDO1 may provide a clinical benefit in sepsis.

IDO1 and Neurological Disorders

In addition to immunologic settings, IDO1 activity is also linked to disease in neurological settings (reviewed in Lovelace Neuropharmacology 2016 (Lovelace, Varney et al. 2016)). Kynurenine pathway metabolites such as 3-hydroxykynurenine and quinolinic acid are neurotoxic, but are balanced by alternative metabolites kynurenic acid or picolinic acid, which are neuroprotective. Neurodegenerative and psychiatric disorders in which kynurenine pathway metabolites have been demonstrated to be associated with disease include multiple sclerosis, motor neuron disorders such as amyotrophic lateral sclerosis, Huntington's disease, Parkinson's disease, Alzheimer's disease, major depressive disorder, schizophrenia, anorexia (Lovelace, Varney et al. 2016). Animal models of neurological disease have shown some impact of weak IDO1 inhibitors such as 1-methyltryptophan on disease, indicating that IDO1 inhibition may provide clinical benefit in prevention or treatment of neurological and psychiatric disorders.

It would therefore be an advance in the art to discover IDO inhibitors that effective the balance of the aforementioned properties as a disease modifying therapy in chronic HIV infections to decrease the incidence of non-AIDS morbidity/mortality; and/or a disease modifying therapy to prevent mortality in sepsis; and/or an immunotherapy to enhance the immune response to HIV, HBV, HCV and other chronic viral infections, chronic bacterial infections, chronic fungal infections, and to tumors; and/or for the treatment of depression or other neurological/neuropsychiatric disorders.

Asghar, K., M. T. Ashiq, B. Zulfiqar, A. Mahroo, K. Nasir and S. Murad (2015). "Indoleamine 2,3-dioxygenase expression and activity in patients with hepatitis C virus-induced liver cirrhosis." *Exp Ther Med* 9(3): 901-904.

Balachandran, V. P., M. J. Cavnar, S. Zeng, Z. M. Bamboat, L. M. Ocuin, H. Obaid, E. C. Sorenson, R. Popow, C. Ariyan, F. Rossi, P. Besmer, T. Guo, C. R. Antonescu, T. Taguchi, J. Yuan, J. D. Wolchok, J. P. Allison and R. P. Dematteo (2011). "Imatinib potentiates antitumor T cell responses in gastrointestinal stromal tumor through the inhibition of Ido." *Nature Medicine* 17(9): 1094-1100.

Beatty, G. L., P. J. O'Dwyer, J. Clark, J. G. Shi, R. C. Newton, R. Schaub, J. Maleski, L. Leopold and T. Gajewski (2013). "Phase I study of the safety, pharmacokinetics (PK), and pharmacodynamics (PD) of the oral inhibitor of indoleamine 2,3-dioxygenase (IDO1) INCB024360 in patients (pts) with advanced malignancies." *ASCO Meeting Abstracts* 31(15_suppl): 3025.

Boasso, A., A. W. Hardy, S. A. Anderson, M. J. Dolan and G. M. Shearer (2008). "HIV-induced type I interferon and tryptophan catabolism drive T cell dysfunction despite phenotypic activation." *PLoS One* 3(8): e2961.

Boasso, A., J. P. Herbeuval, A. W. Hardy, S. A. Anderson, M. J. Dolan, D. Fuchs and G. M. Shearer (2007). "HIV inhibits CD4+ T-cell proliferation by inducing indoleamine 2,3-dioxygenase in plasmacytoid dendritic cells." *Blood* 109(8): 3351-3359.

Boasso, A. and G. M. Shearer (2008). "Chronic innate immune activation as a cause of HIV-1 immunopathogenesis." *Clin Immunol* 126(3): 235-242.

Boasso, A., M. Vaccari, A. Hryniewicz, D. Fuchs, J. Nacsa, V. Cecchinato, J. Andersson, G. Franchini, G. M. Shearer and C. Chougnet (2007). "Regulatory T-cell markers, indoleamine 2,3-dioxygenase, and virus levels in spleen and gut during progressive simian immunodeficiency virus infection." *J Virol* 81(21): 11593-11603.

Byakwaga, H., Y. Boum, 2nd, Y. Huang, C. Muzoora, A. Kembabazi, S. D. Weiser, J. Bennett, H. Cao, J. E. Haberer, S. G. Deeks, D. R. Bangsberg, J. M. McCune, J. N. Martin and P. W. Hunt (2014). "The kynurenine pathway of tryptophan catabolism, CD4+ T-cell recovery, and mortality among HIV-infected Ugandans initiating antiretroviral therapy." *J Infect Dis* 210(3): 383-391.

Chen, Y. B., S. D. Li, Y. P. He, X. J. Shi, Y. Chen and J. P. Gong (2009). "Immunosuppressive effect of IDO on T cells in patients with chronic hepatitis B*." *Hepatol Res* 39(5): 463-468.

Darcy, C. J., J. S. Davis, T. Woodberry, Y. R. McNeil, D. P. Stephens, T. W. Yeo and N. M. Anstey (2011). "An observational cohort study of the kynurenine to tryptophan ratio in sepsis: association with impaired immune and microvascular function." *PLoS One* 6(6): e21185.

Deeks, S. G. (2011). "HIV infection, inflammation, immunosenescence, and aging." *Annu Rev Med* 62: 141-155.

Favre, D., S. Lederer, B. Kanwar, Z. M. Ma, S. Proll, Z. Kasakow, J. Mold, L. Swainson, J. D. Barbour, C. R. Baskin, R. Palermo, I. Pandrea, C. J. Miller, M. G. Katze and J. M. McCune (2009). "Critical loss of the balance between Th17 and T regulatory cell populations in pathogenic SIV infection." *PLoS Pathog* 5(2): e1000295.

Favre, D., J. Mold, P. W. Hunt, B. Kanwar, P. Loke, L. Seu, J. D. Barbour, M. M. Lowe, A. Jayawardene, F. Aweeka, Y. Huang, D. C. Douek, J. M. Brenchley, J. N. Martin, F. M. Hecht, S. G. Deeks and J. M. McCune (2010). "Tryptophan catabolism by indoleamine 2,3-dioxygenase 1 alters the balance of TH17 to regulatory T cells in HIV disease." *Sci Transl Med* 2(32): 32ra36.

Frumento, G., R. Rotondo, M. Tonetti, G. Damonte, U. Benatti and G. B. Ferrara (2002). "Tryptophan-derived catabolites are responsible for inhibition of T and natural killer cell proliferation induced by indoleamine 2,3-dioxygenase." *J Exp Med* 196(4): 459-468.

Gangadhar, T., O. Hamid, D. Smith, T. Bauer, J. Wasser, J. Luke, A. Balmanoukian, D. Kaufman, Y. Zhao, J. Maleski, L. Leopold and T. Gajewski (2015). "Preliminary results from a Phase I/II study of epacadostat (incb024360) in combination with pembrolizumab in patients with selected advanced cancers." *Journal for ImmunoTherapy of Cancer* 3(Suppl 2): O7.

Holmgaard, R. B., D. Zamarin, Y. Li, B. Gasmi, D. H. Munn, J. P. Allison, T. Merghoub and J. D. Wolchok (2015). "Tumor-Expressed IDO Recruits and Activates MDSCs in a Treg-Dependent Manner." *Cell Reports* 13(2): 412-424.

Holmgaard, R. B., D. Zamarin, D. H. Munn, J. D. Wolchok and J. P. Allison (2013). "Indoleamine 2,3-dioxygenase is a critical resistance mechanism in antitumor T cell immunotherapy targeting CTLA-4." *Journal of Experimental Medicine* 210(7): 1389-1402.

Hoshi, M., Y. Osawa, H. Ito, H. Ohtaki, T. Ando, M. Takamatsu, A. Hara, K. Saito and M. Seishima (2014). "Blockade of indoleamine 2,3-dioxygenase reduces mortality from peritonitis and sepsis in mice by regulating functions of CD11b+ peritoneal cells." *Infect Immun* 82(11): 4487-4495.

Hotchkiss, R. S., G. Monneret and D. Payen (2013). "Sepsis-induced immunosuppression: from cellular dysfunctions to immunotherapy." *Nat Rev Immunol* 13(12): 862-874.

Hunt, P. W., E. Sinclair, B. Rodriguez, C. Shive, B. Clagett, N. Funderburg, J. Robinson, Y. Huang, L. Epling, J. N. Martin, S. G. Deeks, C. L. Meinert, M. L. Van Natta, D. A. Jabs and M. M. Lederman (2014). "Gut epithelial barrier dysfunction and innate immune activation predict mortality in treated HIV infection." *J Infect Dis* 210(8): 1228-1238.

Ito, H., T. Ando, K. Ando, T. Ishikawa, K. Saito, H. Moriwaki and M. Seishima (2014). "Induction of hepatitis B virus surface antigen-specific cytotoxic T lymphocytes can be up-regulated by the inhibition of indoleamine 2, 3-dioxygenase activity." *Immunology* 142(4): 614-623.

Jung, I. D., M. G. Lee, J. H. Chang, J. S. Lee, Y. I. Jeong, C. M. Lee, W. S. Park, J. Han, S. K. Seo, S. Y. Lee and Y. M. Park (2009). "Blockade of indoleamine 2,3-dioxygenase protects mice against lipopolysaccharide-induced endotoxin shock." *J Immunol* 182(5): 3146-3154.

Larrea, E., J. I. Riezu-Boj, L. Gil-Guerrero, N. Casares, R. Aldabe, P. Sarobe, M. P. Civeira, J. L. Heeney, C. Rollier, B. Verstrepen, T. Wakita, F. Borras-Cuesta, J. J. Lasarte and J. Prieto (2007). "Upregulation of indoleamine 2,3-dioxygenase in hepatitis C virus infection." *J Virol* 81(7): 3662-3666.

Lepiller, Q., E. Soulier, Q. Li, M. Lambotin, J. Barths, D. Fuchs, F. Stoll-Keller, T. J. Liang and H. Barth (2015). "Antiviral and Immunoregulatory Effects of Indoleamine-2,3-Dioxygenase in Hepatitis C Virus Infection." *J Innate Immun* 7(5): 530-544.

Li, L., L. Huang, H. P. Lemos, M. Mautino and A. L. Mellor (2012). "Altered tryptophan metabolism as a paradigm for good and bad aspects of immune privilege in chronic inflammatory diseases." *Front Immunol* 3: 109.

Liu, X., N. Shin, H. K. Koblish, G. Yang, Q. Wang, K. Wang, L. Leffet, M. J. Hansbury, B. Thomas, M. Rupar, P. Waeltz, K. J. Bowman, P. Polam, R. B. Sparks, E. W. Yue, Y. Li, R. Wynn, J. S. Fridman, T. C. Burn, A. P. Combs, R. C. Newton and P. A. Scherle (2010). "Selective inhibition of IDO1 effectively regulates mediators of antitumor immunity." *Blood* 115(17): 3520-3530.

Loughman, J. A. and D. A. Hunstad (2012). "Induction of indoleamine 2,3-dioxygenase by uropathogenic bacteria attenuates innate responses to epithelial infection." *J Infect Dis* 205(12): 1830-1839.

Lovelace, M. D., B. Varney, G. Sundaram, M. J. Lennon, C. K. Lim, K. Jacobs, G. J. Guillemin and B. J. Brew (2016). "Recent evidence for an expanded role of the kynurenine pathway of tryptophan metabolism in neurological diseases." *Neuropharmacology*.

M. Mautino, C. J. L., N. Vahanian, J. Adams, C. Van Allen, M. D. Sharma, T. S. Johnson and D. H. Munn (2014). "Synergistic antitumor effects of combinatorial immune checkpoint inhibition with anti-PD-1/PD-L antibodies and the IDO pathway inhibitors NLG919 and indoximod in the context of active immunotherapy." April 2014 AACR Meeting Poster #5023.

Mattapallil, J. J., D. C. Douek, B. Hill, Y. Nishimura, M. Martin and M. Roederer (2005). "Massive infection and loss of memory CD4+ T cells in multiple tissues during acute SIV infection." *Nature* 434(7037): 1093-1097.

Mellor, A. L. and D. H. Munn (2004). "IDO expression by dendritic cells: Tolerance and tryptophan catabolism." *Nature Reviews Immunology* 4(10): 762-774.

Munn, D. H. (2011). "Indoleamine 2,3-dioxygenase, Tregs and cancer." *Current Medicinal Chemistry* 18(15): 2240-2246.

Munn, D. H., E. Shafizadeh, J. T. Attwood, I. Bondarev, A. Pashine and A. L. Mellor (1999). "Inhibition of T cell proliferation by macrophage tryptophan catabolism." *J Exp Med* 189(9): 1363-1372.

Pilotte, L., P. Larrieu, V. Stroobant, D. Colau, E. Dolušić, R. Frédérick, E. De Plaen, C. Uyttenhove, J. Wouters, B. Masereel and B. J. Van Den Eynde (2012). "Reversal of tumoral immune resistance by inhibition of tryptophan 2,3-dioxygenase." *Proceedings of the National Academy of Sciences of the United States of America* 109(7): 2497-2502.

Sekkai, D., O. Guittet, G. Lemaire, J. P. Tenu and M. Lepoivre (1997). "Inhibition of nitric oxide synthase expression and activity in macrophages by 3-hydroxyanthranilic acid, a tryptophan metabolite." *Arch Biochem Biophys* 340(1): 117-123.

Suzuki, Y., T. Suda, K. Asada, S. Miwa, M. Suzuki, M. Fujie, K. Furuhashi, Y. Nakamura, N. Inui, T. Shirai, H. Hayakawa, H. Nakamura and K. Chida (2012). "Serum indoleamine 2,3-dioxygenase activity predicts prognosis of pulmonary tuberculosis." *Clin Vaccine Immunol* 19(3): 436-442.

Tattevin, P., D. Monnier, O. Tribut, J. Dulong, N. Bescher, F. Mourcin, F. Uhel, Y. Le Tulzo and K. Tarte (2010). "Enhanced indoleamine 2,3-dioxygenase activity in patients with severe sepsis and septic shock." *J Infect Dis* 201(6): 956-966.

Tenorio, A. R., Y. Zheng, R. J. Bosch, S. Krishnan, B. Rodriguez, P. W. Hunt, J. Plants, A. Seth, C. C. Wilson, S. G. Deeks, M. M. Lederman and A. L. Landay (2014). "Soluble markers of inflammation and coagulation but not T-cell activation predict non-AIDS-defining morbid events during suppressive antiretroviral treatment." *J Infect Dis* 210(8): 1248-1259.

Wainwright, D. A., I. V. Balyasnikova, A. L. Chang, A. U. Ahmed, K.-S. Moon, B. Auffinger, A. L. Tobias, Y. Han and M. S. Lesniak (2012). "IDO Expression in Brain Tumors Increases the Recruitment of Regulatory T Cells and Negatively Impacts Survival." *Clinical Cancer Research* 18(22): 6110-6121.

Wainwright, D. A., A. L. Chang, M. Dey, I. V. Balyasnikova, C. K. Kim, A. Tobias, Y. Cheng, J. W. Kim, J. Qiao, L. Zhang, Y. Han and M. S. Lesniak (2014). "Durable therapeutic efficacy utilizing combinatorial blockade against IDO, CTLA-4, and PD-L1 in mice with brain tumors." *Clinical Cancer Research* 20(20): 5290-5301.

Yue, E. W., B. Douty, B. Wayland, M. Bower, X. Liu, L. Leffet, Q. Wang, K. J. Bowman, M. J. Hansbury, C. Liu, M. Wei, Y. Li, R. Wynn, T. C. Burn, H. K. Koblish, J. S. Fridman, B. Metcalf, P. A. Scherle and A. P. Combs (2009). "Discovery of potent competitive inhibitors of indoleamine 2,3-dioxygenase with in vivo pharmacodynamic activity and efficacy in a mouse melanoma model." *Journal of Medicinal Chemistry* 52(23): 7364-7367.

SUMMARY OF THE INVENTION

Briefly, in one aspect, the present invention discloses compounds of Formula I

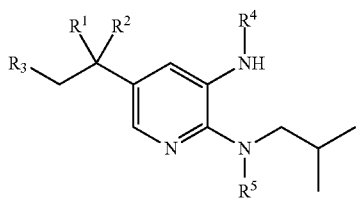

Formula I or a pharmaceutically acceptable salt thereof wherein:
$R^1$ and $R^2$ are independently H or $CH_3$, or $R^1$ and $R^2$ may join together with the carbon atom to which they are bonded to form a 3-6 membered cycloalkyl;
$R^3$ is $CO_2H$ or an acid isostere;
$R^4$ is a 4 to 6-membered heterocycle or heteroaryl containing 1 to 4 heteroatoms selected from N, S, and O, wherein said heterocycle or heteroaryl may optionally be substituted by 1 or 2 substituent selected from the group consisting of halogen, $C_{3-6}$cycloalkyl, $CH_2OH$, $C(O)NH_2$, CN, $CH_2OC_{1-3}$alkyl, $C_{1-3}$alkyl optionally substituted by 1-3 halogens, and wherein said $CH_2OH$ is optionally converted into a prodrug by converting the $CH_2OH$ group to a $CH_2OC(O)CH_3$, $CH_2OC(O)C(C_{1-4}alkyl)_3$, or $OP(O)(OH)_2$ group, or $OP(O)(OC_{1-4}alkyl)_2$ group;
$R^5$ is a 4, 5 or 6-membered cycloalkyl substituted with an OH or a $OCH_3$ group or 1 or 2 halogens, or a 5 or 6-membered heterocycle containing an O or a N and may optionally be substituted by a substituent selected from the group consisting of halogen, OH, $C_{1-4}$alkyl; $OC_{1-3}$alkyl, $C(O)C_{3-6}$cycloalkyl, $C(O)C_{1-3}$alkyl-O—$C_{1-3}$alkyl; $C(O)C_{1-3}$alkyl; $C(O)$—O—$C_{1-3}$alkyl, and a 4 to 6-membered heterocycle or heteroaryl containing 1 to 4 heteroatoms selected from N, S, and O, wherein said heterocycle or heteroaryl may optionally be substituted by 1 substituent selected from the group consisting of halogen, $C_{3-6}$cycloalkyl, $CH_2OH$, $C(O)NH_2$, CN, $CH_2OC_{1-3}$alkyl, $C_{1-3}$alkyl optionally substituted by 1-3 halogens.

In another aspect, the present invention discloses a method for treating diseases or conditions that would benefit from inhibition of IDO.

In another aspect, the present invention discloses pharmaceutical compositions comprising a compound of Formula I or a pharmaceutically acceptable salt thereof.

In another aspect, the present invention provides a compound of Formula I or a pharmaceutically acceptable salt thereof for use in therapy.

In another aspect, the present invention provides a compound of Formula I or a pharmaceutically acceptable salt thereof for use in treating diseases or condition that would benefit from inhibition of IDO.

In another aspect, the present invention provides a compound of Formula I or a pharmaceutically acceptable salt thereof for use in the manufacture of a medicament for use in treating diseases or conditions that would benefit from inhibition of IDO.

In another aspect, the present invention discloses a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

DETAILED DESCRIPTION OF REPRESENTATIVE EMBODIMENTS

Figure 1:
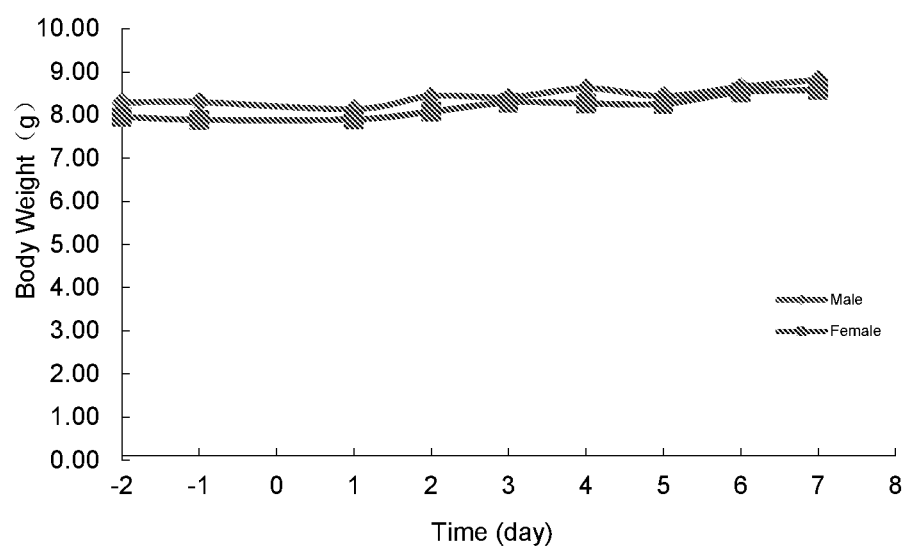
FIG. 1 is daily body weights of Beagle dogs during the study of example 6, 20 mg/kg PO BID dose.

Preferably one of $R^1$ and $R^2$ is H and the other is $CH_3$.
Preferably $R^3$ is $CO_2H$.
Preferably $R^4$ is a 5 or 6-membered heterocycle or heteroaryl containing 1 to 3 heteroatoms selected from N, and S. Most preferably $R^4$ is thiadiazole, pyrimidine, pyrazine, pyridazine, triazol, or thiazol.
Preferably $R^4$ is unsubstituted or substituted with 1 or 2 substituent selected from the group consisting of F, Cl, CN, $OCH_3$, $CF_3$, $C_{1-3}$alkyl, $C_{3-6}$cycloalkyl, $CONH_2$, $CH_2CH_2OCH_3$, and $CH_2OCH_3$.
Preferably $R^5$ is a 6-membered heterocycle containing an O or a N.
Preferably $R^5$ is unsubstituted or substituted on the heteroatom by a substituent selected from the group consisting of halogen, OH, $C_{1-4}$alkyl; $OC_{1-3}$alkyl, $C(O)C_{3-6}$cycloalkyl, $C(O)C_{1-3}$alkyl-O—$C_{1-3}$alkyl; $C(O)C_{1-3}$alkyl; $C(O)$—O—$C_{1-3}$alkyl, and a 4 to 6-membered heterocycle or heteroaryl containing 1 to 4 heteroatoms selected from N, S, and O, wherein said heterocycle or heteroaryl may optionally be substituted by 1 substituent selected from the group consisting of halogen, $C_{3-6}$cycloalkyl, $CH_2OH$, $C(O)NH_2$, CN, $CH_2OC_{1-3}$alkyl, $C_{1-3}$alkyl optionally substituted by 1-3 halogens. Most preferably, $R^5$ is unsubstituted or substituted on the heteroatom with OH or $OCH_3$.

Examples of suitable acid isosteres, includes for example

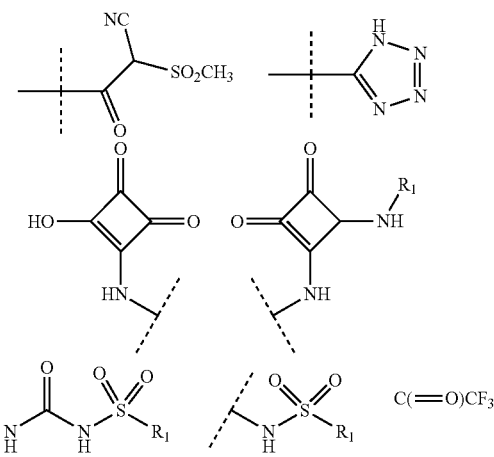

-continued

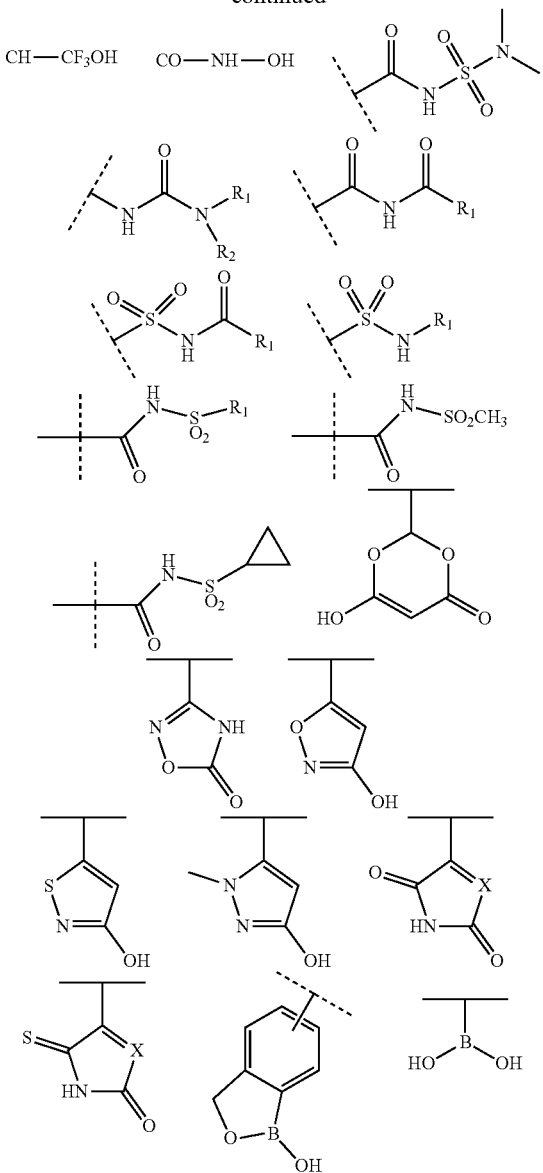

wherein $R^1$ and $R^2$ in the above list of isosters are independently $C_{1-6}$alkyl.

In particular, it is expected that the compounds and composition of this invention will be useful for prevention and/or treatment of HIV; including the prevention of the progression of AIDS and general immunosuppression. It is expected that in many cases such prevention and/or treatment will involve treating with the compounds of this invention in combination with at least one other drug thought to be useful for such prevention and/or treatment. For example, the IDO inhibitors of this invention may be used in combination with other immune therapies such as immune checkpoints (PD1, CTLA4, ICOS, etc.) and possibly in combination with growth factors or cytokine therapies (IL21, IL-7, etc.).

It is common practice in treatment of HIV to employ more than one effective agent. Therefore, in accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

It is also common practice in the oncology field to treat with more than one effective agent. Therefore, in accordance with another embodiment of the present invention, there is provided a method for preventing or treating cancer comprising administering to a human in need thereof a therapeutically effective amount of a compound of Formula I or a pharmaceutically acceptable salt thereof further comprising administration of at least one other agent effective tor preventing or treating cancer. Such agents include, for example, anti-neoplastic agents, chemotherapeutic agents, hormonal agents, and antibody agents.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or ACN are preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In another embodiment of the invention, there is provided a pharmaceutical composition comprising a pharmaceutically acceptable diluent and a therapeutically effective amount of a compound as defined in Formula I or a pharmaceutically acceptable salt thereof.

In one embodiment, the pharmaceutical formulation containing a compound of Formula I or a salt thereof is a formulation adapted for parenteral administration. In another embodiment, the formulation is a long-acting parenteral formulation. In a further embodiment, the formulation is a nano-particle formulation.

The present invention is directed to compounds, compositions and pharmaceutical compositions that have utility as novel treatments for immunosuppresion. While not wanting to be bound by any particular theory, it is thought that the present compounds are able to inhibit the enzyme that catalyzes the oxidative pyrrole ring cleavage reaction of I-Trp to N-formylkynurenine utilizing molecular oxygen or reactive oxygen species.

Therefore, in another embodiment of the present invention, there is provided a method for the prevention and/or treatment of HIV; including the prevention of the progression of AIDS and general immunosuppression.

EXAMPLES

The following examples serve to more fully describe the manner of making and using the above-described invention. It is understood that these examples in no way serve to limit the true scope of the invention, but rather are presented for illustrative purposes. In the examples and the synthetic schemes below, the following abbreviations have the following meanings. If an abbreviation is not defined, it has its generally accepted meaning.

ACN=acetonitrile
AIBN=azobisisobutyronitrile
aq.=aqueous
μL or uL=microliters
μM or uM=micromolar
NMR=nuclear magnetic resonance
boc=tert-butoxycarbonyl
br=broad
Cbz=Benzyloxycarbonyl
CDI=1,1'-carbonyldiimidazole
d=doublet
δ=chemical shift
° C.=degrees celcius
DCM=dichloromethane
dd=doublet of doublets
DHP=dihydropyran
DIAD=diisopropyl azodicarboxylate
DIEA or DIPEA=N,N-diisopropylethylamine
DMAP=4-(dimethylamino)pyridine
DMEM=Dulbeco's Modified Eagle's Medium
EtOAc=ethyl acetate
h or hr=hours
HATU=1-[Bis(dimethylamino)methylene]-1H-1,2,3-triazolo[4,5-b]pyridinium 3-oxid hexafluorophosphate
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
LCMS=liquid chromatography-mass spectrometry
m=multiplet
M=molar
$M+H^+$=parent mass spectrum peak plus $H^+$
MeOH=methanol
mg=milligram
min=minutes
mL=milliliter
mM=millimolar
mmol=millimole
MS=mass spectrum
MTBE=methyl tert-butyl ether
N=normal
NFK=N-formylkynurenine
NBS=N-bromosuccinimide
nm=nanomolar
PE=petroleum ether
ppm=parts per million
q.s.=sufficient amount
s=singlet
RT=room temperature
Rf=retardation factor
sat.=saturated
t=triplet
TEA=triethylamine
TFA=trifluoroacetic acid
TFAA=trifluoroacetic anhydride
THF=tetrahydrofuran
Equipment Description $^1$H NMR spectra were recorded on a Bruker Ascend 400 spectrometer or a Varian 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters ACQUITY UPLC with SQ Detectors using a Waters BEH C18, 2.1×50 mm, 1.7 μm using a gradient elution method.

Solvent A: 0.1% formic acid (FA) in water;
Solvent B: 0.1% FA in acetonitrile;
30% B for 0.5 min followed by 30-100% B over 2.5 min.

Example 1

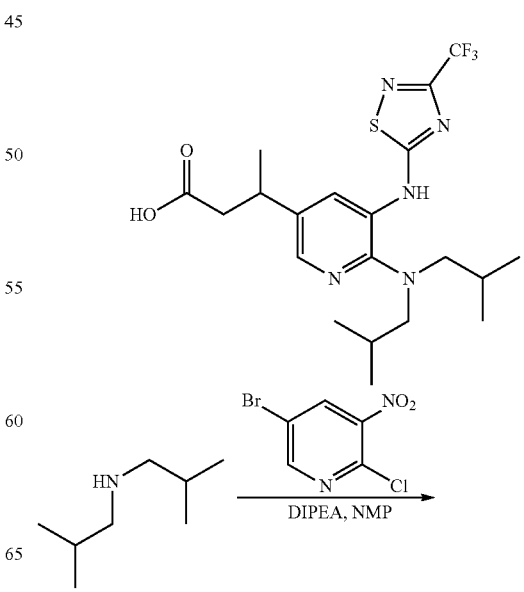

-continued

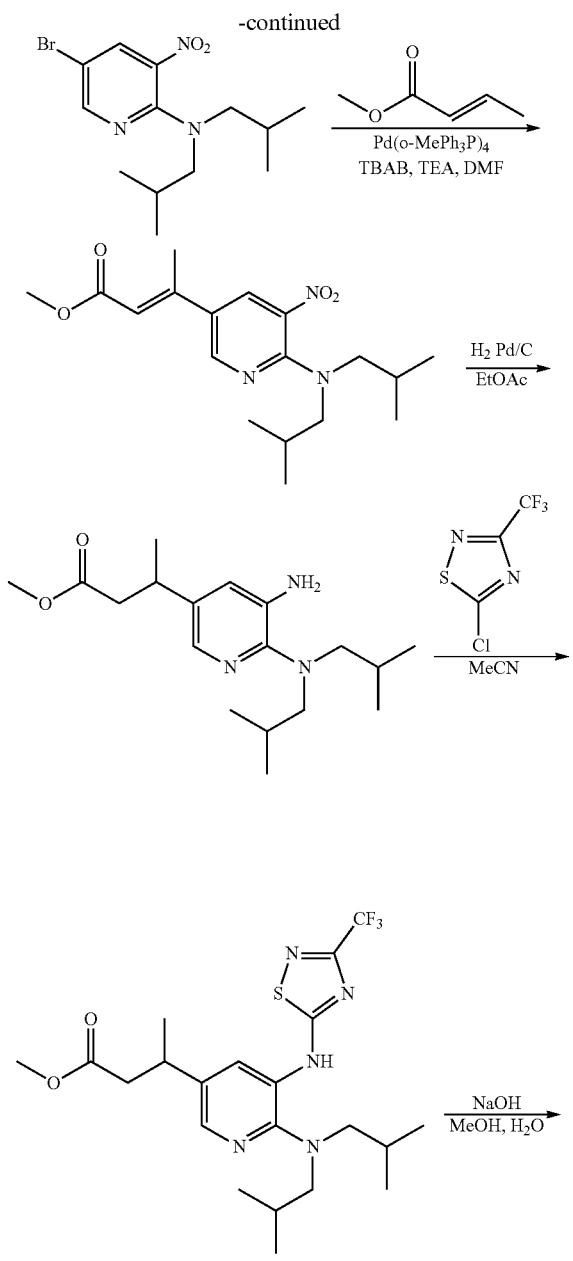

Preparation of 5-bromo-N,N-diisobutyl-3-nitropyridin-2-amine

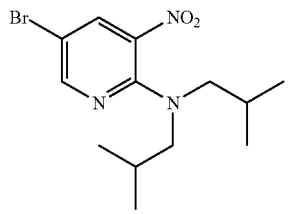 [SMILES: CC(C)CN(CC(C)C)c1ncc(Br)cc1[N+](=O)[O-]]

A mixture of 5-bromo-2-chloro-3-nitropyridine (5.0 g, 21.2 mmol), diisobutylamine (4.11 g, 31.8 mmol) in NMP (50 mL) was stirred at 140° C. for 8 hr. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (6.8 g, 97% yield). LCMS (ESI) m/z calcd for $C_{13}H_{20}BrN_3O_2$: 329.07. Found: 330.18/332.24 (M/M+2)$^+$.

Preparation of methyl (E)-3-(6-(diisobutylamino)-5-nitropyridin-3-yl)but-2-enoate

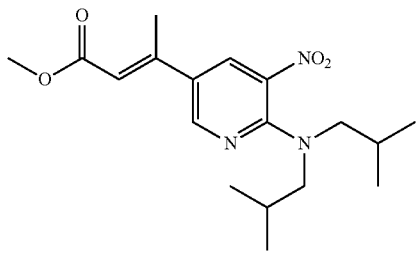 [SMILES: COC(=O)/C=C(\C)c1cnc(N(CC(C)C)CC(C)C)c([N+](=O)[O-])c1]

A mixture of 5-bromo-N,N-diisobutyl-3-nitropyridin-2-amine (6.8 g, 20.6 mmol), methyl (E)-but-2-enoate (6.3 g, 61.8 mmol), TBAB (1.35 g, 4.12 mmol), $Pd(o-MePh_3P)_4$ (825 mg, 1.05 mmol) and TEA (4.29 g, 41.2 mmol) in DMF (80 mL) was stirred at 100° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (5.5 g, 76% yield). LCMS (ESI) m/z calcd for $C_{18}H_{27}N_3O_4$: 349.20. Found: 350.26 (M+1)$^+$.

Preparation of methyl 3-(5-amino-6-(diisobutylamino)pyridin-3-yl)butanoate

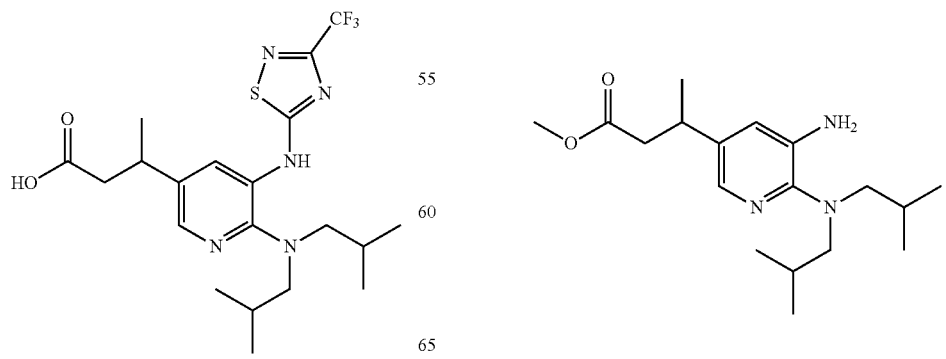

A mixture of methyl (E)-3-(6-(diisobutylamino)-5-nitropyridin-3-yl)but-2-enoate (1.0 g, 2.86 mmol) and 10% Pd/C (300 mg) in EtOAc (15 mL) was stirred at r.t. under H$_2$ atmosphere overnight. The resulting mixture was filtered through a pad of Celite and the filtrate was concentrated under reduced pressure to give the crude product which was purified by flash chromatography (silica gel, 0-50% EtOAc in PE) to afford the title compound (700 mg, 77% yield). LCMS (ESI) m/z calcd for C$_{18}$H$_{31}$N$_3$O$_2$: 321.24. Found: 322.50 (M+1)$^+$.

Preparation of methyl 3-(6-(diisobutylamino)-5-((3-(trifluoromethyl)-1,2,4-thiadia zol-5-yl)amino)pyridin-3-yl)butanoate

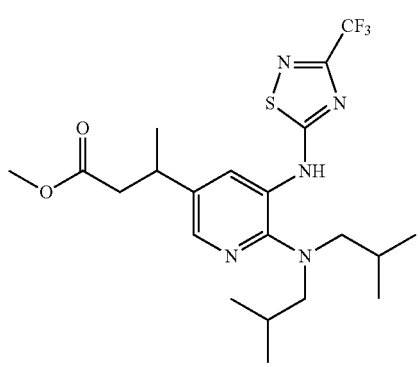 [SMILES: COC(=O)CC(C)c1cnc(N(CC(C)C)CC(C)C)c(Nc2nc(C(F)(F)F)ns2)c1]

A mixture of methyl 3-(5-amino-6-(diisobutylamino)pyridin-3-yl)butanoate (100 mg, 0.311 mmol) and 5-chloro-3-(trifluoromethyl)-1,2,4-thiadiazole (88 mg, 0.467 mmol) in MeCN (2 mL) was stirred at 95° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-50% EtOAc in PE) to afford the title compound (66 mg, 45% yield). LCMS (ESI) m/z calcd for C$_{21}$H$_{30}$F$_3$N$_5$O$_2$S: 473.21. Found: 472.11 (M-1)$^-$.

Preparation of 3-(6-(diisobutylamino)-5-((3-(trifluoromethyl)-1,2,4-thiadiazol-5-yl) amino)pyridin-3-yl) butanoic acid

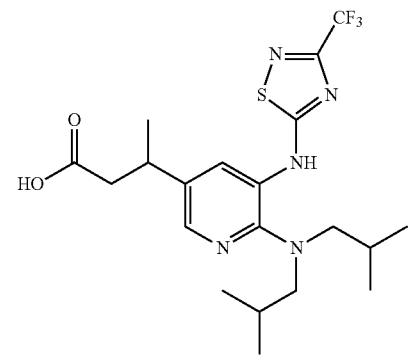 [SMILES: CC(C)CN(CC(C)C)c1ncc(C(C)CC(=O)O)cc1Nc1nc(C(F)(F)F)ns1]

To a solution of methyl 3-(6-(diisobutylamino)-5-((3-(trifluoromethyl)-1,2,4-thiadia zol-5-yl)amino)pyridin-3-yl) butanoate (66 mg, 0.14 mmol) in MeOH (3 mL) was added 4N NaOH aq. (0.5 mL). After stirred at r.t for 4 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (21.6 mg, 33% yield) as a white powder. $^1$H NMR (400 MHz, CDCl$_3$) δ 9.15 (br, 1H), 8.08 (d, J=2.1 Hz, 1H), 8.01 (d, J=1.9 Hz, 1H), 3.39-3.32 (m, 1H), 2.81 (d, J=7.2 Hz, 4H), 2.67 (d, J=7.0 Hz, 2H), 1.80-1.71 (m, 2H), 1.39 (d, J=7.0 Hz, 3H), 0.90 (d, J=6.6 Hz, 12H). LCMS (ESI) m/z calcd for C$_{20}$H$_{28}$F$_3$N$_5$O$_2$S: 459.19. Found: 460.24 (M+1)$^+$.

Example 2

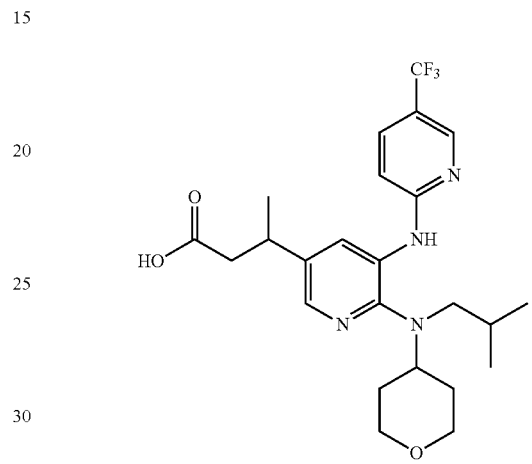

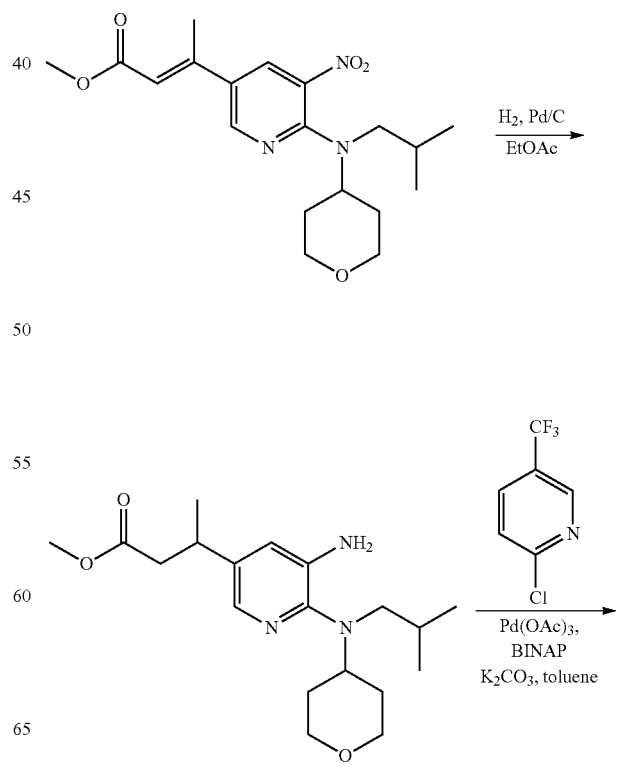

19

-continued

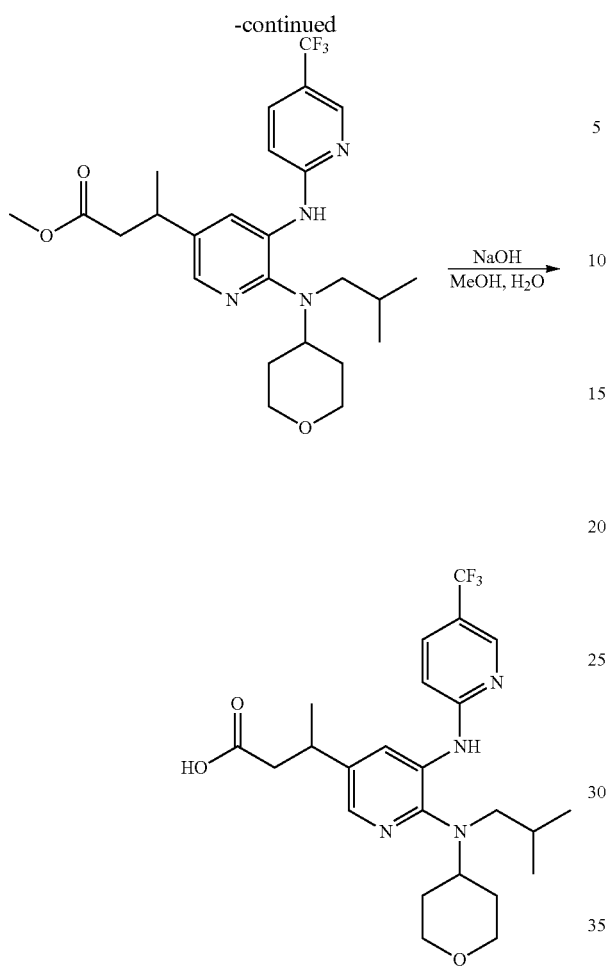

Preparation of methyl 3-(5-amino-6-(isobutyl(tetra-hydro-2H-pyran-4-yl)amino) pyridin-3-yl)butanoate A mixture of methyl (E)-3-(6-(isobutyl(tetrahydro-2H-pyran-4-yl)amino)-5-nitropyridin-3-yl)but-2-enoate (1.0 g, 2.65 mmol) and 10% Pd/C (300 mg) in EtOAc (15 mL) was stirred at r.t. under $H_2$ atmosphere overnight. The resulting mixture was filtered through a pad of Celite and the filtrate was concentrated under reduced pressure to give the crude product which was purified by flash chromatography (silica gel, 0-50% EtOAc in PE) to afford the title compound (900 mg, 98% yield). LCMS (ESI) m/z calcd for $C_{19}H_{31}N_3O_3$: 349.24. Found: 350.63 (M+1)$^+$.

20

Preparation of methyl 3-(6-(isobutyl(tetrahydro-2H-pyran-4-yl)amino)-5-((5-(tri fluoromethyl)pyridin-2-yl)amino)pyridin-3-yl)butanoate

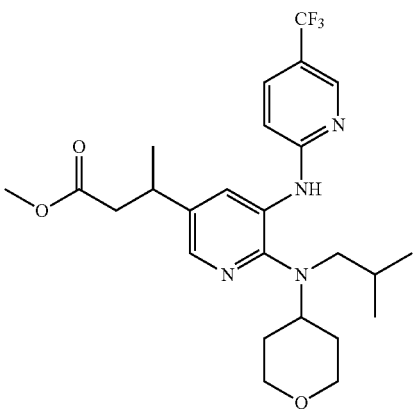 [SMILES: COC(=O)CC(C)c1cnc(N(CC(C)C)C2CCOCC2)c(Nc2ccc(C(F)(F)F)cn2)c1]

A mixture of methyl 3-(5-amino-6-(isobutyl(tetrahydro-2H-pyran-4-yl)amino)pyridin-3-yl)butanoate (50 mg, 0.143 mmol), 2-chloro-5-(trifluoromethyl)pyridine (51 mg, 0.286 mmol), Pd(OAc)$_2$ (1.3 mg, 0.00224 mmol), BINAP (1.6 mg, 0.00252 mmol) and $K_2CO_3$ (58 mg, 0.432 mmol) in toluene (2 mL) was stirred at 130° C. under $N_2$ atmosphere for 8 hr. The resulting mixture was partitioned between EtOAc and $H_2O$. The organic layer was washed with brine, dried over $Na_2SO_4$, filtered and concentrated to give the crude product which was purified by flash chromatography (silica gel, 0-50% EtOAc in PE) to afford the title compound (47 mg, 66% yield). LCMS (ESI) m/z calcd for $C_{25}H_{33}F_3N_4O_3$: 494.25. Found: 495.73 (M+1)$^+$.

Preparation of 3-(6-(isobutyl(tetrahydro-2H-pyran-4-yl)amino)-5-((5-(trifluoro methyl)pyridin-2-yl)amino)pyridin-3-yl)butanoic acid

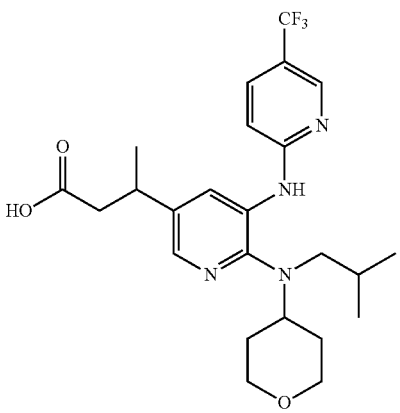 [SMILES: CC(C)CN(c1ncc(C(C)CC(=O)O)cc1Nc1ccc(C(F)(F)F)cn1)C1CCOCC1]

To a solution of methyl 3-(6-(isobutyl(tetrahydro-2H-pyran-4-yl)amino)-5-((5-(tri fluoromethyl)pyridin-2-yl)amino)pyridin-3-yl)butanoate (47 mg, 0.095 mmol) in MeOH (3 mL) was added 4N NaOH aq. (0.5 mL). After stirred at 50° C. for 3 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in H$_2$O with 0.1% formic acid) to afford the title compound (10.2 mg, 22% yield) as a white powder. $^1$H NMR (400 MHz, CDCl$_3$) δ 8.66 (d, J=2.2 Hz, 1H), 8.54 (s, 1H), 8.14 (s, 1H), 7.97 (d, J=2.2 Hz, 1H), 7.71 (dd, J=8.7, 2.3 Hz, 1H), 6.72 (d, J=8.7 Hz, 1H), 3.99-3.89 (m, 2H), 3.38-3.21 (m, 3H), 3.07-2.92 (m, 3H), 2.75-2.61 (m, 2H), 2.06-1.97 (m, 1H), 1.75-1.68 (m, 3H), 1.46-1.36 (m, 4H), 0.86 (d, J=6.6 Hz, 6H). LCMS (ESI) m/z calcd for C$_{24}$H$_{31}$F$_3$N$_4$O$_3$: 480.23. Found: 481.36 (M+1)$^+$.
Example 3
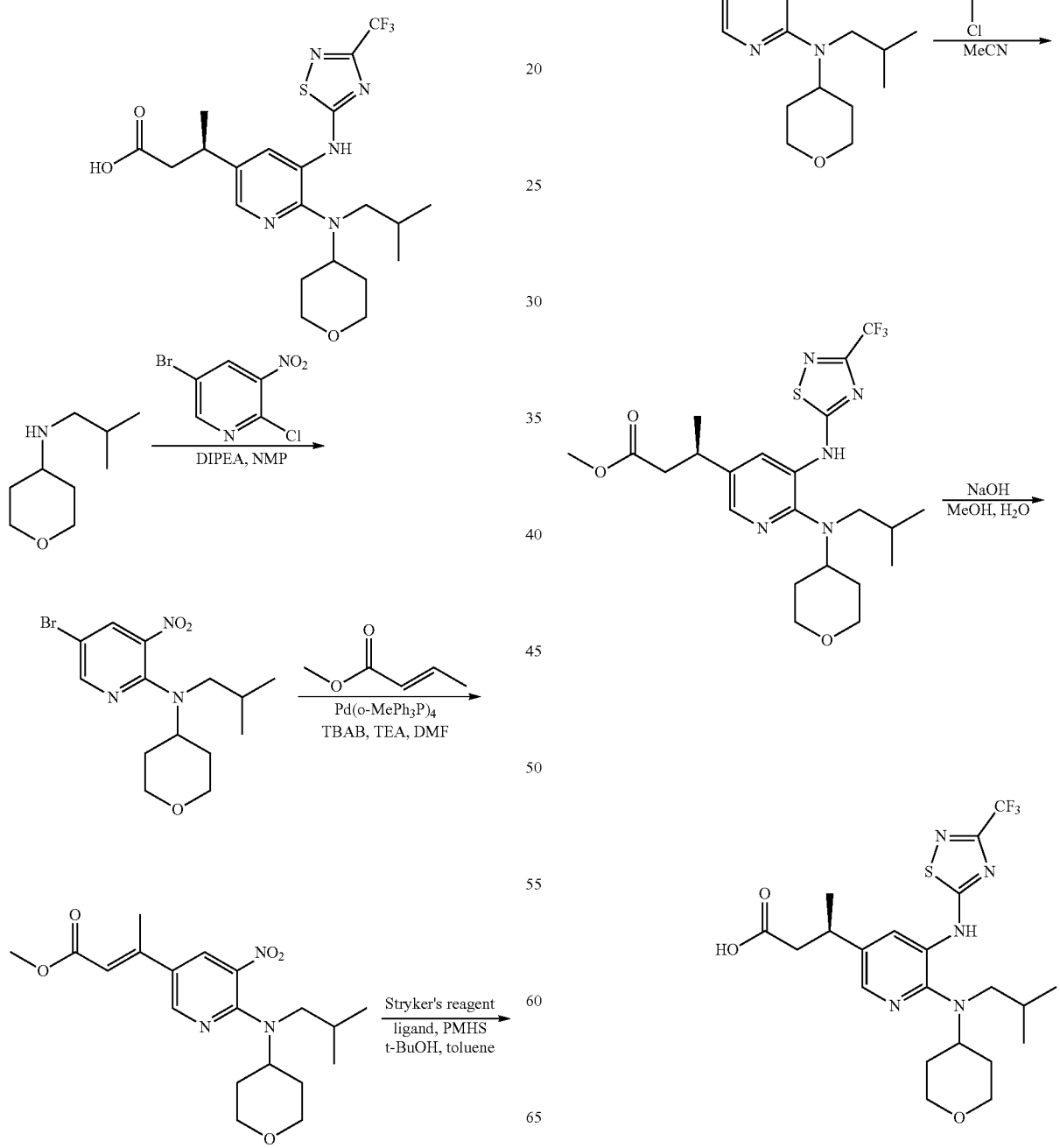

Preparation of 5-bromo-N-isobutyl-3-nitro-N-(tetrahydro-2H-pyran-4-yl)pyridin-2-amine

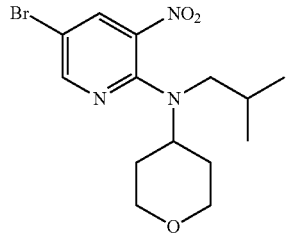 [SMILES: CC(C)CN(c1ncc(Br)cc1[N+](=O)[O-])C1CCOCC1]

A mixture of 5-bromo-2-chloro-3-nitropyridine (15.3 g, 64.5 mmol), N-isobutyltetra hydro-2H-pyran-4-amine (15.2 g, 96.7 mmol) and DIPEA (22.5 mL, 129 mmol) in NMP (150 mL) was stirred at 140° C. under $N_2$ atmosphere for 4 hr. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-10% EtOAc in PE) to afford the title compound (9.7 g, 42% yield) as a yellow solid. LCMS (ESI) m/z calcd for $C_{14}H_{20}BrN_3O_3$: 357.07. Found: 358.24/360.22 (M/M+2)+.

Preparation of methyl (E)-3-(6-(isobutyl(tetrahydro-2H-pyran-4-yl)amino)-5-nitro pyridin-3-yl)but-2-enoate

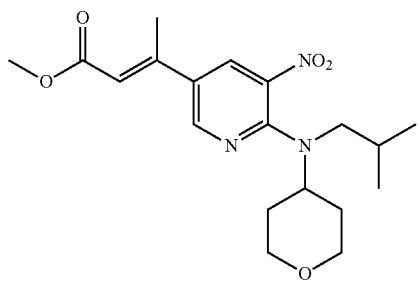 [SMILES: COC(=O)/C=C(\C)c1cnc(N(CC(C)C)C2CCOCC2)c([N+](=O)[O-])c1]

A mixture of 5-bromo-N-isobutyl-3-nitro-N-(tetrahydro-2H-pyran-4-yl)pyridin-2-amine (8.7 g, 24.2 mmol), methyl (E)-but-2-enoate (7.3 g, 72.7 mmol), TBAB (1.56 g, 4.85 mmol), Pd(o-MePh$_3$P)$_4$ (952 mg, 1.21 mmol) and TEA (4.94 g, 48.46 mmol) in DMF (90 mL) was stirred at 110° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-10% EtOAc in PE) to afford the title compound (4.42 g, 48% yield) as a yellow solid. LCMS (ESI) m/z calcd for $C_{19}H_{27}N_3O_5$: 377.20. Found: 378.52 (M+1)+.

Preparation of methyl (R)-3-(6-(isobutyl(tetrahydro-2H-pyran-4-yl)amino)-5-nitro pyridin-3-yl)butanoate

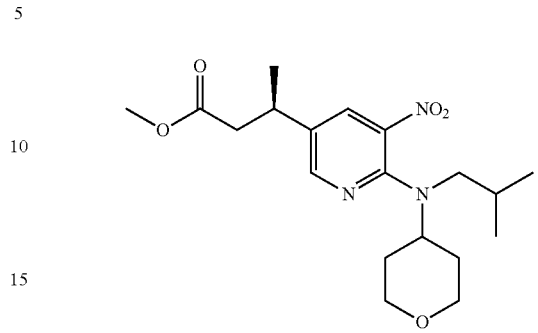

At −5° C., to a mixture of (CuHPh$_3$P)$_6$ (442 mg, 0.226 mmol) and (R,S)—PPF—P(tBu)$_2$ (443 mg, 0.819 mmol) in toluene (40 mL) was added PMHS (1.6 mL) and t-BuOH (1.34 mL) before the introduction of methyl (E)-3-(6-(isobutyl(tetrahydro-2H-pyran-4-yl) amino)-5-nitropyridin-3-yl) but-2-enoate (4.42 g, 11.7 mmol). After stirred at r.t. for 4 days, the resulting mixture was quenched with sat. NaHCO$_3$ aq. solution and extracted with EtOAc. The organic layer was washed with brine, dried over $Na_2SO_4$, filtered and concentrated to give the crude product which was purified by flash chromatography (silica gel, 0-20% EtOAc in PE) to afford the title compound (3.3 g, 74% yield) as a yellow oil. LCMS (ESI) m/z calcd for $C_{19}H_{29}N_3O_5$: 379.21. Found: 380.31 (M+1)+.

Preparation of methyl (R)-3-(5-amino-6-(isobutyl (tetrahydro-2H-pyran-4-yl) amino)pyridin-3-yl)butanoate

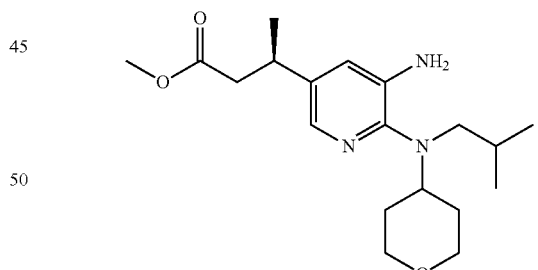

A mixture of methyl (R)-3-(6-(isobutyl(tetrahydro-2H-pyran-4-yl)amino)-5-nitro pyridin-3-yl)butanoate (3.3 g, 8.69 mmol) and 10% Pd/C (1.0 g) in EtOAc (30 mL) was stirred at 50° C. under $H_2$ atmosphere overnight. The resulting mixture was filtered through a pad of Celite and the filtrate was concentrated under reduced pressure to give the crude product which was purified by flash chromatography (silica gel, 0-50% EtOAc in PE) to afford the title compound (1.98 g, 65% yield) as a brown solid. LCMS (ESI) m/z calcd for $C_{19}H_{31}N_3O_3$: 349.24. Found: 350.93 (M+1)+.

Preparation of methyl (R)-3-(6-(isobutyl(tetrahydro-2H-pyran-4-yl)amino)-5-((3-(trifluoromethyl)-1,2,4-thiadiazol-5-yl)amino)pyridin-3-yl)butanoate

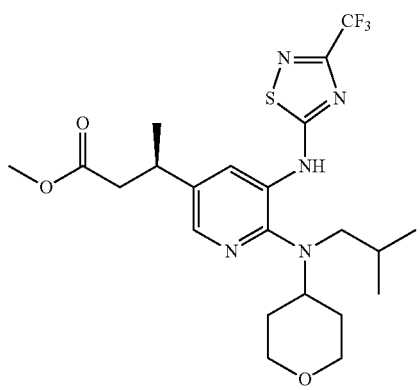 [SMILES: COC(=O)C[C@@H](C)c1cnc(N(CC(C)C)C2CCOCC2)c(Nc2nc(C(F)(F)F)ns2)c1]

A mixture of methyl (R)-3-(5-amino-6-(isobutyl(tetrahydro-2H-pyran-4-yl)amino)pyridin-3-yl)butanoate (100 mg, 0.282 mmol) and 5-chloro-3-(trifluoromethyl)-1,2,4-thiadiazole (81 mg, 0.43 mmol) in MeCN (3 mL) was stirred at 90° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (54 mg, 37% yield). LCMS (ESI) m/z calcd for C$_{22}$H$_{30}$F$_3$N$_5$O$_3$S: 501.20. Found: 502.19 (M+1)$^+$.

Preparation of (R)-3-(6-(isobutyl(tetrahydro-2H-pyran-4-yl)amino)-5-((3-(trifluoro methyl)-1,2,4-thiadiazol-5-yl)amino) pyridin-3-yl)butanoic acid

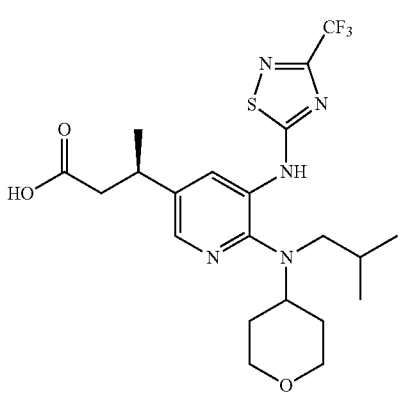 [SMILES: CC(C)CN(c1ncc([C@H](C)CC(=O)O)cc1Nc1nc(C(F)(F)F)ns1)C1CCOCC1]

To a solution of methyl (R)-3-(6-(isobutyl(tetrahydro-2H-pyran-4-yl)amino)-5-((3-(trifluoromethyl)-1,2,4-thiadiazol-5-yl)amino)pyridin-3-yl)butanoate (54 mg, 0.108 mmol) in MeOH (3 mL) was added 4N NaOH aq. (0.5 mL). After stirred at r.t for 5 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (29 mg, 55% yield) as a white powder. $^1$H NMR (400 MHz, CD3OD) δ 8.61 (d, J=2.0 Hz, 1H), 8.07 (d, J=2.2 Hz, 1H), 3.97-3.89 (m, 2H), 3.41-3.32 (m, 4H), 3.08 (d, J=7.0 Hz, 2H), 2.69-2.59 (m, 2H), 1.80-1.66 (m, 4H), 1.57-1.47 (m, 1H), 1.36 (d, J=7.0 Hz, 3H), 0.84 (d, J=6.6 Hz, 6H). LCMS (ESI) m/z calcd for C$_{21}$H$_{28}$F$_3$N$_5$O$_3$S: 487.19. Found: 488.53 (M+1)$^+$.

Example 4

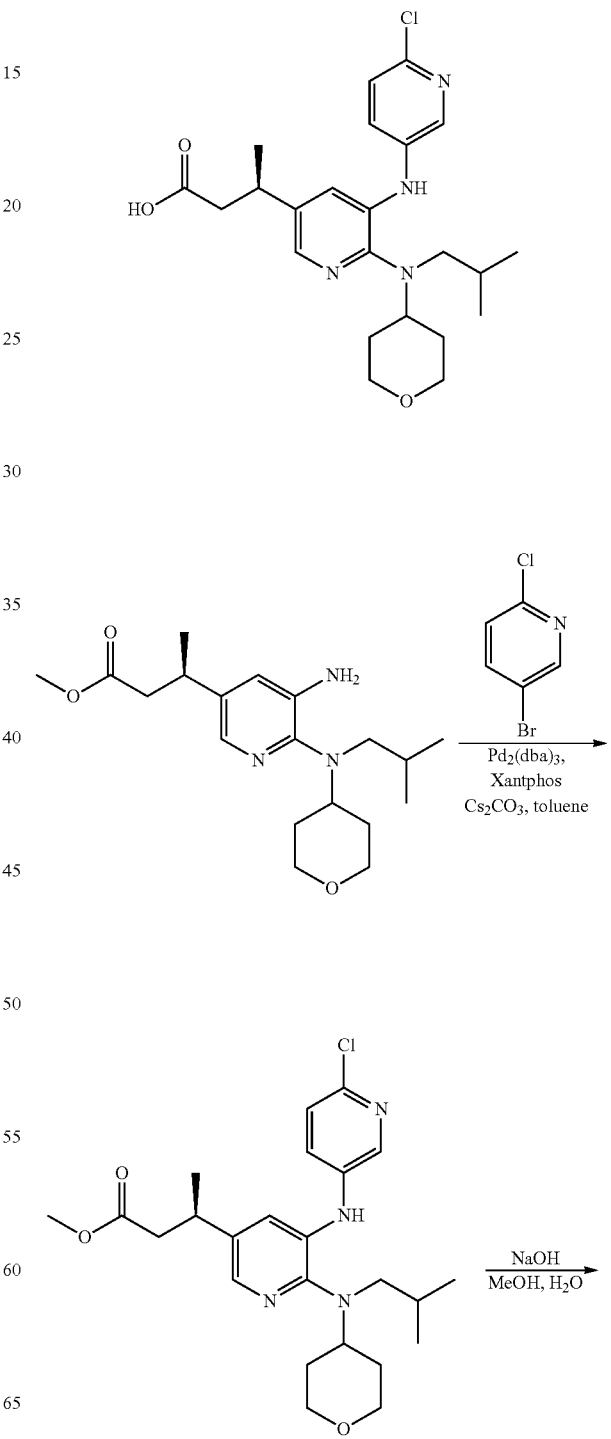

27

-continued

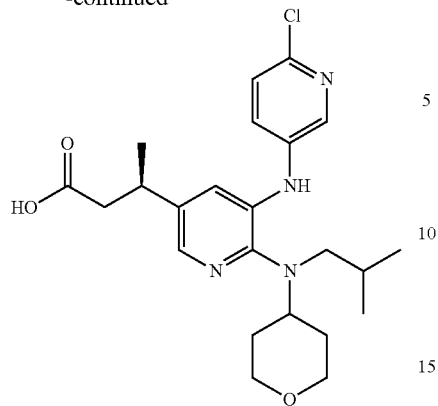

Preparation of methyl (R)-3-(5-((6-chloropyridin-3-yl)amino)-6-(isobutyl(tetra hydro-2H-pyran-4-yl)amino)pyridin-3-yl)butanoate

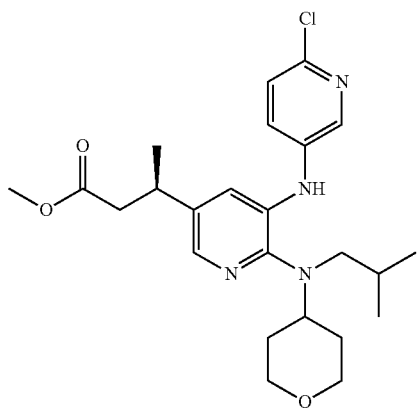 [SMILES: COC(=O)C[C@@H](C)c1cnc(N(CC(C)C)C2CCOCC2)c(Nc2ccc(Cl)nc2)c1]

A mixture of methyl (R)-3-(5-amino-6-(isobutyl(tetrahydro-2H-pyran-4-yl)amino) pyridin-3-yl)butanoate (170 mg, 0.487 mmol), 5-bromo-2-chloropyridine (187 mg, 0.972 mmol), Pd$_2$(dba)$_3$ (89 mg, 0.092 mmol), Xantphos (112 mg, 0.194 mmol) and Cs$_2$CO$_3$ (317 mg, 0.975 mmol) in toluene (2 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (140 mg, 63% yield). LCMS (ESI) m/z calcd for C$_{24}$H$_{33}$ClN$_4$O$_3$: 460.22. Found: 461.62/463.59 (M/M+2)$^+$.

28

Preparation of (R)-3-(5-(((6-chloropyridin-3-yl)amino)-6-(isobutyl(tetrahydro-2H-pyran-4-yl)amino)pyridin-3-yl)butanoic acid

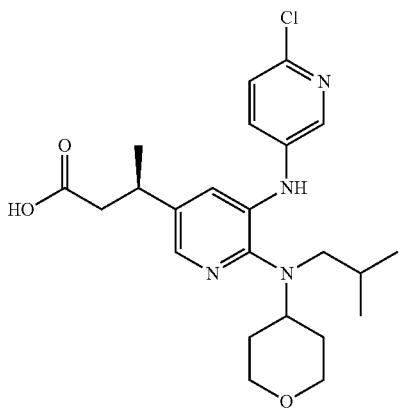 [SMILES: CC(C)CN(c1ncc([C@H](C)CC(=O)O)cc1Nc1ccc(Cl)nc1)C1CCOCC1]

To a solution of methyl (R)-3-(5-(((6-chloropyridin-3-yl)amino)-6-(isobutyl(tetrahydro-2H-pyran-4-yl)amino)pyridin-3-yl)butanoate (140 mg, 0.304 mmol) in MeOH (9 mL) was added 1N NaOH aq. (3 mL). After stirred at r.t overnight, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (57 mg, 42% yield) as a white powder. $^1$H NMR (400 MHz, CDCl$_3$) δ 8.26 (d, J=2.8 Hz, 1H), 7.90 (d, J=2.0 Hz, 1H), 7.40-7.33 (m, 2H), 7.28-7.26 (m, 1H), 6.78 (s, 1H), 3.97-3.89 (m, 2H), 3.31-3.21 (m, 3H), 3.03-2.93 (m, 3H), 2.60 (d, J=7.3 Hz, 2H), 1.77-1.62 (m, 4H), 1.41-1.29 (m, 4H), 0.84 (d, J=6.6 Hz, 6H). LCMS (ESI) m/z calcd for C$_{23}$H$_{31}$ClN$_4$O$_3$: 446.21. Found: 447.56/449.53 (M/M+2)$^+$.

Example 5

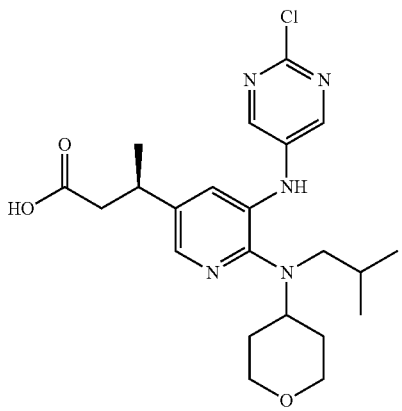

-continued

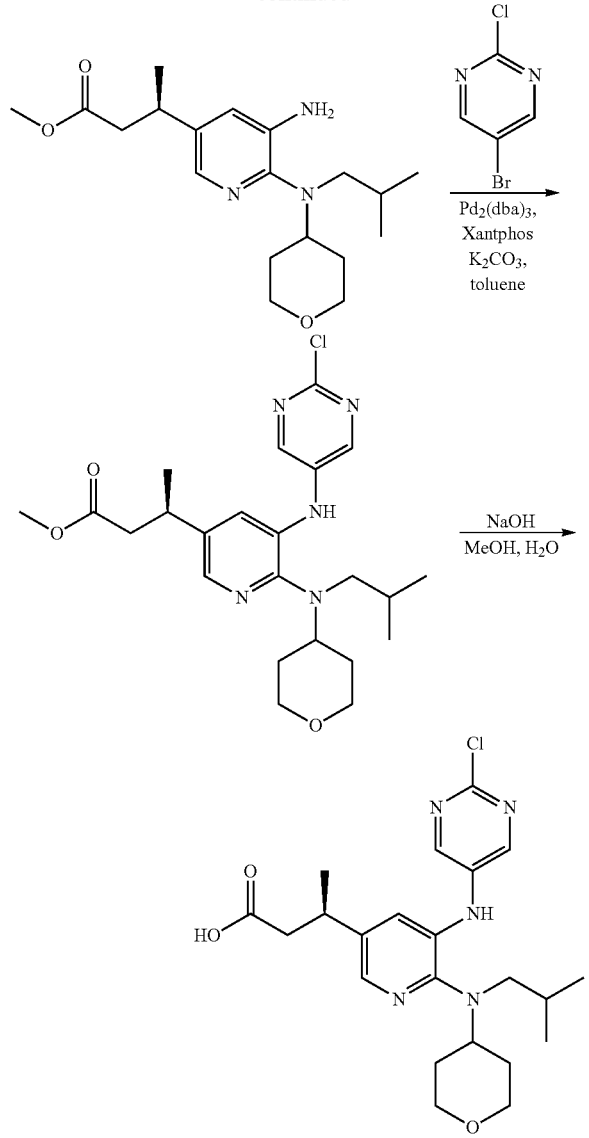

Preparation of methyl (R)-3-(5-((2-chloropyrimidin-5-yl)amino)-6-(isobutyl(tetra hydro-2H-pyran-4-yl)amino)pyridin-3-yl)butanoate

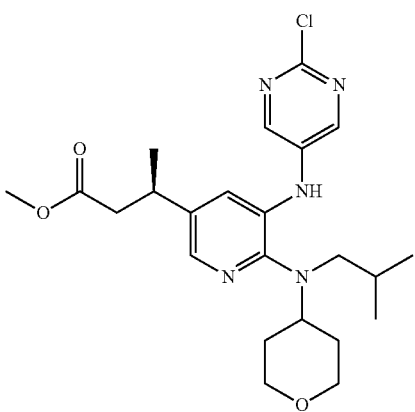 [SMILES: COC(=O)C[C@@H](C)c1cnc(N(CC(C)C)C2CCOCC2)c(Nc2cnc(Cl)nc2)c1]

A mixture of methyl (R)-3-(5-amino-6-(isobutyl(tetrahydro-2H-pyran-4-yl)amino) pyridin-3-yl)butanoate (170 mg, 0.487 mmol), 5-bromo-2-chloropyrimidine (188 mg, 0.974 mmol), Pd$_2$(dba)$_3$ (89 mg, 0.092 mmol), Xantphos (112 mg, 0.194 mmol) and K$_2$CO$_3$ (202 mg, 1.464 mmol) in toluene (2 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (130 mg, 58% yield). LCMS (ESI) m/z calcd for C$_{23}$H$_{32}$ClN$_5$O$_3$: 461.22. Found: 462.60/464.58 (M/M+2)$^+$.

Preparation of (R)-3-(5-((2-chloropyrimidin-5-yl)amino)-6-(isobutyl(tetrahydro-2H-pyran-4-yl)amino)pyridin-3-yl)butanoic acid

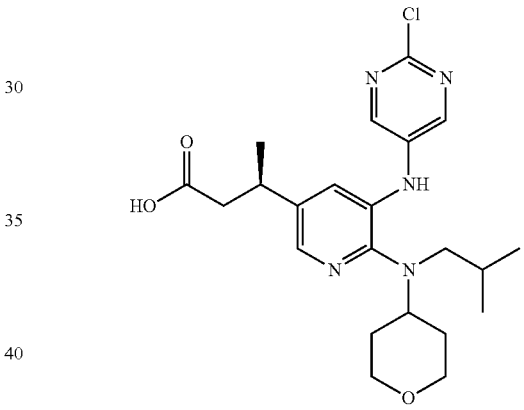

To a solution of methyl (R)-3-(5-((2-chloropyrimidin-5-yl)amino)-6-(isobutyl(tetra hydro-2H-pyran-4-yl)amino)pyridin-3-yl)butanoate (130 mg, 0.282 mmol) in MeOH (6 mL) was added 4N NaOH aq. (1.5 mL). After stirred at r.t for 24 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (57 mg, 45% yield) as a white powder. $^1$H NMR (400 MHz, CDCl$_3$) δ 8.49 (s, 2H), 7.97 (d, J=2.0 Hz, 1H), 7.39 (d, J=2.0 Hz, 1H), 6.87 (s, 1H), 3.99-3.92 (m, 2H), 3.34-3.23 (m, 3H), 3.04-2.94 (m, 3H), 2.67-2.57 (m, 2H), 1.78-1.64 (m, 4H), 1.44-1.32 (m, 4H), 0.84 (d, J=6.6 Hz, 6H). LCMS (ESI) m/z calcd for C$_{22}$H$_{30}$ClN$_5$O$_3$: 447.22. Found: 448.47/450.44 (M/M+2)$^+$.

Example 6

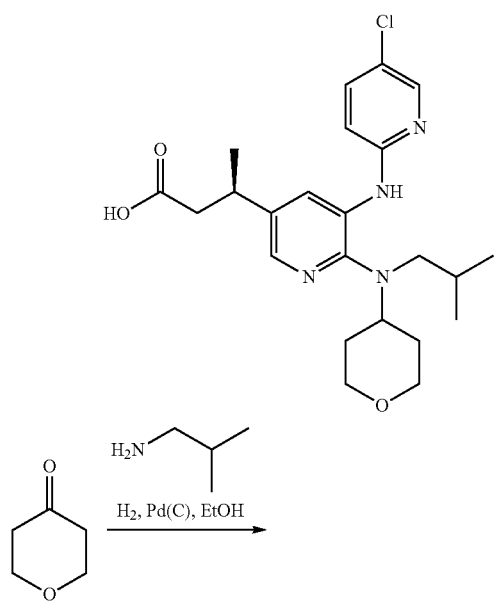

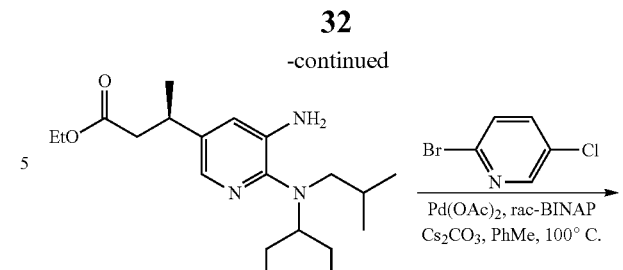

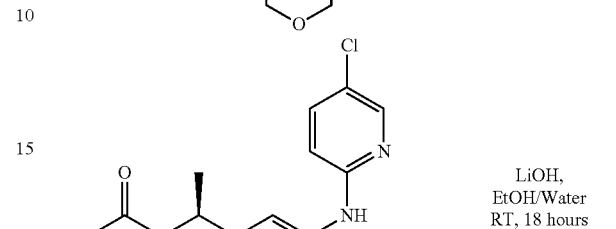

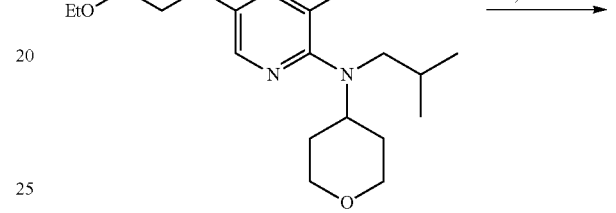

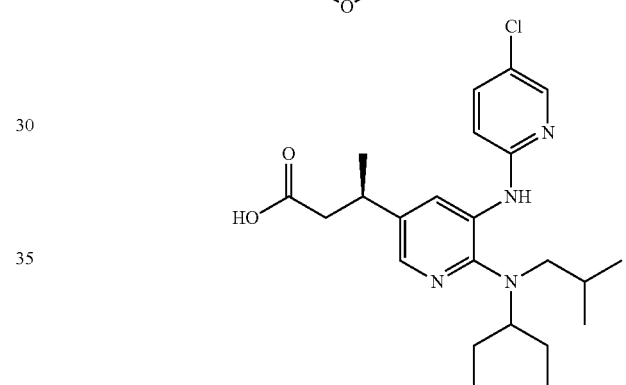

Preparation of N-isobutyltetrahydro-2H-pyran-4-amine

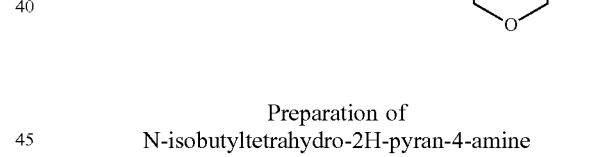

A solution of dihydro-2H-pyran-4(3H)-one (13.8 mL, 150 mmol) and isobutylamine (14.9 mL, 150 mmol) in EtOH (150 mL) was subjected to hydrogenation at 60 psi in the presence of 10% Pd/C (2.39 g). After 2 days the vessel was purged with nitrogen, catalyst removed by filtration through celite, and the filtrate concentrated at reduced pressure to give a white solid. This material was combined with material from two additional, identical reactions and suspended in ether (450 mL). The mixture was briefly sonicated and then stirred vigorously for 30 minutes. The solid was collected by filtration, dried in vacuo to afford the title compound as a white solid (50.2 g, 71% yield). ¹H NMR (400 MHz, CDCl₃) δ 9.53 (br s, 1H), 4.13-3.99 (m, 2H), 3.46-3.21 (m, 3H), 2.79 (br s, 2H), 2.35-2.15 (m, 3H), 2.14-1.97 (m, 2H), 1.14 (d, J=6.6 Hz, 6H).

Preparation of 5-bromo-N-isobutyl-3-nitro-N-(tetrahydro-2H-pyran-4-yl)pyridin-2-amine

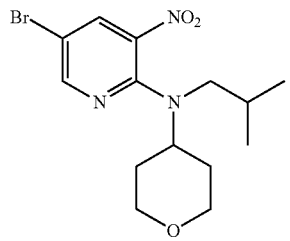 [SMILES: CC(C)CN(c1ncc(Br)cc1[N+](=O)[O-])C1CCOCC1]

A stirred suspension of 5-bromo-2-chloro-3-nitropyridine (30.0 g, 126 mmol) and N-isobutyltetrahydro-2H-pyran-4-amine (25.8 g, 164 mmol) in NMP (211 mL) was treated with DIEA (44.1 mL, 253 mmol) and heated to 100° C. (internal temperature) under nitrogen. After 14 hours the reaction mixture was cooled to RT, transferred to a separatory funnel and diluted with EtOAc (800 mL). After addition of 1 L of water the mixture was shaken and the phases separated. The aqueous phase was extracted with one additional 200 mL portion of EtOAc. The combined EtOAc solutions were washed with 5% aqueous citric acid (2×500 mL), half saturated aqueous NaHCO₃ (2×500 mL), dried over Na₂SO₄, and concentrated to dryness in the presence of silica gel, and the material subjected to flash chromatography (750 g silica gel column, dry loading, 0-25% EtOAc/hexanes, gradient elution) to afford the title compound as a yellow solid (26.5 g, 58%). LCMS (ESI) m/z calcd for C₁₄H₂₀BrN₃O₃: 357.07. Found: 358.21 (M+1)⁺. ¹H NMR (400 MHz, CDCl₃) δ 8.36 (d, J=2.2 Hz, 1H), 8.21 (d, J=2.2 Hz, 1H), 4.02 (dd, J=11.5, 4.6 Hz, 2H), 3.58-3.72 (m, 1H), 3.39 (td, J=11.8, 1.7 Hz, 2H), 3.13 (d, J=7.3 Hz, 2H), 1.68-1.99 (m, 5H), 0.84 (d, J=6.6 Hz, 6H).

Preparation of (Z)-ethyl 3-(4,4,5,5-tetramethyl-1,3,2-dioxaborolan-2-yl)but-2-enoate

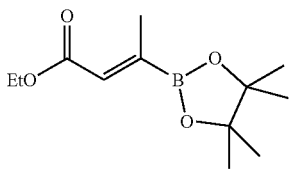 [SMILES: CCOC(=O)/C=C(\C)B1OC(C)(C)C(C)(C)O1]

To a stirred mixture of ethyl but-2-ynoate (41.7 mL, 359 mmol), bis(pinacolato)diboron (50.0 g, 197 mmol) and 4-methylpyridine (1.76 mL, 17.9 mmol) was added a solution of copper(II) sulfate (0.572 g, 3.59 mmol) in water (414 mL). After 5 min more bis(pinacolato)diboron (50.0 g, 197 mmol) was added and the mixture turned darker and an exotherm (65° C.) was observed. The mixture was stirred at ambient temperature for 3.5 h. Water (400 mL) was added and the mixture was filtered through a fritted glass filter washing with water and hexanes. The filtrate was extracted with hexanes and the organic phase separated, washed with water (3×), dried (Na₂SO₄) and concentrated (34° C. bath temperature, 50 mbar) to provide the title compound as a colorless liquid in quantitative yield. ¹H NMR (400 MHz, CDCl₃) δ 6.45 (d, J=1.7 Hz, 1H) 4.18 (q, J=7.1 Hz, 2H) 2.17 (d, J=1.7 Hz, 3H) 1.17-1.41 (m, 15H).

Preparation of (E)-ethyl 3-(6-(isobutyl(tetrahydro-2H-pyran-4-yl)amino)-5-nitropyridin-3-yl)but-2-enoate

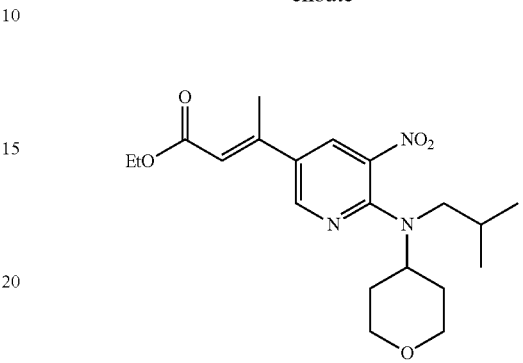

To a solution of 5-bromo-N-isobutyl-3-nitro-N-(tetrahydro-2H-pyran-4-yl)pyridin-2-amine (40.0 g, 112 mmol) in DMF (720 mL) under a stream of nitrogen was added ethyl (Z)-3-(4,4,5,5-tetramethyl-1,3,2-dioxaborolan-2-yl)but-2-enoate (40.2 g, 167 mmol), Pd(PPh₃)₄ (6.45 g, 5.58 mmol) and 2 M aqueous Na₂CO₃ (167 mL, 335 mmol). The mixture was heated to 100° C. (internal temp.) with a heating mantle under a nitrogen atmosphere for 1 h. The mixture was cooled to ambient temperature then cooled in ice-water and stirred for 1 h. The solid was filtered washing with DMF (3×135 mL) and water (1600 mL). The yellow solid was dried in vacuo (18 h) to provide the title compound (36.0 g, 82% yield) as a yellow solid. LCMS (ESI) m/z calcd for C₂₀H₂₉N₃O₅: 391.21. Found: 392.35 (M+1)⁺. ¹H NMR (400 MHz, CDCl₃) δ 8.52 (d, J=2.2 Hz, 1H), 8.22 (d, J=2.2 Hz, 1H), 6.16 (d, J=1.1 Hz, 1H), 4.23 (d, J=7.14 Hz, 2H), 3.92-4.11 (m, 2H), 3.64-3.88 (m, 1H), 3.30-3.55 (m, 2H), 3.19 (d, J=7.3 Hz, 2H), 2.57 (d, J=0.9 Hz, 3H), 1.69-2.08 (m, 5H), 1.33 (t, J=7.1 Hz, 3H), 0.85 (d, J=6.6 Hz, 6H).

Preparation of (R)-ethyl 3-(6-(isobutyl(tetrahydro-2H-pyran-4-yl)amino)-5-nitropyridin-3-yl)butanoate

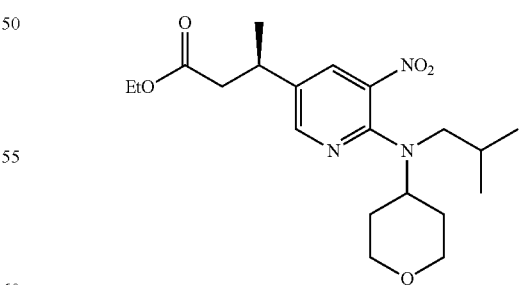

A nitrogen filled, round bottomed flask equipped with a magnetic stirrer was charged with [Ph₃PCuH]₆ (4.88 g, 2.49 mmol) followed by (R)-(−)-1-[(S)-2-(diphenylphosphino)ferrocenyl]ethyldi-t-butylphosphine (4.86 g, 8.97 mmol). The vessel was capped with a rubber septum and gently purged with nitrogen for 10 min. To the vessel was added anhydrous toluene (100 mL). After cooling in an ice water-brine bath, poly(methylhydrosiloxane) (7.12 mL, Sigma Adrich cat. number 81330) followed by tBuOH (5.72 mL, 59.8 mmol) was added. After 10 min, this solution was transferred via cannula to a stirred suspension of (E)-ethyl 3-(6-(isobutyl(tetrahydro-2H-pyran-4-yl)amino)-5-nitropyridin-3-yl)but-2-enoate (19.5 g, 49.8 mmol) in toluene (100 mL) (cooled in an ice water-brine bath). After 20 min, the solution was allowed to warm to RT. After 16 hours LCMS indicated complete conversion of starting material to the desired product. The reaction mixture was concentrated to dryness in the presence of silica gel, and the material subjected to flash chromatography (750 g silica gel column, dry loading, 0-30% EtOAc/hexanes gradient elution) to afford the title compound (15.1 g, 77%) as a yellow oil. LCMS (ESI) m/z calcd for $C_{20}H_{31}N_3O_5$: 393.23. Found: 394.38 (M+1)+. $^1$H NMR (400 MHz, CDCl$_3$) δ 8.26 (d, J=2.2 Hz, 1H), 7.95 (d, J=2.2 Hz, 1H), 4.05-4.16 (m, 2H), 4.00 (dd, J=11.5, 4.3 Hz, 2H), 3.50-3.63 (m, 1H), 3.25-3.44 (m, 3H), 3.13 (d, J=7.3 Hz, 2H), 2.57 (d, J=7.5 Hz, 2H), 1.69-1.97 (m, 5H), 1.32 (d, J=7.1 Hz, 3H), 1.19 (t, J=7.1 Hz, 3H), 0.84 (d, J=6.6 Hz, 6H).

Preparation of (R)-ethyl 3-(5-amino-6-(isobutyl(tetrahydro-2H-pyran-4-yl)amino)pyridin-3-yl)butanoate

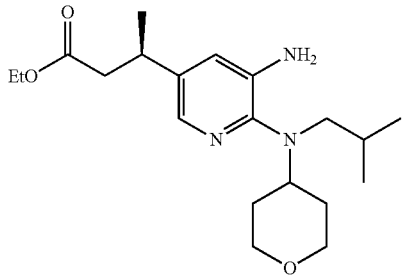 [SMILES: CCOC(=O)C[C@@H](C)c1cnc(N(CC(C)C)C2CCOCC2)c(N)c1]

To a stirred solution of (R)-ethyl 3-(6-(isobutyl(tetrahydro-2H-pyran-4-yl)amino)-5-nitropyridin-3-yl)butanoate (15.0 g, 38.1 mmol) in EtOH (225 mL) was added a suspension of NH$_4$Cl (40.8 g, 762 mmol) in water (112 mL). A thick yellow-orange suspension formed. Additional EtOH was added to improve stirring. The mixture was cooled in an ice water bath and was treated with zinc dust (24.9 g, 381 mmol). After 15 minutes the mixture was allowed to warm to RT. After 2.0 hours LCMS indicated complete reaction. The mixture was filtered to remove solids, washing with EtOH (3×). The filtrate was concentrated nearly to dryness at reduced pressure. The residue was partitioned between DCM and water and the phases separated. The aqueous phase was extracted with two additional portions of DCM. The combined DCM solutions were dried over Na$_2$SO$_4$ and concentrated at reduced pressure. The crude material was subjected to flash chromatography (330 g silica gel, 0-10% MeOH/DCM, gradient elution) to afford the title compound (12.4 g, 89% yield). LCMS (ESI) m/z calcd for $C_{20}H_{33}N_3O_3$: 363.25. Found: 364.38 (M+1)+. $^1$H NMR (400 MHz, CDCl$_3$) δ 7.70 (d, J=1.7 Hz, 1H), 6.85 (br s, 1H), 4.08 (q, J=7.1 Hz, 2H), 3.84-4.02 (m, 4H), 3.33 (t, J=11.1 Hz, 2H), 3.13-3.24 (m, 1H), 2.88-3.11 (m, 3H), 2.42-2.62 (m, 2H), 1.72-1.87 (m, 2H), 1.59-1.70 (m, 2H), 1.42 (dt, J=13.2, 6.7 Hz, 1H) 1.28 (d, J=7.0 Hz, 3H) 1.17 (t, J=7.1 Hz, 3H) 0.82 (d, J=6.6 Hz, 6H). The enantiomeric purity was determined to be 98% ee by chiral analytical HPLC versus an authentic racemic standard. [Agilent 1100 HPLC System, Regis (S,S) Whelk-O1 column (4.6 mm×259 mm, 5 μm), 10% IPA/hexanes isocratic, flow rate=1.5 mL/min, monitored at 254 nM].

Preparation of (R)-ethyl 3-(5-((5-chloropyridin-2-yl)amino)-6-(isobutyl(tetrahydro-2H-pyran-4-yl)amino)pyridin-3-yl)butanoate

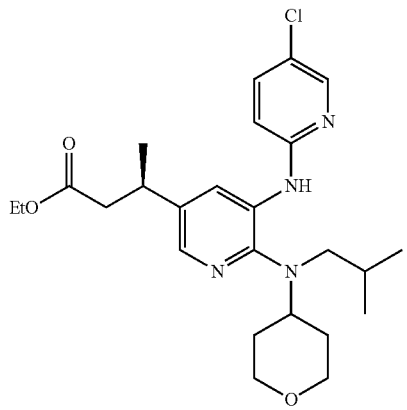 [SMILES: CC(C)CN(c1ncc([C@H](C)CC(=O)O)cc1Nc1ccc(Cl)cn1)C1CCOCC1]

A degassed solution of (R)-ethyl 3-(5-amino-6-(isobutyl(tetrahydro-2H-pyran-4-yl)amino)pyridin-3-yl)butanoate (15.9 g, 43.7 mmol) in toluene (437 ml) was treated with 2-bromo-5-chloropyridine (10.1 g, 52.5 mmol), Pd(OAc)$_2$ (1.96 g, 8.75 mmol), rac-BINAP (7.63 g, 12.2 mmol), and C$_s$2CO$_3$ (25.7 g, 79.0 mmol). The mixture was sparged with nitrogen for 10 min, and then stirred at 100° C. (internal temperature). After 1.5 hours LCMS indicated complete reaction. The mixture was cooled to RT and filtered to remove solids, washing with EtOAc. The filtrate was concentrated to a syrup at reduced pressure. This material was dissolved in EtOAc and the solution concentrated in the presence of silica gel, and the material subjected to flash chromatography (750 g silica gel column, dry loading, 0-100% EtOAc/hexanes, gradient elution) to afford 10.7 g of pure product and 3.39 g of impure material. The impure product was subjected to a second chromatography (120 g silica gel column, 0-50% EtOAc/DCM, gradient elution) to give an additional 2.75 g of pure material for a total yield of 13.5 g (65%) of the title compound. LCMS (ESI) m/z calcd for $C_{25}H_{35}ClN_4O_3$: 474.24. Found: 364.38 (M+1)+. $^1$H NMR (400 MHz, CDCl$_3$) δ 8.54 (br s, 1H), 8.23 (d, J=2.4 Hz, 1H), 7.90 (d, J=1.8 Hz, 1H), 7.84 (br s, 1H), 7.50 (dd, J=8.8, 2.6 Hz, 1H), 6.66 (d, J=8.8 Hz, 1H), 4.11 (q, J=7.1 Hz, 2H), 3.94 (d, J=11.0 Hz, 2H), 3.20-3.37 (m, 3H), 2.94-3.06 (m, 3H), 2.53-2.70 (m, 2H), 1.62-1.80 (m, 4H), 1.31-1.46 (m, 4H), 1.20 (t, J=7.1 Hz, 3H), 0.86 (d, J=6.6 Hz, 6H).

Preparation of (R)-3-(5-((5-chloropyridin-2-yl)amino)-6-(isobutyl(tetrahydro-2H-pyran-4-yl)amino)pyridin-3-yl)butanoic acid

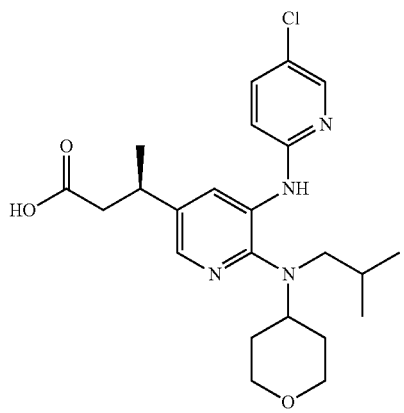

To a stirred solution of ethyl (R)-3-(5-((5-chloropyridin-2-yl)amino)-6-(isobutyl(tetrahydro-2H-pyran-4-yl)amino)pyridin-3-yl)butanoate (25.5 g, 53.7 mmol) in THF (450 mL) was added EtOH (150 mL) followed by 4M aqueous LiOH (134 mL, 537 mmol). The resulting mixture was diluted with water (20 mL) and stirred at RT. After 18 hours LCMS indicated complete reaction. The mixture was filtered through a medium fritted funnel to remove solids. The filter cake was washed with EtOH (2×) and discarded. The filtrate was concentrated to about one third volume by rotary evaporation. The filtrate was treated with 1N aqueous HCl until a pH of 5 was reached, which required 165 mL of HCl solution. The resulting cloudy mixture was diluted with EtOAc (200 mL), stirred vigorously for several minutes, and the phases separated. The aqueous phase was extracted with additional EtOAc (3×50 mL). The combined EtOAc solutions were washed with saturated aqueous brine (1×100 mL), dried over $Na_2SO_4$, and concentrated to dryness at reduced pressure to give a tan foam (25.1 g). The crude product was treated to remove residual palladium as follows. The foam was dissolved in MeOH (400 mL) and the solution treated with SiliaMet®Thiol resin (loading 1.42 mmol/g) (41 g). The mixture was stirred at RT overnight. The mixture was treated with 20 g of Celite, stirred for 15 minutes, and then filtered through a medium fritted funnel, washing with excess MeOH. The filtrate, which was slightly cloudy, was concentrated at reduced pressure. The residue was redissolved in 1:1 DCM/EtOAc to give a cloudy solution that was filtered through celite, washing with 1:1 DCM/EtOAc. The clear filtrate was concentrated at reduced pressure to afford the title compound as a light yellow foam in quantitative yield. LCMS (ESI) m/z calcd for $C_{23}H_{31}ClN_4O_3$: 446.21. Found: 447.37 (M+1)+. $^1$H NMR (400 MHz, CDCl$_3$) δ 8.52 (d, J=2.0 Hz, 1H), 8.22 (d, J=2.4 Hz, 1H), 7.94 (d, J=2.0 Hz, 1H), 7.88 (s, 1H), 7.49 (dd, J=8.8, 2.6 Hz, 1H), 6.66 (d, J=8.8 Hz, 1H), 3.94 (d, J=10.8 Hz, 2H), 3.20-3.39 (m, 3H), 2.92-3.09 (m, 3H), 2.56-2.75 (m, 2H), 1.61-1.79 (m, 4H), 1.34-1.47 (m, 4H), 0.85 (d, J=6.6 Hz, 6H). The product was combined with an additional 59.9 g of purified material an crystallized as follows. The material (84.1 g total) was dissolved in 1:1 DCM/EtOAc (500 mL) and the slightly cloudy solution filtered through a bed of celite, washing with DCM. The filtrate was concentrated to a syrup (volume of approximately 150 mL). The viscous solution was stirred with slow addition of hexanes via addition funnel. The solution was seeded with a few mg of authentic, crystalline product after addition of 100, 150, and 200 mL of hexanes, resulting in slow crystallization. A total of 700 mL of hexanes was added over a 2 h period. After 18 h, the suspension was cooled in an ice water bath and stirring continued. After 3 h in the ice water bath, the solid was collected by vacuum filtration and the filter cake was washed twice with ice cold 7:1 hexanes/EtOAc. After suction air drying for 1 h, the solid was dried in vacuo over night to afford the title compound (79.5 g) as an off-white solid, that was determined to be crystalline by polarized light microscopy and XRPD analysis.

Example 7

Preparation of (R)-3-(5-((5-chloro-6-fluoropyridin-2-yl)amino)-6-(isobutyl(tetrahydro-2H-pyran-4-yl)amino)pyridin-3-yl)butanoic acid

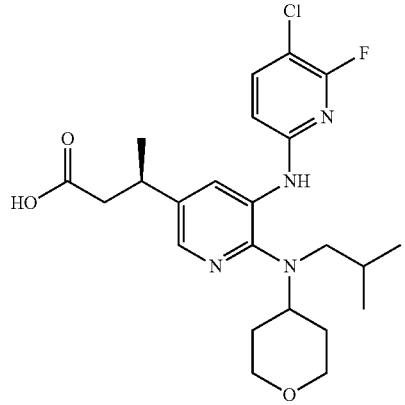

A solution of (R)-ethyl 3-(5-amino-6-(isobutyl(tetrahydro-2H-pyran-4-yl)amino)pyridin-3-yl)butanoate (83 mg, 0.228 mmol) in Toluene (3.4 mL) was degassed while adding 6-bromo-3-chloro-2-fluoropyridine (57.7 mg, 0.274 mmol), cesium carbonate (134 mg, 0.411 mmol), BINAP (39.8 mg, 0.064 mmol) and finally PdOAc$_2$ (10.25 mg, 0.046 mmol). The mixture was degassed for one additional minute. The flask containing the mixture was immersed into a 100° C. oil bath and allowed to stir for one hour at 100° C. and then at ambient temperature overnight. The mixture was partitioned between EtOAc and water. The layers were separated and the aqueous phase was further extracted with EtOAc. The combined extracts were washed with brine, dried over sodium sulfate, filtered and concentrated. The residue was purified on silica gel (12 g column, 0-30% hexanes/EtOAc) to afford (R)-ethyl 3-(5-amino-6-(isobutyl(tetrahydro-2H-pyran-4-yl)amino)pyridin-3-yl)butanoate as a sticky pale yellow residue. A solution of (R)-ethyl 3-(5-amino-6-(isobutyl(tetrahydro-2H-pyran-4-yl)amino)pyridin-3-yl)butanoate (95 mg, 0.191 mmol) in THF (1.4 mL) and EtOH (0.7 mL) was treated with 2M LiOH (0.685 mL, 1.370 mmol) and the mixture was allowed to stir at ambient temperature for 4 hours. The mixture was concentrated. Water was added and the mixture was made acidic (~pH 3-4) with 1N HCl then extracted with EtOAc. The extracts were washed with brine, dried over sodium sulfate filtered and concentrated. The residue was purified by reverse phase chromatography to afford a tan solid (50 mg). $^1$H NMR (400

MHz, CHLOROFORM-d) 5=8.51 (s, 1H), 7.97 (s, 2H), 7.60 (t, J=8.8 Hz, 1H), 6.54 (d, J=8.4 Hz, 1H), 3.95 (m, 2H), 3.42-3.19 (m, 3H), 2.99 (m, 3H), 2.79-2.59 (m, 2H), 1.70 (m, 4H), 1.40 (m, 4H), 0.86 (d, J=6.4 Hz, 6H); LC/MS (m/z) ES+ calcd for $C_{23}H_{30}ClFN_4O_3$: 464.20. Found: 465 (M+1).

Example 8

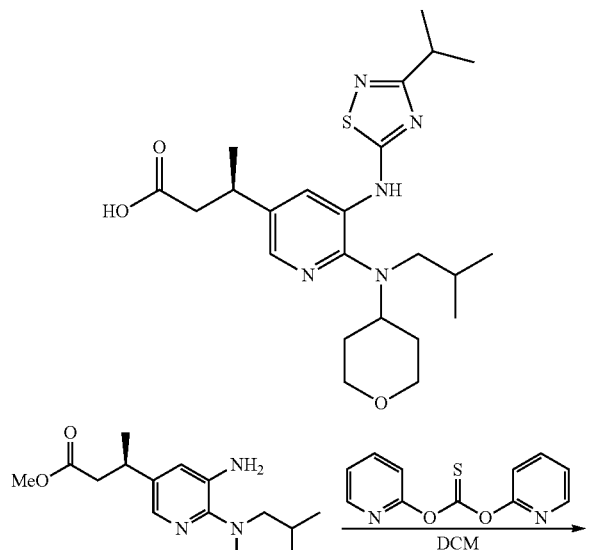

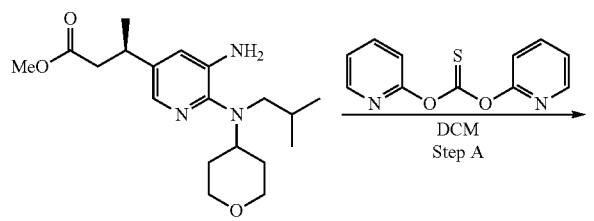

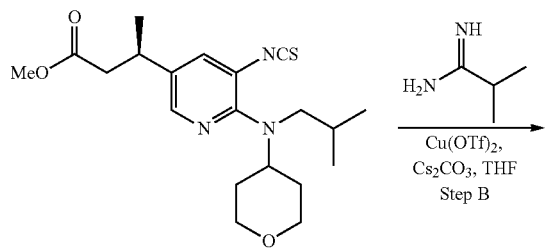

Preparation of (R)-methyl 3-(6-(isobutyl(tetrahydro-2H-pyran-4-yl)amino)-5-isothiocyanatopyridin-3-yl)butanoate

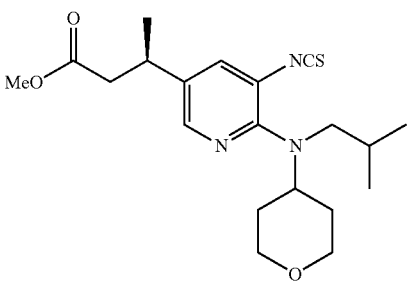

(R)-Methyl 3-(5-amino-6-(isobutyl(tetrahydro-2H-pyran-4-yl)amino)pyridin-3-yl)butanoate (100 mg, 0.287 mmol) and O,O-di(pyridin-2-yl) carbonothioate (100 mg, 0.430 mmol) in dichloromethane (3.0 mL) was stirred at r.t. for 16 h. The reaction mixture was concentrated and used in the next step without further purification.

Preparation of (R)-methyl 3-(6-(isobutyl(tetrahydro-2H-pyran-4-yl)amino)-5-((3-isopropyl-1,2,4-thiadiazol-5-yl)amino)pyridin-3-yl)butanoate

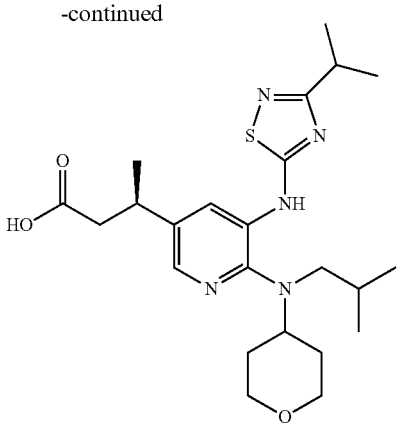

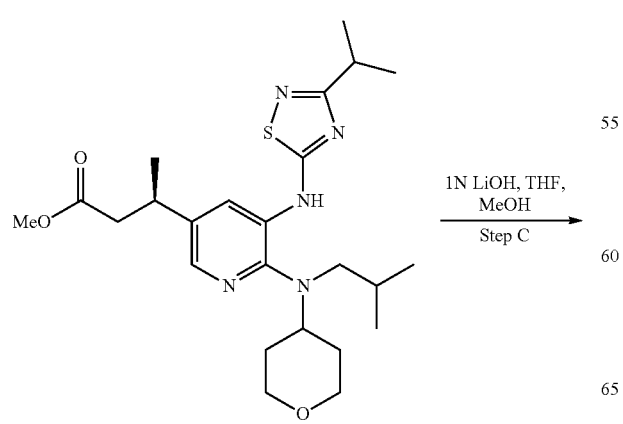

(R)-Methyl 3-(6-(isobutyl(tetrahydro-2H-pyran-4-yl)amino)-5-isothiocyanatopyridin-3-yl)butanoate and cesium carbonate (280 mg, 0.861 mmol) were dissolved in ACN (3.00 mL), copper(II) trifluoromethanesulfonate (5.19 mg, 0.014 mmol) and isobutyrimidamide, Hydrochloride (52.8 mg, 0.430 mmol) were added to the solution and the mixture was stirred at r.t for 2 h under air. The reaction mixture was diluted with water, extracted with ethyl acetate, the organic phase was dried over sodium sulfate and concentrated. Crude product was used in the next step without further purification.

Preparation of ((R)-3-(6-(isobutyl(tetrahydro-2H-pyran-4-yl)amino)-5-((3-isopropyl-1,2,4-thiadiazol-5-yl)amino)pyridin-3-yl)butanoic acid

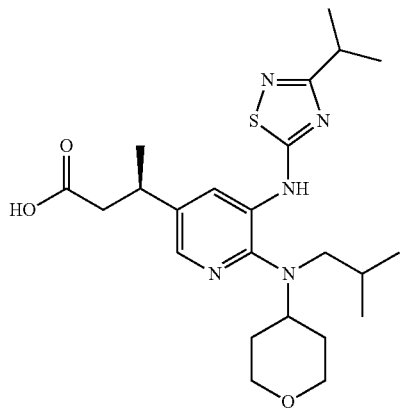 [SMILES: CC(C)CN(c1ncc([C@H](C)CC(=O)O)cc1Nc1nc(C(C)C)ns1)C1CCOCC1]

(R)-Methyl 3-(6-(isobutyl(tetrahydro-2H-pyran-4-yl)amino)-5-((3-isopropyl-1,2,4-thiadiazol-5-yl)amino)pyridin-3-yl)butanoate was dissolved in THF (5 mL) and MeOH (3 mL) and treated with LiOH (1.435 mL, 1.435 mmol) and the mixture was stirred at r.t. for 3 h. The reaction mixture was concentrated to a smaller volume, neutralized with 1N HCl, extracted with ethyl acetate, dried over sodium sulfate and concentrated. Purification by reverse phase chromatography afforded the desired product. LCMS calculated for $C_{23}H_{35}N_5O_3S$: 461.25, found (M+H)+: m/z=462.15

$^1$H NMR (400 MHz, METHANOL-$d_4$) δ ppm 8.51 (s, 1H) 7.98 (s, 1H) 3.88 (d, J=11.1 Hz, 2 H) 3.00-3.18 (m, 2H) 2.98 (d, J=6.8 Hz, 2H) 2.60 (d, J=7.4 Hz, 2H) 1.67 (br. s., 4H) 1.35-1.47 (m, 4H) 1.33 (d, J=6.8 Hz, 9H) 0.81 (d, J=6.6 Hz, 6H).

Example 9

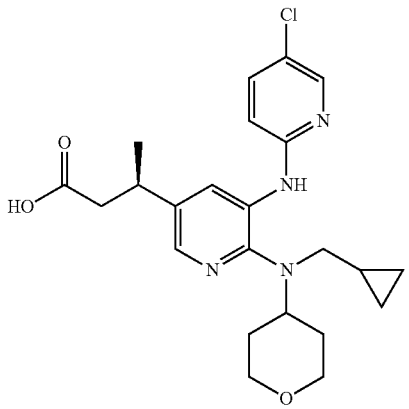 [SMILES: C[C@H](CC(=O)O)c1cnc(N(CC2CC2)C2CCOCC2)c(Nc2ccc(Cl)cn2)c1]

Preparation of N-(cyclopropylmethyl)tetrahydro-2H-pyran-4-amine hydrochloride

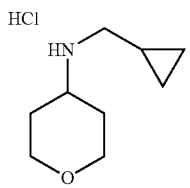

A solution of cyclopropylmethanamine (0.915 ml, 10.55 mmol) and dihydro-2H-pyran-4(3H)-one (0.974 ml, 10.55 mmol) in MeOH (52.7 ml) was purged with nitrogen. The reaction was treated with 10% Pd—C (0.200 g, 0.188 mmol) and placed under a hydrogen atmosphere (60 psi) overnight. The reaction was filtered over celite rinsing with MeOH. The solution was then treated with 4N in dioxanes HCl (5.27 ml, 21.09 mmol). The solvents were removed under reduced pressure and the oily residue was concentrated from $Et_2O$ several time, and then from DCM several times. The solid residue was triturated with $Et_2O$ to give N-(cyclopropylmethyl)tetrahydro-2H-pyran-4-amine hydrochloride (1.961 g, 10.23 mmol, 97% yield) as a white solid. $^1$H NMR (400 MHz, DMSO-$d_6$) δ ppm 9.26 (br. s., 2H) 3.83-3.95 (m, 2H) 3.34-3.41 (m, 1H) 3.23-3.32 (m, 2H) 2.74-2.82 (m, 2H) 1.95 (d, J=12.27 Hz, 2H) 1.69-1.60 (m, 2H) 1.05-1.14 (m, 1H) 0.52-0.60 (m, 2H) 0.35-0.42 (m, 2H).

Preparation of 5-bromo-N-(cyclopropylmethyl)-3-nitro-N-(tetrahydro-2H-pyran-4-yl)pyridin-2-amine

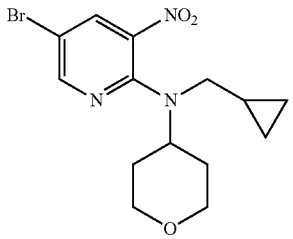 [SMILES: O=[N+]([O-])c1cc(Br)cnc1N(CC1CC1)C1CCOCC1]

A flask containing 5-bromo-2-fluoro-3-nitropyridine (1.25 g, 5.66 mmol), N-(cyclopropylmethyl)tetrahydro-2H-pyran-4-amine hydrochloride (1.247 g, 6.50 mmol), and DIEA (2.96 ml, 16.97 mmol) in NMP (17.14 ml) was heated at 90° C. for 90 minutes. The reaction was cooled to room temperature and diluted with water and extracted with EtOAc. The combined extracts were washed with brine, dried over Na$_2$SO$_4$, filtered, and concentrated onto silica gel. The residue was purified by silica gel chromatography (0-10% EtOAc/hexanes) to give 5-bromo-N-(cyclopropylmethyl)-3-nitro-N-(tetrahydro-2H-pyran-4-yl)pyridin-2-amine (1.59 g, 4.46 mmol, 79% yield) as a pale yellow solid. $^1$H NMR (400 MHz, CHLOROFORM-d) δ ppm 8.37 (s, 1H) 8.25 (s, 1H) 4.04 (dd, J=11.54, 3.48 Hz, 2H) 3.95 (t, J=11.63 Hz, 1H) 3.44 (t, J=11.72 Hz, 2H) 3.19 (d, J=6.59 Hz, 2H) 1.94 (qd, J=12.03, 4.03 Hz, 2H) 1.79 (d, J=12.09 Hz, 2H) 0.75-0.91 (m, 1H) 0.45 (d, J=7.87 Hz, 2H) 0.10-0.23 (m, 2H).

Preparation of (E)-ethyl 3-(6-((cyclopropylmethyl)(tetrahydro-2H-pyran-4-yl)amino)-5-nitropyridin-3-yl)but-2-enoate

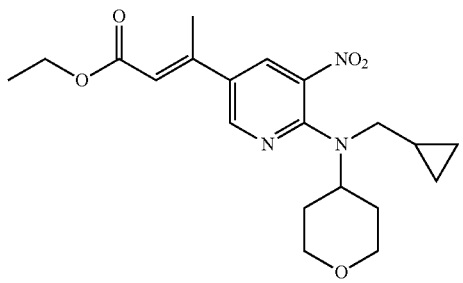 [SMILES: CCOC(=O)/C=C(\C)c1cnc(N(CC2CC2)C2CCOCC2)c([N+](=O)[O-])c1]

A solution of 5-bromo-N-(cyclopropylmethyl)-3-nitro-N-(tetrahydro-2H-pyran-4-yl)pyridin-2-amine (1.373 g, 3.85 mmol), PdCl$_2$(dppf)-CH$_2$Cl$_2$ adduct (0.094 g, 0.116 mmol), K$_2$CO$_3$ (1.598 g, 11.56 mmol) and DMF (12.85 ml) was treated with (E)-hex-4-en-3-one (2.472 ml, 23.13 mmol) and purged with nitrogen. The reaction was heated at 110° C. for 1 hour and cooled to room temperature. The mixture was diluted with EtOAc and water. The combined extracts were washed with 5% LiCl (3×), brine, dried over Na$_2$SO$_4$, filtered, and concentrated onto silica gel. The dark brown residue was purified by silica gel chromatography (20-30% EtOAc/hexanes) to give (E)-ethyl 3-(6-((cyclopropylmethyl) (tetrahydro-2H-pyran-4-yl)amino)-5-nitropyridin-3-yl) but-2-enoate (1.272 g, 3.27 mmol, 85% yield) as a yellow solid. LCMS m/z calcd for C$_{20}$H$_{27}$N$_3$O$_5$: 389.20. Found: 390.5 (M+H)+.

Preparation of (R)-ethyl 3-(6-((cyclopropylmethyl)(tetrahydro-2H-pyran-4-yl)amino)-5-nitropyridin-3-yl)butanoate

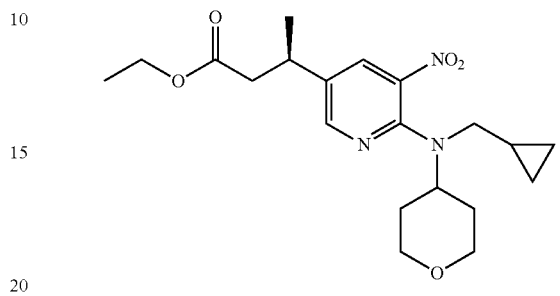

A flask containing [Ph$_3$PCuH]s (0.320 g, 0.163 mmol) and (R,S)—PPF—P(tuB)$_2$ (0.319 g, 0.588 mmol) was flushed with nitrogen for 10 minutes. The flask was then treated with toluene (5.83 ml) and cooled to 0° C. To this flask was then added poly(methylhydrosiloxane) (0.456 ml, 3.27 mmol) and tert-butanol (0.375 ml, 3.92 mmol). To this flask was added the dropwise addition of a suspension of (E)-ethyl 3-(6-((cyclopropylmethyl) (tetrahydro-2H-pyran-4-yl)amino)-5-nitropyridin-3-yl) but-2-enoate (1.272 g, 3.27 mmol) in toluene (5.83 ml) and DCE (1.5 mL). The reaction was flushed with nitrogen and slowly let warm up to room temperature overnight. The reaction was quenched by the addition of saturated NaHCO$_3$ and stirred for 1 hour. The mixture was extracted with EtOAc. The combined extracts were washed with brine, dried over Na$_2$SO$_4$, filtered, and concentrated onto silica gel. The residue was purified by silica gel chromatography (0-30% EtOAc/Hexanes) to give a residue. The residue was purified by reverse phase chromatography (10-100% ACN/H$_2$O+formic acid) and concentrated from toluene (3×) to give (R)-ethyl 3-(6-((cyclopropylmethyl)(tetrahydro-2H-pyran-4-yl)amino)-5-nitropyridin-3-yl)butanoate (0.499 g, 39% yield). $^1$H NMR (400 MHz, CHLOROFORM-d) b ppm 8.28 (d, J=2.01 Hz, 1H) 7.98 (d, J=2.01 Hz, 1H) 4.11 (q, J=7.14 Hz, 2H) 4.00-4.07 (m, 2H) 3.81-3.92 (m, 1H) 3.44 (t, J=11.72 Hz, 2H) 3.28-3.36 (m, 1H) 3.19 (d, J=6.59 Hz, 2H) 2.59 (d, J=7.51 Hz, 2H) 1.93 (qd, J=12.09, 4.21 Hz, 2H) 1.76-1.85 (m, 2H) 1.34 (d, J=6.96 Hz, 3H) 1.21 (t, J=7.14 Hz, 3H) 0.84-0.93 (m, 1H) 0.40-0.48 (m, 2H) 0.10-0.18 (m, 2H).

Preparation of (R)-ethyl 3-(5-amino-6-((cyclopropylmethyl)(tetrahydro-2H-pyran-4-yl)amino)pyridin-3-yl)butanoate

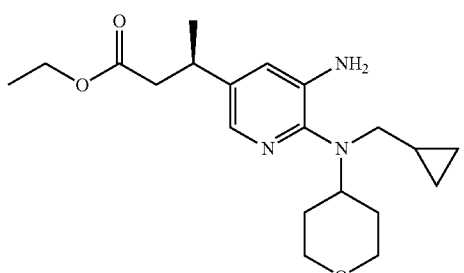

A solution of (R)-ethyl 3-(6-((cyclopropylmethyl)(tetrahydro-2H-pyran-4-yl)amino)-5-nitropyridin-3-yl)butanoate (0.379 g, 0.968 mmol) in EtOH (4.50 ml) was treated with water (0.346 ml) and ammonium chloride (0.518 g, 9.68 mmol). The mixture was stirred for 15 minutes then treated by the addition of zinc (0.633 g, 9.68 mmol). The reaction was stirred at room temperature overnight. The reaction was filtered, rinsing with EtOH. The solvents were removed under reduced pressure. The residue was taken up in EtOAc and water. The combined extracts were washed with brine, dried Na$_2$SO$_4$, filtered, and concentrated. The dark purple/black solid was loaded onto silica gel and purified by silica gel chromatography (20-50% EtOAc/hexanes) to give (R)-ethyl 3-(5-amino-6-((cyclopropylmethyl)(tetrahydro-2H-pyran-4-yl)amino)pyridin-3-yl)butanoate (0.197 g, 0.545 mmol, 56.3% yield). LCMS m/z calcd for C$_{20}$H$_{31}$N$_3$O$_3$: 361.24. Found: 362.3 (M+H)+.

Preparation of (R)-ethyl 3-(5-((5-chloropyridin-2-yl)amino)-6-((cyclopropylmethyl)(tetrahydro-2H-pyran-4-yl)amino)pyridin-3-yl)butanoate

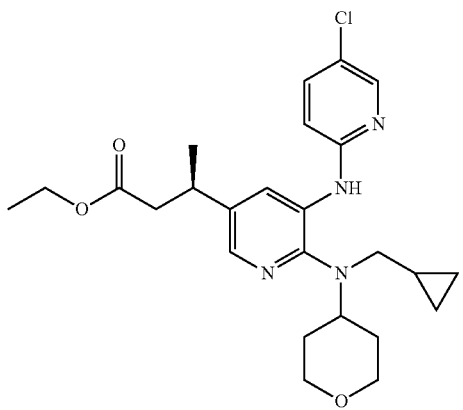 [SMILES: CCOC(=O)C[C@@H](C)c1cnc(N(CC2CC2)C2CCOCC2)c(Nc2ccc(Cl)cn2)c1]

A degassed solution of (R)-ethyl 3-(5-amino-6-((cyclopropylmethyl)(tetrahydro-2H-pyran-4-yl)amino)pyridin-3-yl)butanoate (0.143 g, 0.396 mmol) in toluene (7.91 ml) was treated with 2-bromo-5-chloropyridine (0.084 g, 0.435 mmol), PdOAc$_2$ (1.776 mg, 7.91 μmol), BINAP (0.069 g, 0.111 mmol), and Cs$_2$CO$_3$ (0.232 g, 0.712 mmol). The mixture was purged with nitrogen and then heated at 100° C. for 2 hour. The reaction was cooled and diluted with EtOAc and water. The combine extracts were washed with brine, dried Na$_2$SO$_4$, and concentrated onto silica gel. The residue was purified by silica gel chromatography (0-50% EtOAc/hexanes) to give (R)-ethyl 3-(5-((5-chloropyridin-2-yl)amino)-6-((cyclopropylmethyl)(tetrahydro-2H-pyran-4-yl)amino)pyridin-3-yl)butanoate (0.145 g, 62.7% yield). LCMS m/z calcd for C$_{25}$H$_{33}$ClN$_4$O$_3$: 472.22. Found: 473.2 (M+H)+.

Preparation of (R)-3-(5-((5-chloropyridin-2-yl)amino)-6-((cyclopropylmethyl)(tetrahydro-2H-pyran-4-yl)amino)pyridin-3-yl)butanoic acid

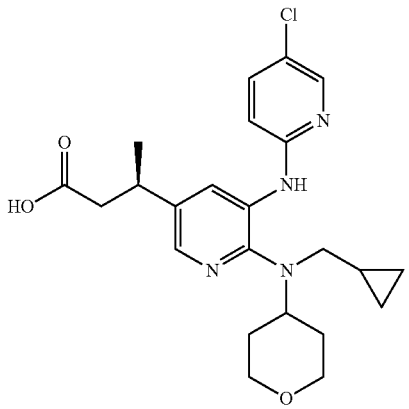 [SMILES: C[C@H](CC(=O)O)c1cnc(N(CC2CC2)C2CCOCC2)c(Nc2ccc(Cl)cn2)c1]

A solution of (R)-ethyl 3-(5-((5-chloropyridin-2-yl)amino)-6-((cyclopropylmethyl) (tetrahydro-2H-pyran-4-yl)amino)pyridin-3-yl)butanoate (0.145 g, 0.307 mmol) was taken up in EtOH (1.5 mL) and treated with 1N NaOH (1.533 ml, 1.533 mmol) and the reaction was heated at 60° C. The solvents were removed under reduced pressure and the residue was taken up in water and extracted with EtOAc. The aqueous was mace acidic pH 5 and extracted with EtOAc. The combined extracts were washed with brine, dried over Na$_2$SO$_4$, filtered, and concentrated onto silica gel. The residue was purified with silica gel chromatography (0-3% MeOH/DCM) to give (R)-3-(5-((5-chloropyridin-2-yl)amino)-6-((cyclopropylmethyl)(tetrahydro-2H-pyran-4-yl)amino)pyridin-3-yl)butanoic acid (0.068 g, 0.153 mmol, 49.9% yield) as a white solid. LCMS m/z calcd for C$_{23}$H$_{29}$ClN$_4$O$_3$: 444.2. Found: 445.4 (M+H)+. $^1$H NMR (400 MHz, CHLOROFORM-d) δ ppm 8.63 (s, 1H) 8.24 (d, J=6.96 Hz, 2H) 7.96 (s, 1H) 7.50 (d, J=8.79 Hz, 1H) 6.69 (d, J=8.79 Hz, 1H) 3.93 (d, J=10.80 Hz, 2H) 3.20-3.41 (m, 4H) 2.87-3.01 (m, 2H) 2.59-2.76 (m, 2H) 1.72 (d, J=11.72 Hz, 2H) 1.46-1.63 (m, 2H) 1.40 (d, J=6.96 Hz, 3H) 1.23-1.32 (m, 1H) 0.58-0.71 (m, 1H) 0.26 (d, J=7.87 Hz, 2H) −0.07 (d, J=4.40 Hz, 2H).

Example 10

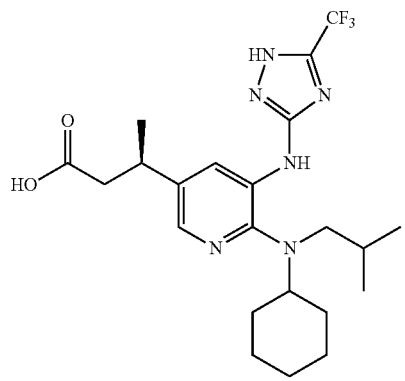 [SMILES: CC(C)CN(c1ncc([C@H](C)CC(=O)O)cc1Nc1n[nH]c(C(F)(F)F)n1)C1CCCCC1]

Preparation of (R)-methyl 3-(6-(cyclohexyl(isobutyl)amino)-5-((5-(trifluoromethyl)-1-((2-(trimethylsilyl)ethoxy)methyl)-1H-1,2,4-triazol-3-yl)amino)pyridin-3-yl)butanoate

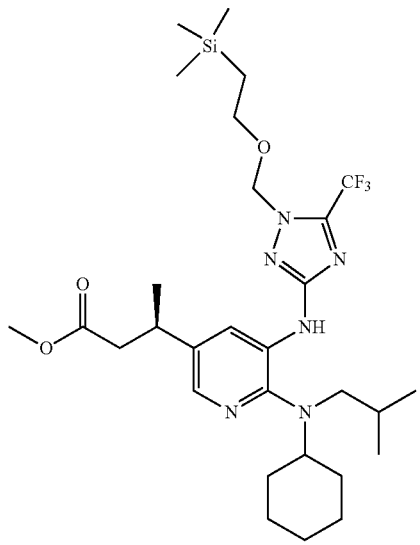 [SMILES: COC(=O)C[C@@H](C)c1cnc(N(CC(C)C)C2CCCCC2)c(Nc2nc(C(F)(F)F)n(COCC[Si](C)(C)C)n2)c1]

A mixture of (R)-methyl 3-(5-amino-6-(cyclohexyl(isobutyl)amino)pyridin-3-yl)butanoate (87 mg, 0.25 mmol) (prepared following a procedure described in Example 3), 3-bromo-5-(trifluoromethyl)-1-((2-(trimethylsilyl)ethoxy)methyl)-1H-1,2,4-triazole (104 mg, 0.300 mmol), Pd$_2$dba$_3$ (45.8 mg, 0.050 mmol), Xantphos (57.9 mg, 0.100 mmol), and cesium carbonate (407 mg, 1.250 mmol) was flushed with nitrogen and then stirred in toluene (3.5 mL) and heated at 100° C. for 6 h. The reaction mixture was filtered through celite, evaporated, and purified by silica gel chromatography (0-30% EtOAc/hexanes) to afford (R)-methyl 3-(6-(cyclohexyl(isobutyl)amino)-5-((5-(trifluoromethyl)-1-((2-(trimethylsilyl)ethoxy)methyl)-1H-1,2,4-triazol-3-yl)amino)pyridin-3-yl)butanoate (130.3 mg, 85%). $^1$H NMR (400 MHz, CDCl$_3$) δ ppm 8.52 (d, J=2.1 Hz, 1H), 8.36 (s, 1H), 7.95 (d, J=2.1 Hz, 1H), 5.46 (s, 2H), 3.57-3.70 (m, 5H), 3.27-3.40 (m, 1H), 2.55-2.74 (m, 3 H), 1.90 (d, J=11.9 Hz, 2H), 1.75 (d, J=12.5 Hz, 2H), 1.60 (s, 3H), 1.28-1.50 (m, 6H), 1.03-1.22 (m, 3H), 0.90-1.00 (m, 2H), 0.84 (d, J=6.6 Hz, 6H), 0.00 (s, 9H).

Preparation of (R)-3-(6-(cyclohexyl(isobutyl)amino)-5-((5-(trifluoromethyl)-1H-1,2,4-triazol-3-yl)amino)pyridin-3-yl)butanoic acid

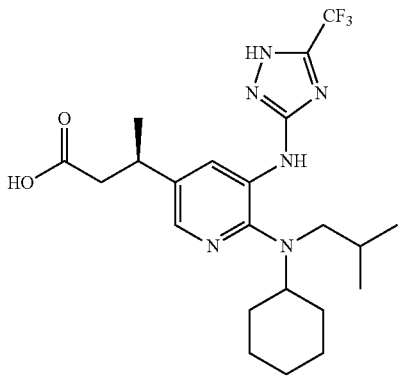 [SMILES: CC(C)CN(c1ncc([C@H](C)CC(=O)O)cc1Nc1n[nH]c(C(F)(F)F)n1)C1CCCCC1]

(R)-methyl 3-(6-(cyclohexyl(isobutyl)amino)-5-((5-(trifluoromethyl)-1-((2-(trimethylsilyl)ethoxy)methyl)-1H-1,2,4-triazol-3-yl)amino)pyridin-3-yl)butanoate (0.130 g, 0.213 mmol) was treated with TFA and then subjected to base hydrolysis as previously described and purified by reverse phase chromatography (10-100% CH$_3$CN/H$_2$O (0.1% formic acid)) to afford the title compound (0.0608 g, 61%) as a white solid.

LCMS (M+H)$^+$: m/z=469.4. $^1$H NMR (400 MHz, CD$_3$OD) δ ppm 8.37 (d, J=2.1 Hz, 1H), 7.89 (d, J=2.1 Hz, 1H), 3.23-3.32 (m, 1H), 2.99 (d, J=7.0 Hz, 2H), 2.72-2.82 (m, 1H), 2.60 (d, J=7.4 Hz, 2H), 1.82 (d, J=11.5 Hz, 2H), 1.73 (d, J=12.5 Hz, 2H), 1.57 (d, J=10.9 Hz, 1H), 1.27-1.47 (m, 6H), 1.04-1.23 (m, 3H), 0.82 (d, J=6.6 Hz, 6H).

Example 11

(R)-3-(6-(cyclohexyl(isobutyl)amino)-5-((3-(trifluoromethyl)-1,2,4-thiadiazol-5-yl)amino)pyridin-3-yl)butanoic acid

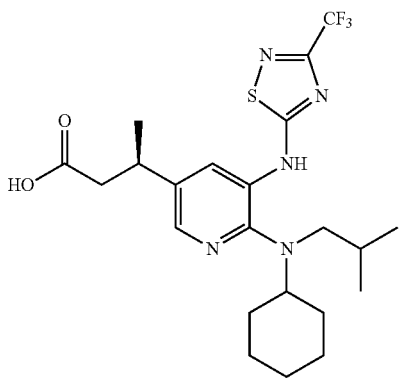 [SMILES: CC(C)CN(c1ncc([C@H](C)CC(=O)O)cc1Nc1nc(C(F)(F)F)ns1)C1CCCCC1]

LCMS calculated for C$_{22}$H$_{30}$F$_3$N$_5$O$_2$S: 485.21, found (M+H)$^+$: m/z=486.34.

$^1$H NMR (400 MHz, METHANOL-d$_4$) δ ppm 8.24 (s, 1H) 8.00 (s, 1H) 3.24 (m, 1H) 3.00 (d, J=6.8 Hz, 2H) 2.82-2.95 (m, 1H) 2.58 (d, J=7.4 Hz, 2H) 1.64-1.84 (m, 4H) 1.50-1.58 (m, 1H) 1.35-1.50 (m, 3H) 1.32 (d, J=7.0 Hz, 3H) 1.02-1.19 (m, 3H) 0.80 (d, J=6.4 Hz, 6H).

Example 12

(R)-3-(5-((3-chloro-1,2,4-thiadiazol-5-yl)amino)-6-(cyclohexyl(isobutyl)amino)pyridin-3-yl)butanoic acid

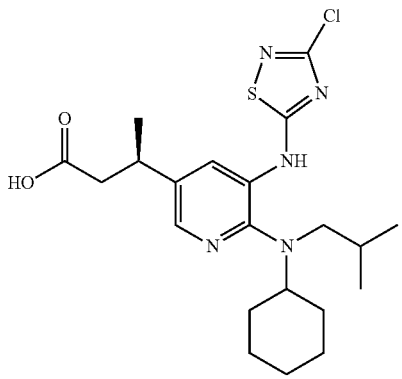 [SMILES: CC(C)CN(c1ncc([C@H](C)CC(=O)O)cc1Nc1nc(Cl)ns1)C1CCCCC1]

This compound was prepared as in Example 1 using 3,5-dichloro-1,2,4-thiadiazole. LCMS calculated for C21H30ClN5O2S: 451.18, found (M+H)+: m/z=452.28.

$^1$H NMR (400 MHz, METHANOL-d$_4$) δ ppm 8.11 (s, 1H) 7.99 (s, 1H) 3.23 (m, 1) 2.99 (d, J=6.8 Hz, 2H) 2.82-2.96 (m, 1H) 2.59 (d, J=7.4 Hz, 2H) 1.73 (t, J=11.4 Hz, 4H) 1.50-1.59 (m, 1H) 1.41 (br. s., 3H) 1.32 (d, J=6.8 Hz, 3H) 0.97-1.23 (m, 3H) 0.80 (d, J=6.6 Hz, 6H).

Example 13

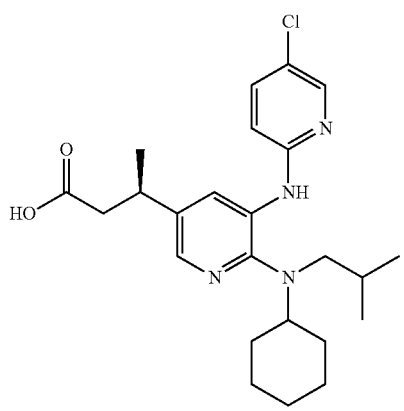 [SMILES: CC(C)CN(c1ncc([C@H](C)CC(=O)O)cc1Nc1ccc(Cl)cn1)C1CCCCC1]

Preparation of (R)-ethyl 3-(5-((5-chloropyridin-2-yl)amino)-6-(cyclohexyl(isobutyl)amino)pyridin-3-yl)butanoate

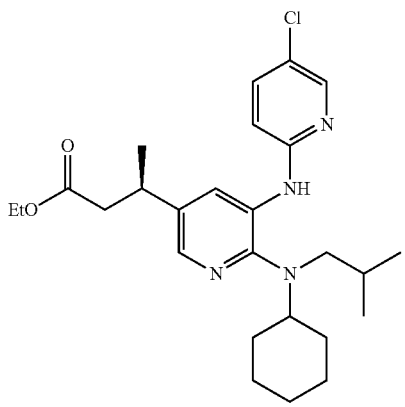 [SMILES: CC(C)CN(c1ncc([C@H](C)CC(=O)O)cc1Nc1ccc(Cl)cn1)C1CCCCC1]

A degassed solution of ethyl (R)-3-(5-amino-6-(cyclohexyl(isobutyl)amino)pyridin-3-yl)butanoate (80 mg, 0.221 mmol) in toluene (4426 μl) was treated with 2-bromo-5-chloropyridine (51.1 mg, 0.266 mmol), PdOAc$_2$ (9.94 mg, 0.044 mmol), rac-BINAP (38.6 mg, 0.062 mmol), and Cs$_2$CO$_3$ (130 mg, 0.398 mmol). The mixture was bubbled with N$_2$ for 5 min, and then stirred at 100° C. for 2 hours. The reaction was cooled to rt, combined with another batch reaction (0.119 mmol scale), diluted with EtOAc, and filtered through a pad of celite. The filtrate was washed with water, Brine, dried over Na$_2$SO$_4$, filtered, and concentrated. Purification with column chromatography (0-40% EtOAc/Hexane) afforded (R)-ethyl 3-(5-((5-chloropyridin-2-yl)amino)-6-(cyclohexyl(isobutyl)amino)pyridin-3-yl)butanoate (124 mg, 0.262 mmol, 77% yield) as clear oil. $^1$H NMR (400 MHz, CHLOROFORM-d) δ ppm 8.48 (br. s., 1H), 8.23 (d, J=2.2 Hz, 1H), 7.88 (s, 1H), 7.70 (br. s., 1H), 7.49 (dd, J=2.5, 8.7 Hz, 1H), 6.68 (d, J=8.6 Hz, 1H), 4.11 (q, J=7.1 Hz, 2H), 3.37-3.22 (m, 1H), 3.02 (d, J=6.6 Hz, 2H), 2.81-2.51 (m, 3H), 1.87-1.69 (m, 4H), 1.68-1.52 (m, 1H), 1.49-1.31 (m, 6H), 1.20 (t, J=7.1 Hz, 3H), 1.16-1.02 (m, 3H), 0.85 (d, J=6.6 Hz, 6H). LCMS (ESI) m/z calcd for C$_{26}$H$_{37}$ClN$_4$O$_2$: 472.26. Found: 473.5 (M+1).

Preparation of (R)-3-(5-((5-chloropyridin-2-yl)amino)-6-(cyclohexyl(isobutyl)amino)pyridin-3-yl)butanoic acid

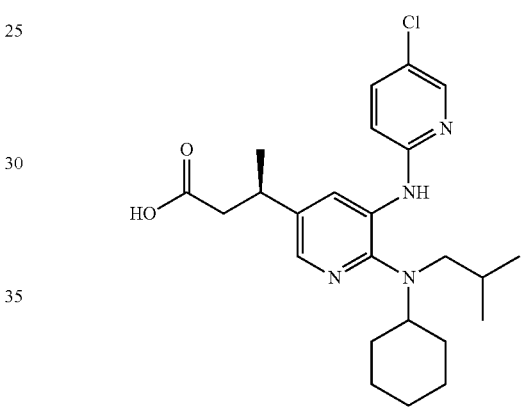

A solution of (R)-ethyl 3-(5-((5-chloropyridin-2-yl)amino)-6-(cyclohexyl(isobutyl)amino)pyridin-3-yl)butanoate (122 mg, 0.258 mmol) in Tetrahydrofuran (THF) (3.9 mL) and Ethanol (1.300 mL) was treated with 2M LiOH (1.290 mL, 2.58 mmol) and stirred at rt for 18 hours. The reaction was diluted with 1N HCl, extracted with EtOAc, washed with Brine, dried over Na$_2$SO$_4$, filtered, and concentrated. Purification with reverse phase HPLC (30-100% MeCN-0.1% formic acid/H2O-0.1% formic acid) afforded (R)-3-(5-((5-chloropyridin-2-yl)amino)-6-(cyclohexyl(isobutyl)amino)pyridin-3-yl)butanoic acid (57.8 mg, 0.126 mmol, 48.9% yield, 97% purity) as white solid. $^1$H NMR (400 MHz, CHLOROFORM-d) δ ppm 8.50 (s, 1H), 8.23 (d, J=2.4 Hz, 1H), 7.91 (s, 1H), 7.71 (s, 1H), 7.49 (dd, J=2.5, 8.7 Hz, 1H), 6.67 (d, J=8.8 Hz, 1H), 3.41-3.22 (m, 1H), 3.01 (d, J=7.0 Hz, 2H), 2.79-2.59 (m, 3H), 1.89-1.68 (m, 4H), 1.57 (d, J=9.3 Hz, 1H), 1.50-1.33 (m, 6H), 1.19-0.99 (m, 3H), 0.85 (d, J=6.6 Hz, 6H). LCMS (ESI) m/z calcd for C$_{24}$H$_{33}$ClN$_4$O$_2$: 444.23. Found: 445.4 (M+1)+, 443.4 (M−1).

Example 14

(R)-3-(6-(cyclohexyl(isobutyl)amino)-5-((3-isopropyl-1,2,4-thiadiazol-5-yl)amino)pyridin-3-yl)butanoic acid

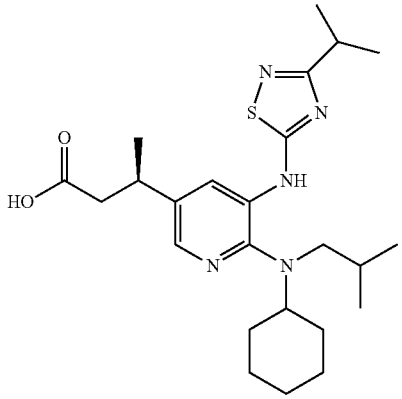 [SMILES: CC(C)CN(c1ncc([C@H](C)CC(=O)O)cc1Nc1nc(C(C)C)ns1)C1CCCCC1]

LCMS calculated for $C_{24}H_{37}N_5O_2S$: 459.27, found (M+H)$^+$: m/z=460.43

$^1$H NMR (400 MHz, METHANOL-d$_4$) δ ppm 8.27 (s, 1H) 7.95 (s, 1H) 3.05 (dt, J=13.8, 7.0 Hz, 1H) 2.99 (d, J=6.8 Hz, 2H) 2.83 (m, 1H) 2.59 (d, J=7.4 Hz, 2H) 1.63-1.86 (m, 4H) 1.54 (m., 1H) 1.35-1.48 (m, 4H) 1.30-1.35 (m, 9H) 0.98-1.19 (m, 3H) 0.81 (d, J=6.6 Hz, 6H).

Example 15

(R)-3-(6-(cyclohexyl(isobutyl)amino)-5-((3-(methoxymethyl)-1,2,4-thiadiazol-5-yl)amino)pyridin-3-yl)butanoic acid

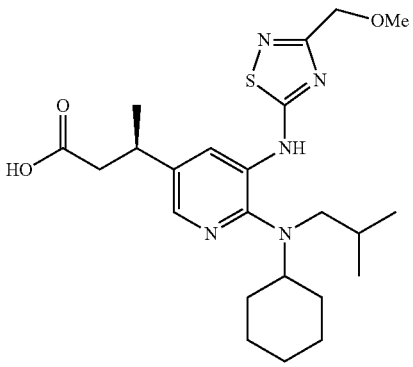 [SMILES: COCc1nsc(Nc2cc([C@H](C)CC(=O)O)cnc2N(CC(C)C)C2CCCCC2)n1]

LCMS calculated for $C_{23}H_{35}N_5O_3S$: 461.25, found (M+H)$^+$: m/z=462.42

$^1$H NMR (400 MHz, METHANOL-d$_4$) δ ppm 8.19 (s, 1H) 8.00 (s, 1H) 4.52 (s, 2H) 3.48 (s, 3H) 3.03 (d, J=6.8 Hz, 2H) 2.82-2.96 (m, 1H) 2.63 (d, J=7.5 Hz, 2H) 1.66-1.89 (m, 4H) 1.52-1.63 (m, 1H) 1.44 (m, 4H) 1.36 (d, J=7.0 Hz, 3H) 1.02-1.21 (m, 3H) 0.84 (d, J=6.4 Hz, 6H).

Example 16

(R)-3-(6-(cyclohexyl(isobutyl)amino)-5-((3-methyl-1,2,4-thiadiazol-5-yl)amino)pyridin-3-yl)butanoic acid

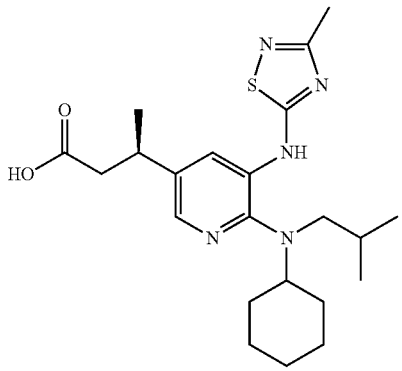 [SMILES: Cc1nsc(Nc2cc([C@H](C)CC(=O)O)cnc2N(CC(C)C)C2CCCCC2)n1]

LCMS calculated for $C_{22}H_{33}N_5O_2S$: 431.24, found (M+H)$^+$: m/z=432.35

$^1$H NMR (400 MHz, METHANOL-d$_4$) δ ppm 8.10 (d, J=1.8 Hz, 1H) 8.00 (d, J=1.8 Hz, 1H) 3.02 (d, J=7.0 Hz, 2H) 2.89 (m, 1H) 2.63 d, J=7.5 Hz, 2H) 2.44 (s, 3H) 1.66-1.88 (m, 4H) 1.57 (m., 1H) 1.38-1.51 (m, 3H) 1.36 (d, J=7.1 Hz, 3H) 1.03-1.19 (m, 3H) 0.84 (d, J=6.6 Hz, 6H).

Example 17

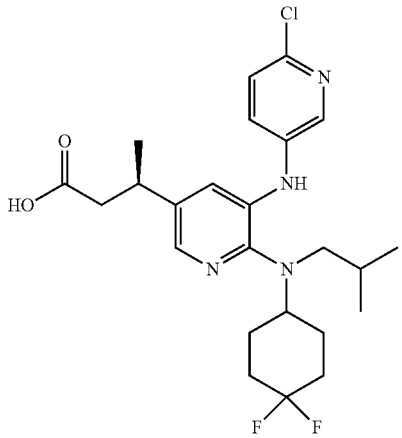 [SMILES: CC(C)CN(c1ncc([C@H](C)CC(=O)O)cc1Nc1ccc(Cl)nc1)C1CCC(F)(F)CC1]

Preparation of 4,4-difluoro-N-isobutylcyclohexanamine

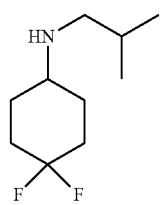

To a stirring mixture of 4,4-difluorocyclohexanamine, hydrochloride (5 g, 29 mmol) and sodium bicarbonate (9.79 g, 117 mmol) in dichloromethane (DCM) (40 mL) and methanol (40.0 mL) was added isobutyraldehyde (2.71 mL, 29.1 mmol). The mixture was stirred at room temperature overnight. The mixture was cooled to 0° C. before sodium borohydride (1.21 g, 32.0 mmol) was added portionwise. The mixture was allowed to warm to room temperature, stirred for 3 hours, quenched with water and extracted 3 times with dichloromethane. The combined organic layers were washed with brine, dried over sodium sulfate and concentrated to give 4,4-difluoro-N-isobutylcyclohexanamine (5.1 g, 26.7 mmol, 92% yield) as a liquid. $^1$H NMR (400 MHz, CHLOROFORM-d) δ ppm 2.5-2.7 (m, 1H), 2.4 (d, J=6.8 Hz, 2H), 2.0-2.2 (m, 2H), 1.6-2.0 (m, 6H), 1.4-1.6 (m, 2H), 0.9 (d, J=6.6 Hz, 6H).

Preparation of 5-bromo-N-(4,4-difluorocyclohexyl)-N-isobutl-3-nitropyridin-2-amine

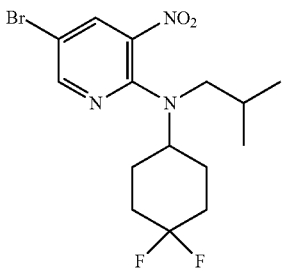 [SMILES: CC(C)CN(c1ncc(Br)cc1[N+](=O)[O-])C1CCC(F)(F)CC1]

A mixture of 5-bromo-2-chloro-3-nitropyridine (2.334 g, 9.83 mmol), N-ethyl-N-isopropylpropan-2-amine (3.42 mL, 19.66 mmol), and 4,4-difluoro-N-isobutylcyclohexanamine (1.88 g, 9.83 mmol) in N,N-dimethylformamide (DMF) (20 mL) was heated at 70° C. for 48 hours. The reaction seemed to progress steadily each day. The mixture as allowed to cool to room temperature, quenched with water, and extracted 3 times with ethyl acetate. The combined organic layers were washed with brine, washed with 5% lithium chloride, dried over sodium sulfate, and concentrated. The residue was purified by silica chromatography eluting with a gradient of 0% to 40% dichloromethane in hexanes. Fractions were concentrated to give 5-bromo-N-(4,4-difluorocyclohexyl)-N-isobutyl-3-nitropyridin-2-amine (1.13 g, 2.88 mmol, 29.3% yield, 93% purity) as a yellow solid. LCMS (ESI) m/z calculated for $C_{15}H_{20}BrF_2N_3O_2$: 391.1, 393.1. Found: 392.2, 394.3 (M+H)$^+$.

Alternatively, 5-bromo-N-(4,4-difluorocyclohexyl)-N-isobutyl-3-nitropyridin-2-amine was obtained as follows:

5-bromo-2-fluoro-3-nitropyridine (1.85 g, 8.37 mmol), 4,4-difluoro-N-isobutylcyclohexanamine (1.6 g, 8.4 mmol), and N,N-diisopropylethylamine (2.92 mL, 16.7 mmol) in acetonitrile (27 mL) were heated at 60° C. overnight. The mixture was concentrated and the residue purified by silica chromatography eluting with a gradient of 0% to 40% of dichloromethane in hexanes. Fractions were concentrated to give 5-bromo-N-(4,4-difluorocyclohexyl)-N-isobutyl-3-nitropyridin-2-amine (1.8 g, 4.6 mmol, 55% yield, 93% purity) as a pale yellow solid. LCMS (ESI) m/z calculated for $C_{15}H_{20}BrF_2N_3O_2$: 391.1, 393.1. Found: 392.2, 394.2 (M+H)$^+$.

Preparation of (E)-ethyl 3-(6-((4,4-difluorocyclohexyl)(isobutyl)amino)-5-nitropyridin-3-yl)but-2-enoate

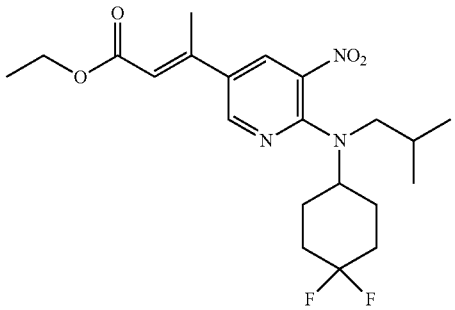 [SMILES: CCOC(=O)/C=C(\C)c1cnc(N(CC(C)C)C2CCC(F)(F)CC2)c([N+](=O)[O-])c1]

A mixture of 5-bromo-N-(4,4-difluorocyclohexyl)-N-isobutyl-3-nitropyridin-2-amine (1.3 g, 3.3 mmol), potassium carbonate (1.37 g, 9.94 mmol), ethyl crotonate (2.49 mL, 19.9 mmol), and PdCl$_2$(dppf)-CH$_2$Cl$_2$ adduct (0.271 g, 0.331 mmol) in N,N-dimethylformamide (DMF) (20 mL) were purged with nitrogen for 5 minutes. The reaction vial was capped with a septum cap before being placed into a heating block that was preheated to 110° C. The mixture was heated for 2 hours, cooled to room temperature, diluted with water, and extracted 3 times with ethyl acetate. The combined organic layers were washed with brine, dried over sodium sulfate, and concentrated. The residue was purified by reverse phase medium pressure chromatography (10-100% MeCN/water/0.1% formic acid). Fractions were concentrated to give impure material. The material was purified by silica chromatography eluting with a gradient of 0% to 15% ethyl acetate in hexanes. Fractions were concentrated to give (E)-ethyl 3-(6-((4,4-difluorocyclohexyl)(isobutyl) amino)-5-nitropyridin-3-yl)but-2-enoate (690 mg, 1.62 mmol, 48.9% yield, 95% purity). LCMS (ESI) m/z calculated for $C_{21}H_{29}F_2N_3O_4$: 425.2. Found: 426.3 (M+H)$^+$.

Alternatively, (E)-ethyl 3-(6-((4,4-difluorocyclohexyl) (isobutyl)amino)-5-nitropyridin-3-yl)but-2-enoate was obtained as follows:

5-bromo-N-(4,4-difluorocyclohexyl)-N-isobutyl-3-nitropyridin-2-amine (1.55 g, 3.95 mmol), (E)-ethyl 3-(4,4,5,5-tetramethyl-1,3,2-dioxaborolan-2-yl)but-2-enoate (1.42 g, 5.93 mmol), 2M sodium carbonate (5.93 mL, 11.9 mmol), and tetrakis(triphenylphosphine)palladium(0) (0.228 g, 0.198 mmol) in N,N-dimethylformamide (DMF) (20 mL) were degassed with nitrogen for 5 minutes before the reaction vessel was submerged into an oil bath that was preheated to 100° C. After 20 minutes, the reaction temperature was increased to 110° C. The mixture was stirred for 3 hours and allowed to cool to room temperature. The mixture was quenched with water and extracted 2 times with ethyl acetate. The combined organic layers were washed with brine, dried over sodium sulfate, and concentrated. The residue was purified by silica chromatography eluting with a gradient of 0% to 20% ethyl acetate in hexanes. Fractions were concentrated to give (E)-ethyl 3-(6-((4,4-difluorocyclohexyl)(isobutyl)amino)-5-nitropyridin-3-yl)but-2-enoate (1.17 g, 2.75 mmol, 69.6% yield). LCMS (ESI) m/z calculated for $C_{21}H_{29}F_2N_3O_4$: 425.2. Found: 426.3 (M+H)$^+$.

Preparation of (R)-ethyl 3-(6-((4,4-difluorocyclohexyl)(isobutyl)amino)-5-nitropyridin-3-yl)butanoate

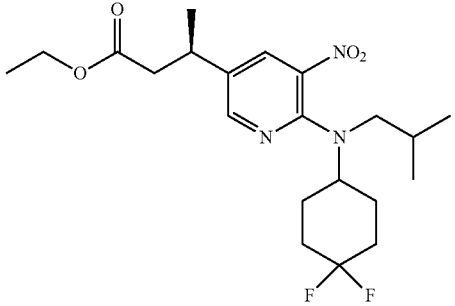 [SMILES: CCOC(=O)C[C@@H](C)c1cnc(N(CC(C)C)C2CCC(F)(F)CC2)c([N+](=O)[O-])c1]

A stir bar, NiBr₂ (DME) (19.4 mg, 0.063 mmol), and (S)-MeDuPhos (23.2 mg, 0.076 mmol) were added to septum-capped reaction vial. The reaction vial was purged with nitrogen. Isopropanol (2.5 mL) was added and the mixture stirred for 10 minutes. Triethylamine (0.439 mL, 3.15 mmol), formic acid (0.302 mL, 7.87 mmol), and a suspension of (E)-ethyl 3-(6-((4,4-difluorocyclohexyl)(isobutyl) amino)-5-nitropyridin-3-yl)but-2-enoate (670 mg, 1.575 mmol) in isopropanol (12.5 mL) were then added sequentially under nitrogen. The reaction vial was placed in a heating block that was preheated to 80° C. Solids dissolved within 2 minutes to give an orange solution. The mixture was heated for 16 hours. The mixture was stirred at 80° C. under a blanket of nitrogen an additional 6 hours. The mixture was allowed to cool to room temperature and was concentrated. The residue was purified by silica chromatography eluting with a gradient or of 0% to 20% ethyl acetate in hexanes. Fractions were concentrated to give (R)-ethyl 3-(6-((4,4-difluorocyclohexyl)(isobutyl)amino)-5-nitropyridin-3-yl)butanoate (240 mg, 0.561 mmol, 35.7% yield as an orange oil. LCMS (ESI) m/z calculated for $C_{21}H_{31}F_2N_3O_4$: 427.2. Found: 428.4 $(M+H)^+$.

Alternatively, ethyl (R)-3-(6-((4,4-difluorocyclohexyl) (isobutyl)amino)-5-nitropyridin-3-yl)butanoate was obtained as follows:

A nitrogen-filled round bottom flask was equipped with a stir bar and charged with $[Ph_3PCuH]_6$ (0.254 g, 0.129 mmol) and (R,S)—PPF—P(tBu)₂ (0.252 g, 0.465 mmol). The septum-capped round bottom was purged with nitrogen for an additional 5 minutes before 5.2 mL of anhydrous toluene was added. The mixture was cooled to 0° C. in an ice bath before poly(methylhydrosiloxane) (0.369 mL, 2.59 mmol) and tert-butanol (0.297 mL, 3.10 mmol) were added. The mixture was stirred for 5 minutes and transferred via syringe to a 0° C. stirring mixture of ethyl (E)-3-(6-((4,4-difluorocyclohexyl)(isobutyl)amino)-5-nitropyridin-3-yl)but-2-enoate (1.1 g, 2.59 mmol) in 5.2 mL of anhydrous toluene. After 30 minutes, the mixture was allowed to warm to room temperature and stirred overnight. The mixture was concentrated and the residue purified by silica chromatography eluting with a gradient of 0% to 20% ethyl acetate in hexanes. Fractions were concentrated to give ethyl (R)-3-(6-((4,4-difluorocyclohexyl)(isobutyl)amino)-5-nitropyridin-3-yl)butanoate (756 mg, 1.77 mmol, 68.4% yield). LCMS (ESI) m/z calculated for $C_{21}H_{31}F_2N_3O_4$: 427.2. Found: 428.4 $(M+H)^+$.

Preparation of (R)-ethyl 3-(5-amino-6-((4,4-difluorocyclohexyl)(isobutyl)amino)pyridin-3-yl)butanoate

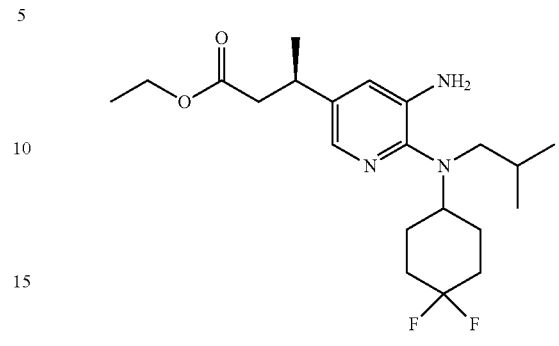

A mixture of ethyl (R)-3-(6-((4,4-difluorocyclohexyl) (isobutyl)amino)-5-nitropyridin-3-yl)butanoate (756 mg, 1.77 mmol) and ammonium chloride (1890 mg, 35.4 mmol) in ethanol (10 mL) and water (6.67 mL) was cooled to 0° C. before zinc (1156 mg, 17.68 mmol) was added in 1 portion. The mixture was stirred at 0° C. for 5 minutes and then allowed to warm to room temperature and stirred for 4 hours. Additional zinc (1156 mg, 17.68 mmol) was added and the mixture stirred for 3 hours. The zinc was filtered off over a cotton plug and the plug washed with ethanol. The filtrate was concentrated to remove excess ethanol. The remaining aqueous mixture was diluted with brine and extracted 2 times with ethyl acetate. The combined organic layers were washed with brine, dried over sodium sulfate, and concentrated. The residue was purified by silica chromatography eluting with a gradient of 0% to 70% ethyl acetate in hexanes. Fractions were concentrated to give ethyl (R)-3-(5-amino-6-((4,4-difluorocyclohexyl)(isobutyl) amino)pyridin-3-yl)butanoate (510 mg, 1.28 mmol, 72.5% yield) as a pale tan solid. LCMS (ESI) m/z calculated for $C_{21}H_{33}F_2N_3O_2$: 397.3. Found: 398.4 $(M+H)^+$.

Preparation of (R)-ethyl 3-(5-((6-chloropyridin-3-yl)amino)-6-((4,4-difluorocyclohexyl)(isobutyl)amino)pyridin-3-yl)butanoate

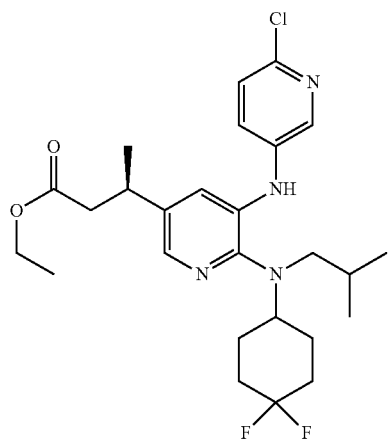 [SMILES: CCOC(=O)C[C@@H](C)c1cnc(N(CC(C)C)C2CCC(F)(F)CC2)c(Nc2ccc(Cl)nc2)c1]

(R)-Ethyl 3-(5-amino-6-((4,4-difluorocyclohexyl)(isobutyl)amino)pyridin-3-yl)butanoate (39 mg, 0.098 mmol), 5-bromo-2-chloropyridine (22.7 mg, 0.118 mmol), potassium carbonate (67.8 mg, 0.491 mmol), tris(dibenzylideneacetone)dipalladium(0) (18 mg, 0.020 mmol), and Xantphos (22.7 mg, 0.039 mmol) were placed in a septum-capped reaction vial and thoroughly purged with nitrogen. Toluene (1 mL) was added and the mixture heated at 100° C. for 3 hours. The mixture was allowed to cool to room temperature, quenched with brine, and extracted 2 times with ethyl acetate. The combined organic layers were washed with brine, dried over sodium sulfate, and concentrated. The residue was purified by silica chromatography eluting with a gradient of 0% to 50% ethyl acetate in hexanes. Fractions were concentrated to give (R)-ethyl 3-(5-((6-chloropyridin-3-yl)amino)-6-((4,4-difluorocyclohexyl)(isobutyl)amino)pyridin-3-yl)butanoate (31 mg, 0.061 mmol, 62% yield). LCMS (ESI) m/z calculated for $C_{26}H_{35}ClF_2N_4O_2$: 508.2. Found: 509.4 $(M+H)^+$.

Preparation of (R)-3-(5-((6-chloropyridin-3-yl)amino)-6-((4,4-difluorocyclohexyl)(isobutyl)amino)pyridin-3-yl)butanoic acid

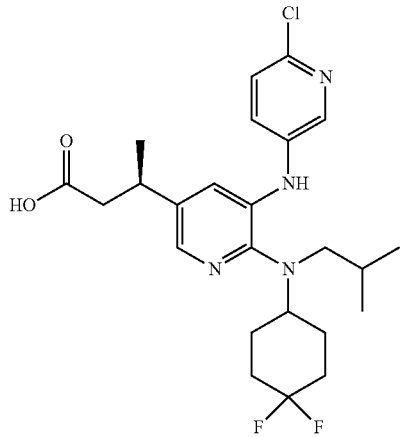 [SMILES: CC(C)CN(c1ncc([C@H](C)CC(=O)O)cc1Nc1ccc(Cl)nc1)C1CCC(F)(F)CC1]

1M Sodium hydroxide (0.570 mL, 0.570 mmol) was added to a solution of (R)-ethyl 3-(5-((6-chloropyridin-3-yl)amino)-6-((4,4-difluorocyclohexyl)(isobutyl)amino)pyridin-3-yl)butanoate (29 mg, 0.057 mmol) in ethanol (1 mL) and the mixture stirred at 60° C. for 1 hour before being cooled to room temperature, quenched with 1M citric acid, and extracted 2 times with dichloromethane. The combined organic layers were washed with brine, dried over sodium sulfate, and concentrated. The residue was purified by reverse phase HPLC. Fractions were concentrated and the residue lyophilized to give (R)-3-(5-((6-chloropyridin-3-yl)amino)-6-((4,4-difluorocyclohexyl)(isobutyl)amino)pyridin-3-yl)butanoic acid (3.2 mg, 6.6 μmol, 12% yield) as a white powder. LCMS (ESI) m/z calculated for $C_{24}H_{31}ClF_2N_4O_2$: 480.2. Found: 481.3 $(M+H)^+$. $^1$H NMR (400 MHz, METHANOL-$d_4$) δ ppm 8.0 (d, J=2.9 Hz, 1H), 7.9 (d, J=2.0 Hz, 1H), 7.4-7.5 (m, 2H), 7.3 (d, J=8.8 Hz, 1H), 3.1-3.2 (m, 2H), 3.0 (d, J=6.8 Hz, 2H), 2.5-2.6 (m, 2H), 1.9-2.1 (m, 2H), 1.5-1.8 (m, 6H), 1.4 (m, 1H), 1.3 (d, J=7.0 Hz, 3H), 0.8 (d, J=6.6 Hz, 6H).

Example 18

(R)-3-(5-((5-chloropyridin-2-yl)amino)-6-((4,4-difluorocyclohexyl) (isobutyl)amino)pyridin-3-yl)butanoic acid

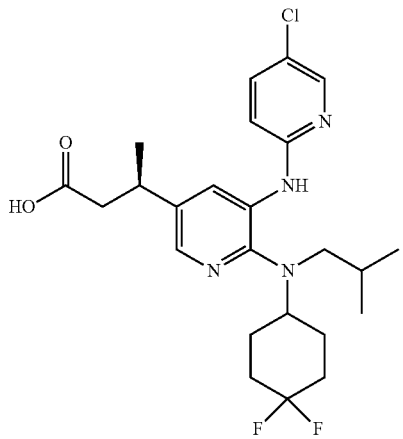 [SMILES: CC(C)CN(c1ncc([C@H](C)CC(=O)O)cc1Nc1ccc(Cl)cn1)C1CCC(F)(F)CC1]

Potassium carbonate (46.9 mg, 0.340 mmol), tris(dibenzylideneacetone)dipalladium(0) (20.7 mg, 0.023 mmol), 2-bromo-5-chloropyridine (43.6 mg, 0.226 mmol), and Xantphos (26.2 mg, 0.045 mmol) were placed in a reaction vial equipped with a stir bar and purged with nitrogen. (R)-ethyl 3-(5-amino-6-((4,4-difluorocyclohexyl)(isobutyl)amino)pyridin-3-yl)butanoate (45 mg, 0.113 mmol) was dissolved in toluene (1.1 mL). This mixture was purged with a stream of nitrogen for 2 minutes. The toluene solution was added to the potassium carbonate mixture via syringe. The combined reaction mixture was placed into a heating block that was preheated to 100° C. The mixture was heated overnight. The mixture was allowed to cool to room temperature, quenched with water, and extracted 2 times with ethyl acetate. The combined organic layers were washed with brine, dried over sodium sulfate, and concentrated. The residue was purified by reverse phase medium pressure chromatography. Fractions were concentrated to give (R)-ethyl 3-(5-((5-chloropyridin-2-yl)amino)-6-((4,4-difluorocyclohexyl)(isobutyl)amino)pyridin-3-yl)butanoate (4 mg, 7.86 μmol, 6.94% yield). 1M Sodium hydroxide (0.079 mL, 0.079 mmol) was added to a solution of (R)-ethyl 3-(5-((5-chloropyridin-2-yl)amino)-6-((4,4-difluorocyclohexyl)(isobutyl)amino)pyridin-3-yl)butanoate (4 mg, 7.86 μmol) in ethanol (0.5 mL) and the mixture stirred at 50° C. for 1 hour, cooled to room temperature, quenched with 1 mL of 1M HCl, and concentrated. The residue was purified by reverse phase medium pressure chromatography. Fractions were concentrated and the residue lyophilized to give (R)-3-(5-((5-chloropyridin-2-yl)amino)-6-((4,4-difluorocyclohexyl)(isobutyl)amino)pyridin-3-yl)butanoic acid (3.6 mg, 7.48 μmol, 95% yield) as a white solid. LCMS (ESI) m/z calculated for $C_{24}H_{31}ClF_2N_4O_2$: 480.2. Found: 481.4 $(M+H)^+$. $^1$H NMR (400 MHz, METHANOL-$d_4$) δ ppm 8.4 (d, J=2.0 Hz, 1H), 8.2 (d, J=2.3 Hz, 1H), 7.9 (d, J=2.1 Hz, 1H), 7.6-7.6 (m, 1H), 6.9 (d, J=9.0 Hz, 1H), 2.9-3.1 (m, 4H), 2.6 (d, J=7.6 Hz, 2H), 2.0 (d, J=4.1 Hz, 2H), 1.8 (m, 2H), 1.5-1.8 (m, 4H), 1.3-1.4 (m, 1H), 1.3 (d, J=7.0 Hz, 3H), 0.8 (d, J=6.6 Hz, 6H).

Example 19

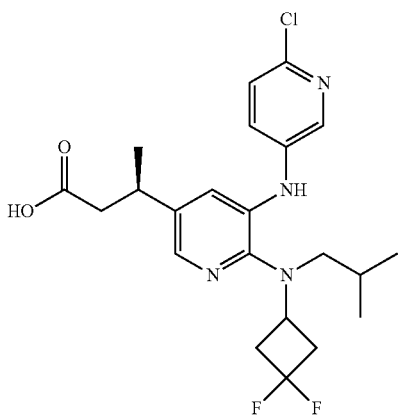 [SMILES: CC(C)CN(c1ncc([C@H](C)CC(=O)O)cc1Nc1ccc(Cl)nc1)C1CC(F)(F)C1]

Preparation of
3,3-difluoro-N-isobutylcyclobutanamine

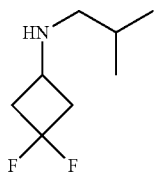

To a stirring mixture of 3,3-difluorocyclobutanamine hydrochloride (3.0 g, 21 mmol) and sodium bicarbonate (7.0 g, 84 mmol) in dichloromethane (DCM) (30 mL) and methanol (30.0 mL) was added isobutyraldehyde (1.91 mL, 20.9 mmol). The mixture was stirred at room temperature overnight. The mixture was cooled to 0° C. before sodium borohydride (0.791 g, 20.9 mmol) was added portionwise. The mixture was allowed to warm to room temperature, stirred for 3 hours, quenched with water and extracted 3 times with dichloromethane. The combined organic layers were washed with brine, dried over sodium sulfate and concentrated to give 3,3-difluoro-N-isobutylcyclobutanamine (2.68 g, 16.42 mmol, 79% yield). $^1$H NMR (400 MHz, CHLOROFORM-d) δ ppm 3.1-3.3 (m, 1H), 2.7-2.9 (m, 2H), 2.3 (d, J=6.8 Hz, 2H), 2.2-2.3 (m, 2H), 1.6-1.8 (m, 1H), 1.1-1.4 (m, 1H), 0.9 (d, J=6.6 Hz, 6H).

Preparation of 5-bromo-N-(3,3-difluorocyclobutyl)-N-isobutyl-3-nitropyridin-2-amine

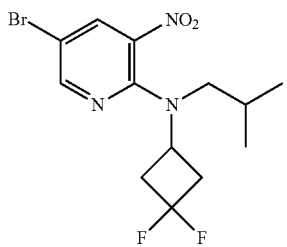 [SMILES: CC(C)CN(c1ncc(Br)cc1[N+](=O)[O-])C1CC(F)(F)C1]

A mixture of 5-bromo-2-chloro-3-nitropyridine (3.90 g, 16.4 mmol), N-ethyl-N-isopropylpropan-2-amine (5.72 mL, 32.8 mmol), and 3,3-difluoro-N-isobutylcyclobutanamine (2.68 g, 16.4 mmol) in N-methyl-2-pyrrolidone (NMP) (20 mL) was heated at 80° C. for 16 hours. The mixture was allowed to cool to room temperature, quenched with brine, and extracted 2 times with ethyl acetate. The combined organic layers were washed with brine, dried over sodium sulfate, and concentrated. The residue was purified by silica chromatography eluting with a gradient of 0% to 30% ethyl acetate in hexanes. Fractions were concentrated to give 5-bromo-N-(3,3-difluorocyclobutyl)-N-isobutyl-3-nitropyridin-2-amine (3.19 g, 8.76 mmol, 53% yield) as a yellow solid. LCMS (ESI) m/z calculated for $C_{13}H_{16}BrF_2N_3O_2$: 363.0, 365.0. Found: 364.2, 366.2 (M+H)$^+$.

Preparation of (E)-ethyl 3-(6-((3,3-difluorocyclobutyl)(isobutyl)amino)-5-nitropyridin-3-yl)but-2-enoate

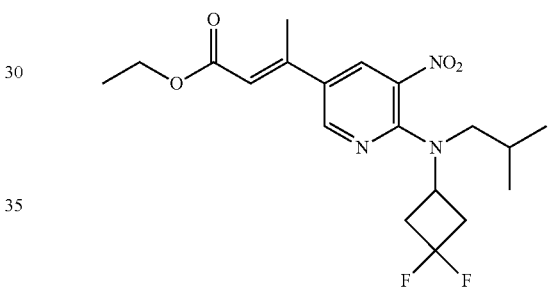

A mixture of 5-bromo-N-(3,3-difluorocyclobutyl)-N-isobutyl-3-nitropyridin-2-amine (3.18 g, 8.73 mmol), potassium carbonate (3.62 g, 26.2 mmol), ethyl crotonate (6.57 mL, 52.4 mmol), and PdCl$_2$(dppf)-CH$_2$Cl$_2$ adduct (0.713 g, 0.873 mmol) in N,N-dimethylformamide (DMF) (80 mL) were purged with nitrogen for 5 minutes. The reaction flask was capped with a septum before being placed into a heating block that was preheated to 110° C. The mixture was heated for 2 hours, cooled to room temperature, diluted with water, and extracted 3 times with ethyl acetate. The combined organic layers were washed with brine, dried over sodium sulfate, and concentrated. The residue was purified by silica chromatography eluting with a gradient of 0% to 20% ethyl acetate in hexanes. Fractions were concentrated. The residue was further purified by medium pressure reverse phase chromatography (10%-100% AcCN/Water/0.1% formic acid). Fractions were concentrated to give (E)-ethyl 3-(6-((3,3-difluorocyclobutyl)(isobutyl)amino)-5-nitropyridin-3-yl)but-2-enoate (1.25 g, 3.15 mmol, 36% yield). LCMS (ESI) m/z calculated for $C_{19}H_{25}F_2N_3O_4$: 397.2. Found: 398.3 (M+H)$^+$.

Preparation of (E)-ethyl 3-(5-amino-6-((3,3-difluorocyclobutyl) (isobutyl)amino)pyridin-3-yl)but-2-enoate

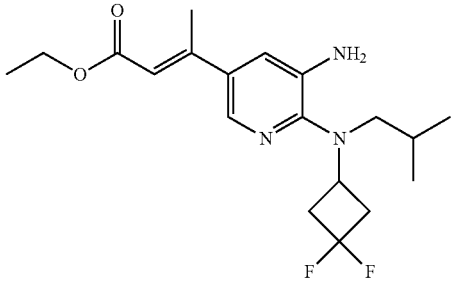 [SMILES: CCOC(=O)/C=C(\C)c1cnc(N(CC(C)C)C2CC(F)(F)C2)c(N)c1]

(E)-Ethyl 3-(6-((3,3-difluorocyclobutyl)(isobutyl)amino)-5-nitropyridin-3-yl)but-2-enoate (100 mg, 0.252 mmol) was dissolved in ethanol (1.5 mL) and then a solution of ammonia hydrochloride (269 mg, 5.03 mmol) in water (1 mL) was added. The mixture was cooled to 0° C. and zinc (165 mg, 2.52 mmol) added. The mixture was allowed to warm to room temperature and stirred for 3 hours. The mixture was filtered through a cotton plug and the filter cake washed with ethanol to remove zinc. The ethanol was removed under reduced pressure and the residue diluted with water and ethyl acetate. The mixture was extracted 2 times with ethyl acetate. The combined organic layers were dried over sodium sulfate and concentrated. The residue was purified by silica chromatography eluting with a gradient of 0% to 50% ethyl acetate in hexanes. Fractions were concentrated to give (E)-ethyl 3-(5-amino-6-((3,3-difluorocyclobutyl)(isobutyl)amino)pyridin-3-yl)but-2-enoate (88 mg, 0.239 mmol, 95% yield). LCMS (ESI) m/z calculated for $C_{19}H_{27}F_2N_3O_2$: 367.2. Found: 368.4 (M+H)$^+$.

Preparation of (R)-ethyl 3-(5-amino-6-((3,3-difluorocyclobutyl)(isobutyl)amino)pyridin-3-yl)butanoate

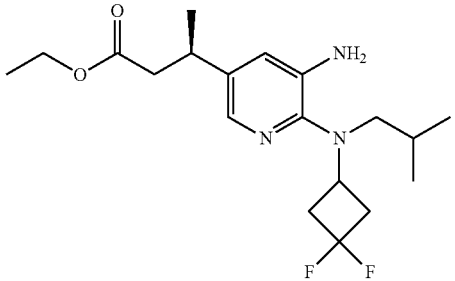 [SMILES: CCOC(=O)C[C@@H](C)c1cnc(N(CC(C)C)C2CC(F)(F)C2)c(N)c1]

A stir bar, NiBr$_2$ (DME) (2.96 mg, 9.58 µmol), and (S)-MeDuPhos (3.52 mg, 0.011 mmol) were added to septum-capped reaction vial that was subsequently purged with nitrogen. Isopropanol (1.25 mL) was added and the mixture stirred for 10 minutes. Triethylamine (0.067 mL, 0.48 mmol), formic acid (0.046 mL, 1.20 mmol), and a solution of (E)-ethyl 3-(5-amino-6-((3,3-difluorocyclobutyl)(isobutyl)amino)pyridin-3-yl)but-2-enoate (88 mg, 0.24 mmol) in isopropanol (1.25 mL) were then added sequentially under nitrogen. The reaction vial was placed in a heating block that was preheated to 80° C. The mixture was stirred at 80° C. under nitrogen for 48 hours. The reaction appeared to have stalled. The reaction mixture was allowed to cool to room temperature. In a separate vial, additional NiBr$_2$ (DME) (2.96 mg, 9.58 µmol) and (S)-MeDuPhos (3.52 mg, 0.011 mmol) were flushed with nitrogen. 0.5 mL of dry isopropanol were added and the mixture stirred for 10 minutes. This mixture was transferred to the original reaction vial under nitrogen. Additional triethylamine (0.067 mL, 0.479 mmol) and formic acid (0.046 mL, 1.197 mmol) were also added and the mixture heated at 80° C. for 16 hours. The reaction mixture was allowed to cool to room temperature and concentrated. The residue purified by silica chromatography eluting with a gradient of 0% to 30% ethyl acetate in hexanes. Fractions were concentrated to give (R)-ethyl 3-(5-amino-6-((3,3-difluorocyclobutyl)(isobutyl)amino)pyridin-3-yl)butanoate (57 mg, 0.15 mmol, 64% yield). LCMS (ESI) m/z calculated for $C_{19}H_{29}F_2N_3O_2$: 369.2. Found: 370.4 (M+H)$^+$.

Preparation of (R)-ethyl 3-(5-((6-chloropyridin-3-yl)amino)-6-((3,3-difluorocyclobutyl)(isobutyl)amino)pyridin-3-yl)butanoate

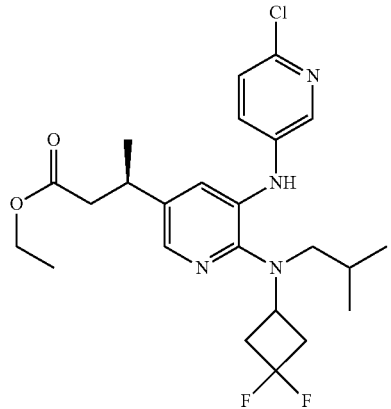 [SMILES: CCOC(=O)C[C@@H](C)c1cnc(N(CC(C)C)C2CC(F)(F)C2)c(Nc2ccc(Cl)nc2)c1]

(R)-Ethyl 3-(5-amino-6-((3,3-difluorocyclobutyl)(isobutyl)amino)pyridin-3-yl)butanoate (53 mg, 0.14 mmol), 5-bromo-2-chloropyridine (33.1 mg, 0.172 mmol), potassium carbonate (99 mg, 0.72 mmol), tris(dibenzylideneacetone)dipalladium(0) (26.3 mg, 0.029 mmol), and Xantphos (33.2 mg, 0.057 mmol) were placed in a septum-capped round bottom flask and thoroughly purged with nitrogen. Toluene (1.5 mL) was added and the mixture heated at 100° C. for 3 hours. The mixture was allowed to cool to room temperature, quenched with brine, and extracted 2 times with ethyl acetate. The combined organic layers were washed with brine, dried over sodium sulfate, and concentrated. The residue was purified by silica chromatography eluting with a gradient of 0% to 30% ethyl acetate in hexanes. Fractions were concentrated to give (R)-ethyl 3-(5-((6-chloropyridin-3-yl)amino)-6-((3,3-difluorocyclobutyl)(isobutyl)amino)pyridin-3-yl)butanoate (29 mg, 0.060 mmol, 42% yield). LCMS (ESI) m/z calculated for $C_{24}H_{31}ClF_2N_4O_2$: 480.2. Found: 481.4 (M+H)$^+$.

Preparation of (R)-3-(5-((6-chloropyridin-3-yl)amino)-6-((3,3-difluorocyclobutyl)(isobutyl)amino)pyridin-3-yl) butanoic acid

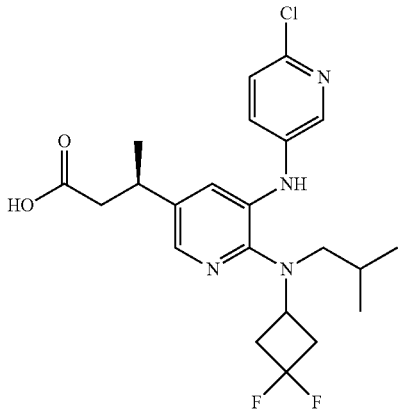 [SMILES: CC(C)CN(c1ncc([C@H](C)CC(=O)O)cc1Nc1ccc(Cl)nc1)C1CC(F)(F)C1]

1M Sodium hydroxide (0.603 mL, 0.603 mmol) was added to a solution of (R)-ethyl 3-(5-((6-chloropyridin-3-yl)amino)-6-((3,3-difluorocyclobutyl)(isobutyl)amino)pyridin-3-yl)butanoate (29 mg, 0.060 mmol) in ethanol (1 mL) and the mixture stirred at 50° C. for 1 hour, cooled to room temperature, quenched with 1 mL of 1M citric acid, and concentrated. The residue was purified by reverse phase medium pressure chromatography. Fractions were concentrated and the residue lyophilized to give (R)-3-(5-((6-chloropyridin-3-yl)amino)-6-((3,3-difluorocyclobutyl)(isobutyl)amino)pyridin-3-yl)butanoic acid (18 mg, 0.040 mmol, 65.8% yield) as a white powder. LCMS (ESI) m/z calculated for $C_{22}H_{27}ClF_2N_4O_2$: 452.2. Found: 453.3 (M+H)$^+$. $^1$H NMR (400 MHz, METHANOL-d$_4$) δ ppm 8.0 (br. s., 1H), 7.9 (br. s., 1H), 7.3-7.5 (m, 2H), 7.2-7.3 (m, 1H), 3.9-4.0 (m, 1H), 3.1-3.2 (m, 1H), 2.8-3.0 (m, 2H), 2.7-2.8 (m, 2H), 2.5-2.6 (m, 2H), 2.2-2.5 (m, 2H), 1.5-1.7 (m, 1H), 1.2-1.4 (m, 3H), 0.6-0.8 (m, 6H).

Example 20

(R)-3-(6-((3,3-difluorocyclobutyl)(isobutyl)amino)-5-((3-(trifluoromethyl)-1,2,4-thiadiazol-5-yl)amino)pyridin-3-yl)butanoic acid

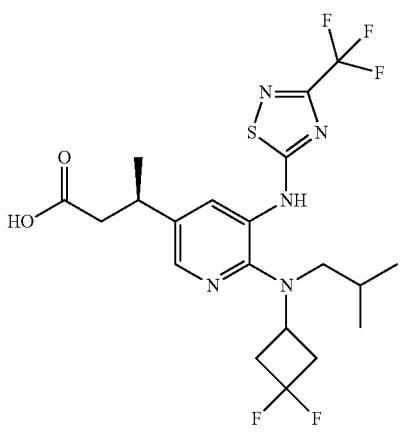 [SMILES: CC(C)CN(c1ncc([C@H](C)CC(=O)O)cc1Nc1nc(C(F)(F)F)ns1)C1CC(F)(F)C1]

Diacetoxypalladium (0.608 mg, 2.71 μmol) and XPhos (0.387 mg, 0.812 μmol) were placed in a septum-capped vial and was degassed with nitrogen. t-Butanol (0.5 mL) and water (0.195 μl, 10.8 μmol) were added and the mixture heated at 85° C. for 1.5 minutes. The mixture was allowed to cool to room temperature. In a second vial, (R)-ethyl 3-(5-amino-6-((3,3-difluorocyclobutyl)(isobutyl)amino)pyridin-3-yl)butanoate (50 mg, 0.135 mmol), potassium carbonate (31 mg, 0.224 mmol), and 5-chloro-3-(trifluoromethyl)-1,2,4-thiadiazole (28.7 mg, 0.152 mmol) in t-butanol (1 mL) were degassed with nitrogen. The Pd catalyst mixture in the first vial was then added under nitrogen and the mixture heated at 85° C. overnight. LC-MS showed starting material and the bis-arylated product (R)-ethyl 3-(5-(bis(3-(trifluoromethyl)-1,2,4-thiadiazol-5-yl)amino)-6-((3,3-difluorocyclobutyl)(isobutyl)amino)pyridin-3-yl)butanoate.

The mixture was allowed to cool to room temperature before 1.5 mL of 1M sodium hydroxide (1.5 mL, 1.5 mmol) was added. The mixture was heated at 60° C. for 3 hours. The mixture was allowed to cool to room temperature and was concentrated. The residue was purified by reverse phase medium pressure chromatography (10% to 100% AcCN/water/0.1% formic acid). Fractions were concentrated and the residue lyophilized to give (R)-3-(6-((3,3-difluorocyclobutyl)(isobutyl)amino)-5-((3-(trifluoromethyl)-1,2,4-thiadiazol-5-yl)amino)pyridin-3-yl)butanoic acid (18 mg, 0.036 mmol, 26.9% yield) as an off-white solid. LCMS (ESI) m/z calculated for $C_{20}H_{24}F_5N_5O_2S$: 493.2. Found: 494.3 (M+H)$^+$. $^1$H NMR (400 MHz, METHANOL-d$_4$) δ ppm 8.5 (d, J=1.6 Hz, 1H), 8.0 (d, J=2.0 Hz, 1H), 3.9-4.0 (m, 1H), 2.9 (d, J=6.8 Hz, 2H), 2.6-2.8 (m, 2H), 2.6 (d, J=7.4 Hz, 2H), 2.3-2.5 (m, 2H), 1.5-1.6 (m, 1H), 1.3 (d, J=7.0 Hz, 3H), 0.7 (d, J=6.6 Hz, 6H).

Example 21

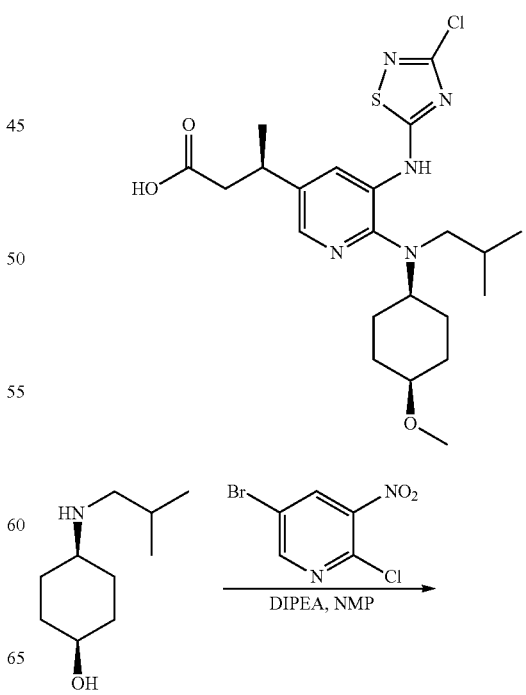

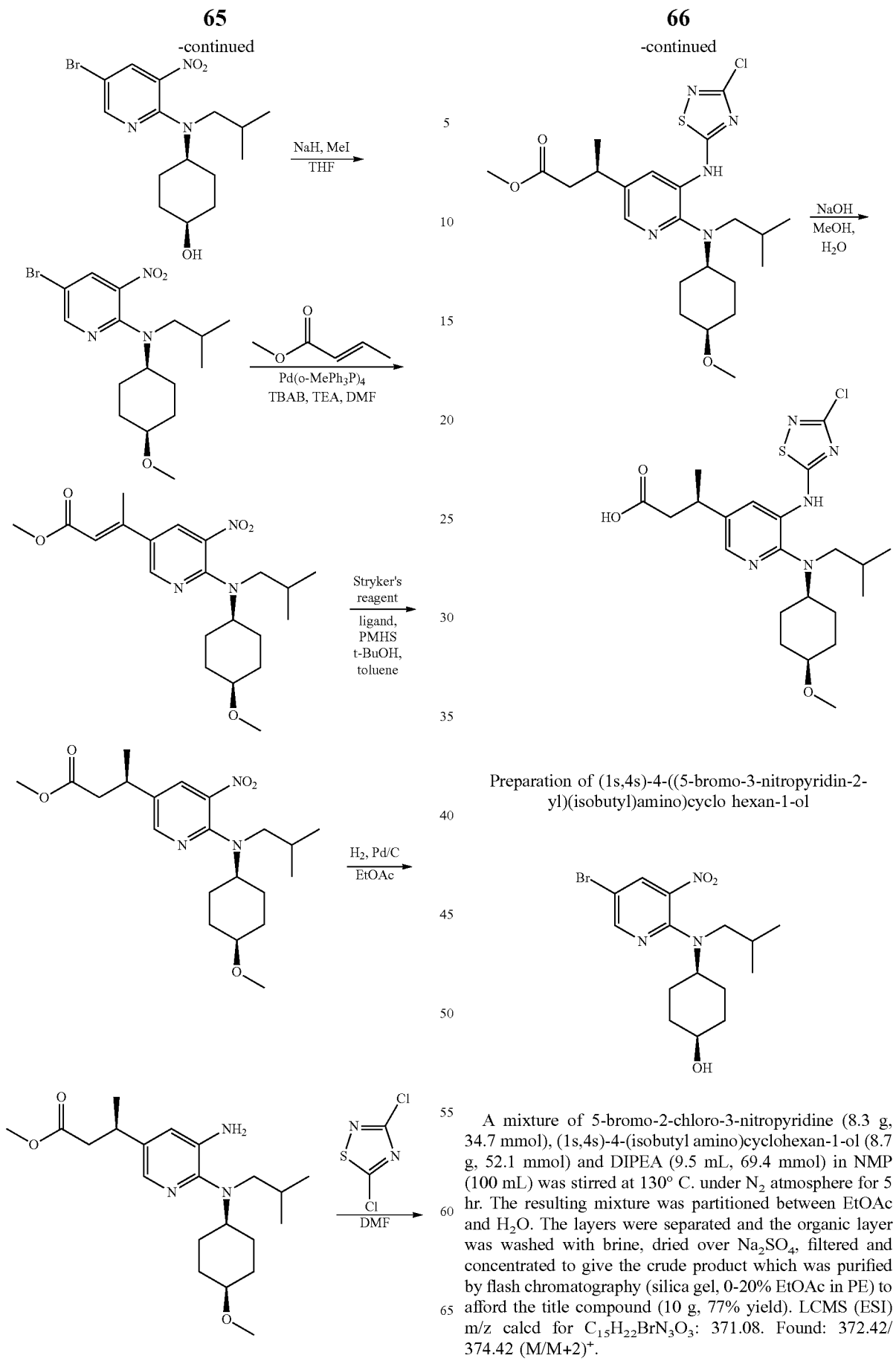

Preparation of (1s,4s)-4-((5-bromo-3-nitropyridin-2-yl)(isobutyl)amino)cyclohexan-1-ol A mixture of 5-bromo-2-chloro-3-nitropyridine (8.3 g, 34.7 mmol), (1s,4s)-4-(isobutyl amino)cyclohexan-1-ol (8.7 g, 52.1 mmol) and DIPEA (9.5 mL, 69.4 mmol) in NMP (100 mL) was stirred at 130° C. under $N_2$ atmosphere for 5 hr. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (10 g, 77% yield). LCMS (ESI) m/z calcd for $C_{15}H_{22}BrN_3O_3$: 371.08. Found: 372.42/374.42 (M/M+2)+.

Preparation of 5-bromo-N-isobutyl-N-((1s,4s)-4-methoxycyclohexyl)-3-nitro pyridin-2-amine

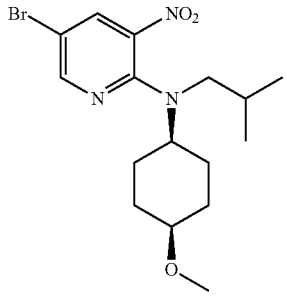

At 0° C., to a solution of (1s,4s)-4-((5-bromo-3-nitropyridin-2-yl)(isobutyl)amino)cyclo hexan-1-ol (10 g, 26.7 mmol) in THF (100 mL) was added NaH (60%, 6.4 g, 160 mmol). The reaction mixture was stirred at r.t. for 2 hr before the addition of MeI (16.7 mL, 267 mmol). After stirred at r.t. overnight, the resulting mixture was quenched with sat. NH$_4$Cl aq. solution and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (8.3 g, 81% yield). LCMS (ESI) m/z calcd for C$_{16}$H$_{24}$BrN$_3$O$_3$: 385.10. Found: 386.59/388.57 (M/M+2)$^+$.

Preparation of methyl (E)-3-(6-(isobutyl((1s,4s)-4-methoxycyclohexyl)amino)-5-nitropyridin-3-yl)but-2-enoate

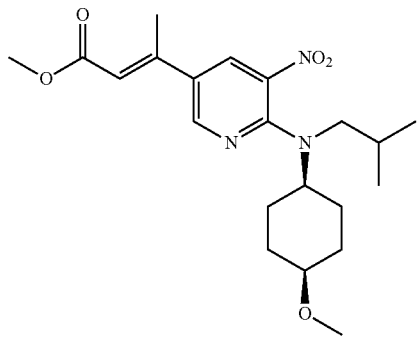 [SMILES: COC(=O)/C=C(\C)c1cnc(N(CC(C)C)[C@H]2CC[C@@H](OC)CC2)c([N+](=O)[O-])c1]

A mixture of 5-bromo-N-isobutyl-N-((1s,4s)-4-methoxycyclohexyl)-3-nitropyridin-2-amine (8.3 g, 21.5 mmol), methyl (E)-but-2-enoate (6.45 g, 64.5 mmol), TBAB (1.3 g, 4.3 mmol), Pd(o-MePh$_3$P)$_4$ (845 mg, 1.075 mmol) and TEA (4.39 g, 43.0 mmol) in DMF (90 mL) was stirred at 110° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (5.2 g, 60% yield). LCMS (ESI) m/z calcd for C$_{21}$H$_{31}$N$_3$O$_5$: 405.23. Found: 406.24 (M+1)$^+$.

Preparation of methyl (R)-3-(6-(isobutyl((1s,4S)-4-methoxycyclohexyl)amino)-5-nitropyridin-3-yl)butanoate

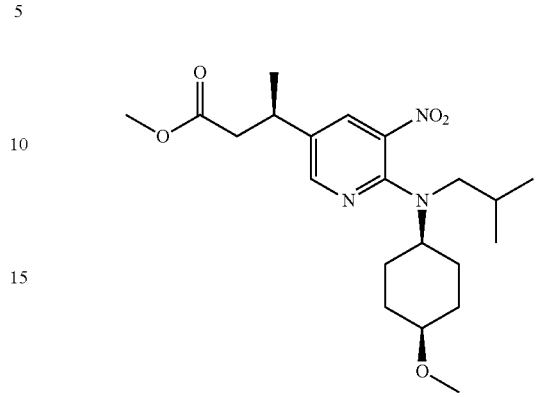

At −5° C., to a mixture of (CuHPh$_3$P)$_6$ (407 mg, 0.21 mmol) and (R,S)—PPF—P(tBu)$_2$ (400 mg, 0.74 mmol) in toluene (60 mL) was added PMHS (2.6 mL) and t-BuOH (2.6 mL) before the introduction of methyl (E)-3-(6-(isobutyl((1s,4s)-4-methoxycyclohexyl) amino)-5-nitropyridin-3-yl)but-2-enoate (5.2 g, 12.8 mmol). After stirred at r.t. for 4 days, the resulting mixture was quenched with sat. NaHCO$_3$ aq. solution and extracted with EtOAc. The organic layer was washed with brine, dried over Na$_2$SO$_4$, filtered and concentrated to give the crude product which was purified by flash chromatography (silica gel, 0-10% EtOAc in PE) to afford the title compound (3.9 g, 75% yield). LCMS (ESI) m/z calcd for C$_{21}$H$_{33}$N$_3$O$_5$: 407.24. Found: 408.15 (M+1)$^+$.

Preparation of methyl (R)-3-(5-amino-6-(isobutyl ((1s,4S)-4-methoxycyclohexyl) amino)pyridin-3-yl) butanoate

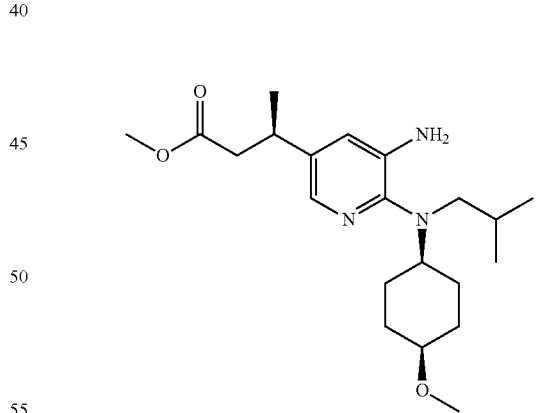

A mixture of methyl (R)-3-(6-(isobutyl((1s,4S)-4-methoxycyclohexyl)amino)-5-nitro pyridin-3-yl)butanoate (3.9 g, 9.58 mmol) and 10% Pd/C (2.0 g) in EtOAc (40 mL) was stirred at 50° C. under H$_2$ atmosphere overnight. The resulting mixture was filtered through a pad of Celite and the filtrate was concentrated under reduced pressure to give the crude product which was purified by flash chromatography (silica gel, 0-20% EtOAc in PE) to afford the title compound (1.47 g, 42% yield). LCMS (ESI) m/z calcd for C$_{21}$H$_{35}$N$_3$O$_3$: 377.27. Found: 378.46 (M+1)$^+$.

Preparation of methyl (R)-3-(5-((3-chloro-1,2,4-thiadiazol-5-yl)amino)-6-(isobutyl ((1s,4S)-4-methoxycyclohexyl)amino)pyridin-3-yl)butanoate

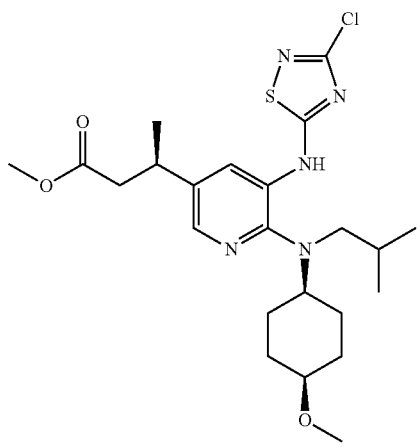 [SMILES: COC(=O)C[C@@H](C)c1cnc(N(CC(C)C)[C@H]2CC[C@@H](OC)CC2)c(Nc2nc(Cl)ns2)c1]

A mixture of methyl (R)-3-(5-amino-6-(isobutyl((1s,4S)-4-methoxycyclohexyl)amino) pyridin-3-yl)butanoate (100 mg, 0.365 mmol) and 3,5-dichloro-1,2,4-thiadiazole (82 mg, 0.53 mmol) in DMF (3 mL) was stirred at 90° C. under $N_2$ atmosphere overnight. The resulting mixture was partitioned between EtOAc and $H_2O$. The organic layer was washed with brine, dried over $Na_2SO_4$, filtered and concentrated to give the crude product which was purified by flash chromatography (silica gel, 0-20% EtOAc in PE) to afford the title compound (50 mg, 28% yield). LCMS (ESI) m/z calcd for $C_{23}H_{34}ClN_5O_3S$: 495.21. Found: 496.39/498.39 (M/M+2)$^+$.

Preparation of (R)-3-(5-((3-chloro-1,2,4-thiadiazol-5-yl)amino)-6-(isobutyl((1s,4S)-4-methoxycyclohexyl)amino)pyridin-3-yl)butanoic acid

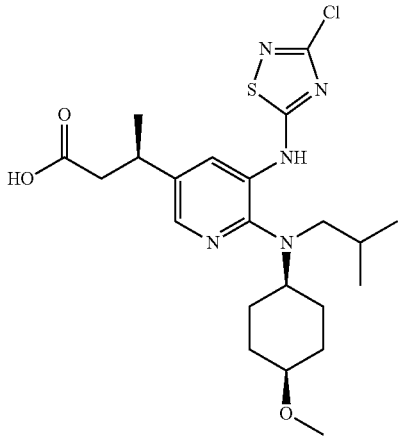 [SMILES: CO[C@H]1CC[C@@H](N(CC(C)C)c2ncc([C@H](C)CC(=O)O)cc2Nc2nc(Cl)ns2)CC1]

To a solution of methyl (R)-3-(5-((3-chloro-1,2,4-thiadiazol-5-yl)amino)-6-(isobutyl ((1s,4S)-4-methoxycyclohexyl)amino)pyridin-3-yl)butanoate (50 mg, 0.101 mmol) in MeOH (2 mL) was added 4N NaOH aq. (0.5 mL). After stirred at r.t for 6 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (23 mg, 64% yield) as a white powder. $^1$H NMR (400 MHz, CDCl$_3$) δ 8.83 (s, 1H), 8.07 (d, J=2.1 Hz, 1H), 7.74 (d, J=2.1 Hz, 1H), 3.40-3.31 (m, 2H), 3.28 (s, 3H), 3.02 (d, J=7.0 Hz, 2H), 2.75-2.60 (m, 3H), 2.01-1.95 (m, 2H), 1.79-1.69 (m, 2H), 1.63-1.53 (m, 2H), 1.42-1.25 (m, 6H), 0.82 (d, J=6.6 Hz, 6H). LCMS (ESI) m/z calcd for $C_{22}H_{32}ClN_5O_3S$: 481.19. Found: 482.42/484.39 (M/M+2)$^+$.

Example 22

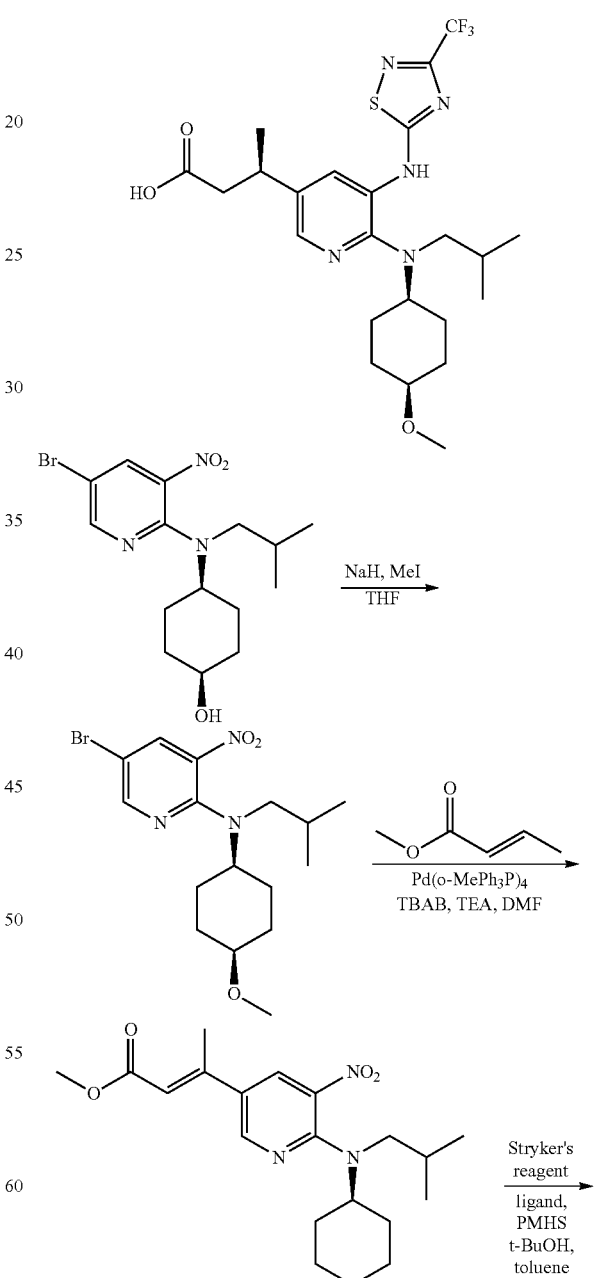

-continued

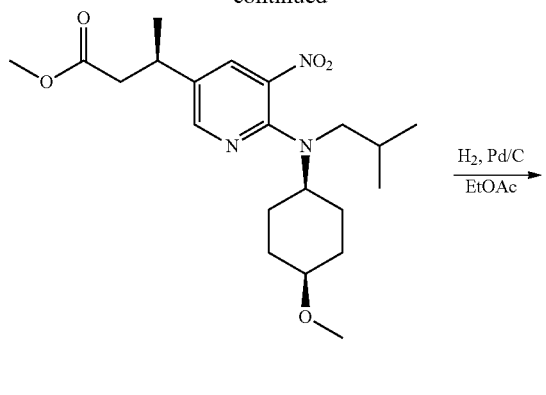

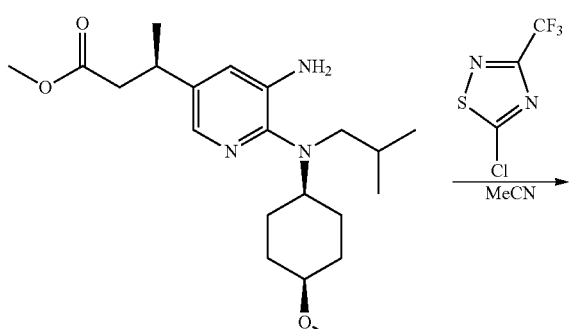

Preparation of 5-bromo-N-isobutyl-N-((1s,4s)-4-methoxycyclohexyl)-3-nitropyridin-2-amine

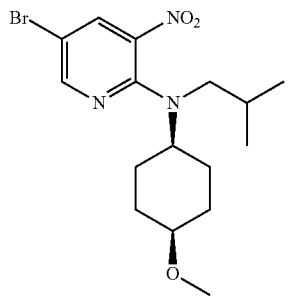 [SMILES: CO[C@H]1CC[C@@H](N(CC(C)C)c2ncc(Br)cc2[N+](=O)[O-])CC1]

At 0° C., to a solution of (1s,4s)-4-((5-bromo-3-nitropyridin-2-yl)(isobutyl)amino) cyclohexan-1-ol (10 g, 26.7 mmol) in THF (100 mL) was added NaH (60%, 6.4 g, 160 mmol). The reaction mixture was stirred at 0° C. for 2 hr before the addition of MeI (16.7 mL, 267 mmol). After stirred at r.t. overnight, the resulting mixture was quenched with sat. NH$_4$Cl aq. solution and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (8.3 g, 81% yield) as a red oil. LCMS (ESI) m/z calcd for C$_{16}$H$_{24}$BrN$_3$O$_3$: 385.10. Found: 386.59/388.03 (M/M+2)$^+$.

Preparation of methyl (E)-3-(6-(isobutyl((1s,4s)-4-methoxycyclohexyl)amino)-5-nitropyridin-3-yl)but-2-enoate

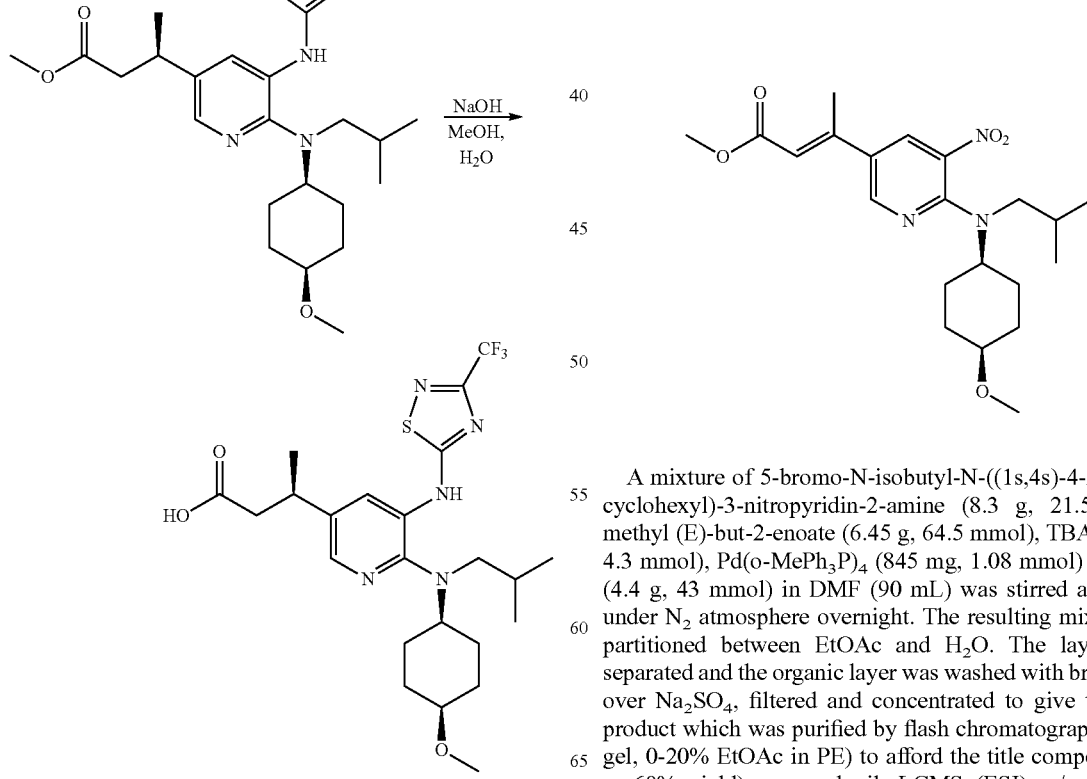

A mixture of 5-bromo-N-isobutyl-N-((1s,4s)-4-methoxycyclohexyl)-3-nitropyridin-2-amine (8.3 g, 21.5 mmol), methyl (E)-but-2-enoate (6.45 g, 64.5 mmol), TBAB (1.3 g, 4.3 mmol), Pd(o-MePh$_3$P)$_4$ (845 mg, 1.08 mmol) and TEA (4.4 g, 43 mmol) in DMF (90 mL) was stirred at 110° C. under N$_2$ atmosphere overnight. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-20% EtOAc in PE) to afford the title compound (5.2 g, 60% yield) as a red oil. LCMS (ESI) m/z calcd for C$_{21}$H$_{31}$N$_3$O$_5$: 405.23. Found: 406.24 (M+1)$^+$.

Preparation of methyl (R)-3-(6-(isobutyl((1s,4S)-4-methoxycyclohexyl)amino)-5-nitropyridin-3-yl)butanoate

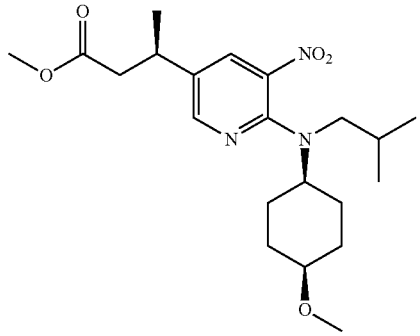

At −5° C., to a mixture of (CuHPh₃P)₆ (407 mg, 0.21 mmol) and (R,S)—PPF—P(tBu)₂ (400 mg, 0.74 mmol) in toluene (60 mL) was added PMHS (2.6 mL) and t-BuOH (2.6 mL) before the introduction of methyl (E)-3-(6-(isobutyl((1s,4s)-4-methoxycyclohexyl) amino)-5-nitropyridin-3-yl)but-2-enoate (5.2 g, 12.8 mmol). After stirred at r.t. for 4 days, the resulting mixture was quenched with sat. NaHCO₃ aq. solution and extracted with EtOAc. The organic layer was washed with brine, dried over Na₂SO₄, filtered and concentrated to give the crude product which was purified by flash chromatography (silica gel, 0-20% EtOAc in PE) to afford the title compound (3.9 g, 75% yield). LCMS (ESI) m/z calcd for $C_{21}H_{33}N_3O_5$: 407.24. Found: 408.68 (M+1)⁺.

Preparation of methyl (R)-3-(5-amino-6-(isobutyl((1s,4S)-4-methoxycyclohexyl) amino)pyridin-3-yl)butanoate

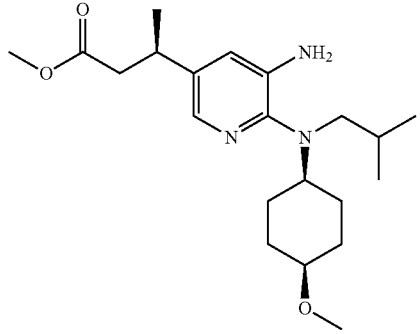 [SMILES: COC(=O)C[C@@H](C)c1cnc(N(CC(C)C)[C@H]2CC[C@@H](OC)CC2)c(N)c1]

A mixture of methyl (R)-3-(6-(isobutyl((1s,4S)-4-methoxycyclohexyl)amino)-5-nitropyridin-3-yl)butanoate (3.9 g, 4.58 mmol) and 10% Pd/C (2.0 g) in EtOAc (40 mL) was purged with H₂ and stirred at 50° C. overnight. The resulting mixture was filtered through a pad of Celite and the filtrate was concentrated under reduced pressure to give the crude product which was purified by flash chromatography (silica gel, 0-30% EtOAc in PE) to afford the title compound (1.47 g, 42% yield) as a yellow oil. LCMS (ESI) m/z calcd for $C_{21}H_{35}N_3O_3$: 377.27. Found: 378.46 (M+1)⁺.

Preparation of methyl (R)-3-(6-(isobutyl((1s,4S)-4-methoxycyclohexyl)amino)-5-((3-(trifluoromethyl)-1,2,4-thiadiazol-5-yl)amino)pyridin-3-yl)butanoate

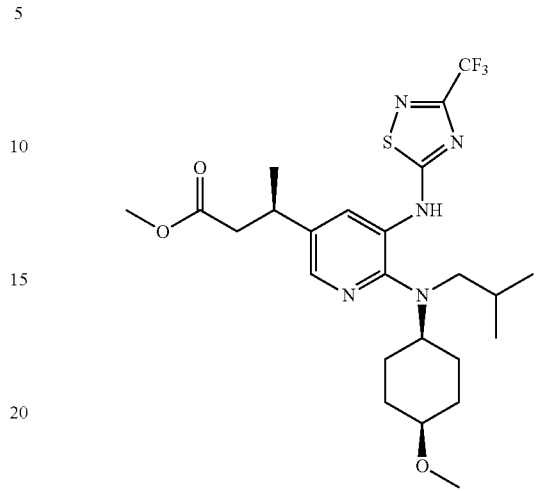

A mixture of methyl (R)-3-(5-amino-6-(isobutyl((1s,4S)-4-methoxycyclohexyl) amino) pyridin-3-yl)butanoate (100 mg, 0.265 mmol) and 5-chloro-3-(trifluoromethyl)-1,2,4-thiadiazole (150 mg, 0.796 mmol) in MeCN (3 mL) was stirred at 90° C. under N₂ atmosphere for 4 days. The resulting mixture was partitioned between EtOAc and H₂O. The organic layer was washed with brine, dried over Na₂SO₄, filtered and concentrated to give the crude product which was purified by flash chromatography (silica gel, 0-20% EtOAc in PE) to afford the title compound (70 mg, 50% yield). LCMS (ESI) m/z calcd for $C_{24}H_{34}F_3N_5O_3S$: 529.23. Found: 530.50 (M+1)⁺.

Preparation of (R)-3-(6-(isobutyl((1s,4S)-4-methoxycyclohexyl)amino)-5-((3-(tri fluoromethyl)-1,2,4-thiadiazol-5-yl)amino)pyridin-3-yl) butanoic acid

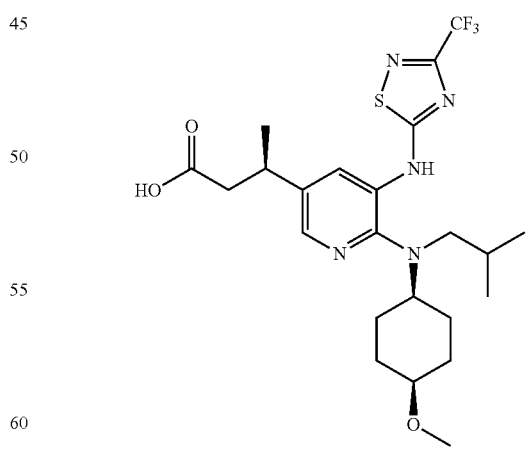

To a solution of methyl (R)-3-(6-(isobutyl((1s,4S)-4-methoxycyclohexyl)amino)-5-((3-(trifluoromethyl)-1,2,4-thiadiazol-5-yl)amino)pyridin-3-yl)butanoate (70 mg, 0.133 mmol) in MeOH (3 mL) was added 4N NaOH aq. (1 mL). After stirred at r.t for 5 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (43.5 mg, 63% yield) as a white powder. $^1$H NMR (400 MHz, CDCl$_3$) δ 8.91 (s, 1H), 8.08 (d, J=2.1 Hz, 1H), 7.92 (d, J=2.0 Hz, 1H), 3.41-3.31 (m, 2H), 3.28 (s, 3H), 3.03 (d, J=7.0 Hz, 2H), 2.76-2.65 (m, 3H), 1.98 (d, J=15.4 Hz, 2H), 1.78-1.71 (m, 2H), 1.61-1.56 (m, 2H), 1.42-1.25 (m, 6H), 0.83 (d, J=6.6 Hz, 6H).). LCMS (ESI) m/z calcd for C$_{23}$H$_{32}$F$_3$N$_5$O$_3$S: 515.22. Found: 516.43 (M+1)$^+$.

Example 23

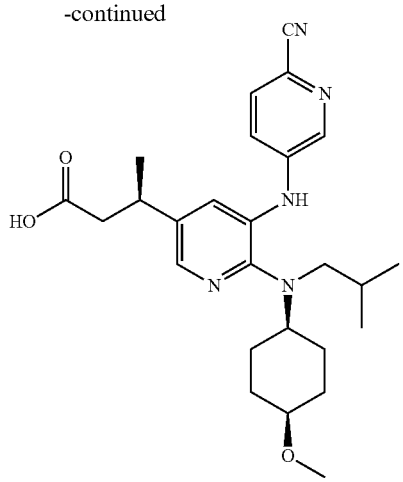

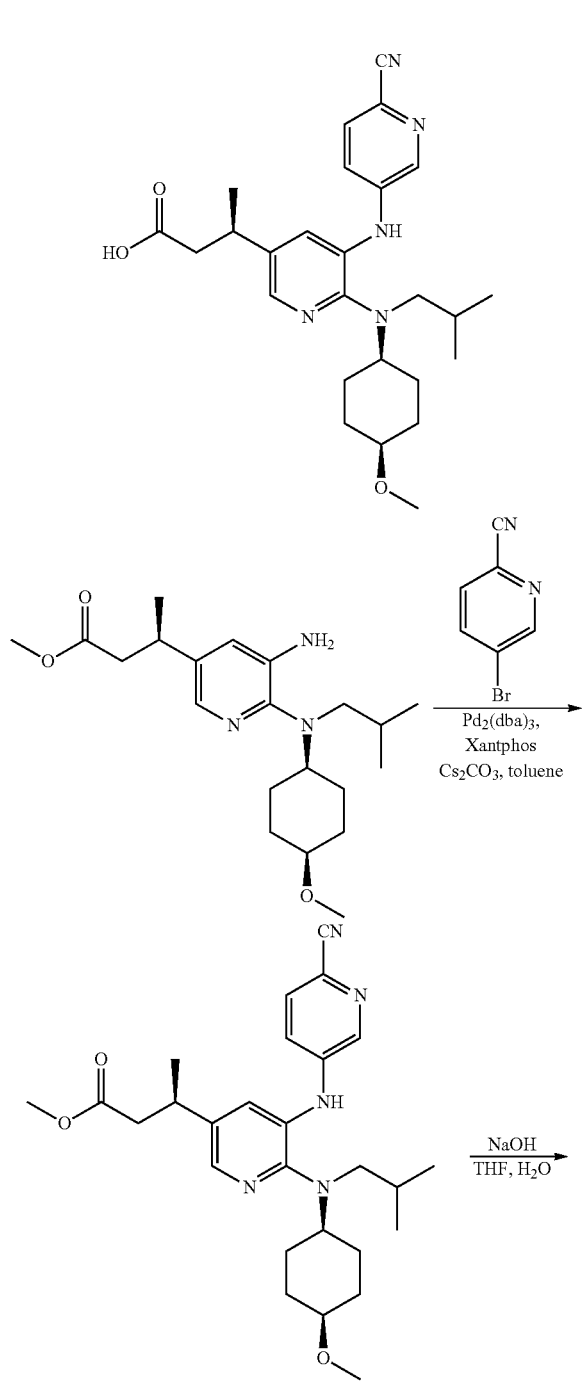

Preparation of methyl (R)-3-(5-((6-cyanopyridin-3-yl)amino)-6-(isobutyl((1s,4S)-4-methoxycyclohexyl)amino)pyridin-3-yl) butanoate

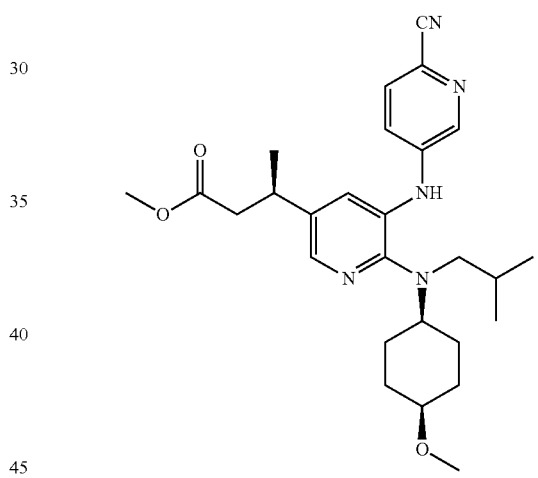

A mixture of methyl (R)-3-(5-amino-6-(isobutyl((1s,4S)-4-methoxycyclohexyl)amino) pyridin-3-yl)butanoate (100 mg, 0.265 mmol), 5-bromopicolinonitrile (95 mg, 0.53 mmol), Pd$_2$(dba)$_3$ (50 mg, 0.053 mmol), Xantphos (75 mg, 0.106 mmol) and Cs$_2$CO$_3$ (175 mg, 0.53 mmol) in toluene (3 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (100 mg, 78% yield). LCMS (ESI) m/z calcd for C$_{27}$H$_{37}$N$_5$O$_3$: 479.29. Found: 480.49 (M+1)$^+$.

Preparation of (R)-3-(5-((6-cyanopyridin-3-yl)amino)-6-(isobutyl((1s,4S)-4-methoxycyclohexyl)amino)pyridin-3-yl)butanoic acid

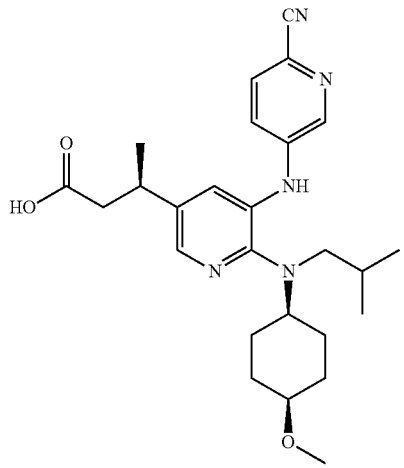 [SMILES: CO[C@H]1CC[C@@H](N(CC(C)C)c2ncc([C@H](C)CC(=O)O)cc2Nc2ccc(C#N)nc2)CC1]

To a solution of methyl (R)-3-(5-((6-cyanopyridin-3-yl)amino)-6-(isobutyl((1s,4S)-4-methoxycyclohexyl)amino)pyridin-3-yl)butanoate (100 mg, 0.209 mmol) in THF (4 mL) was added 4N NaOH aq. (1.5 mL). After stirred at r.t for 24 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (53 mg, 54% yield) as a white powder. $^1$H NMR (400 MHz, CDCl$_3$) δ 8.44 (d, J=2.7 Hz, 1H), 8.00 (d, J=2.1 Hz, 1H), 7.59 (d, J=8.6 Hz, 1H), 7.50 (d, J=2.1 Hz, 1H), 7.38 (dd, J=8.6, 2.8 Hz, 1H), 6.84 (s, 1H), 3.35-3.22 (m, 5H), 3.06-2.98 (m, 2H), 2.72-2.61 (m, 3H), 1.98-1.91 (m, 2H), 1.83-1.74 (m, 2H), 1.54-1.34 (m, 6H), 1.20-1.11 (m, 2H), 0.82 (d, J=6.6 Hz, 6H). LCMS (ESI) m/z calcd for C$_{26}$H$_{35}$N$_5$O$_3$: 465.27. Found: 466.48 (M+1)$^+$.

Example 24

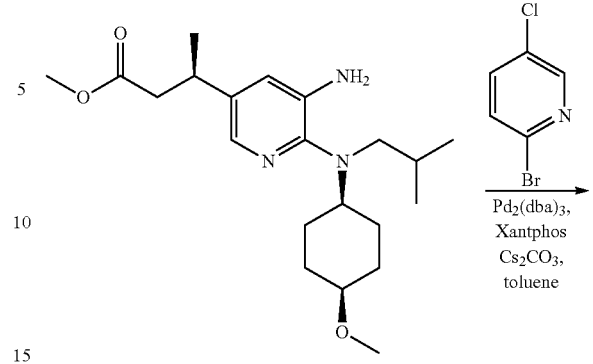

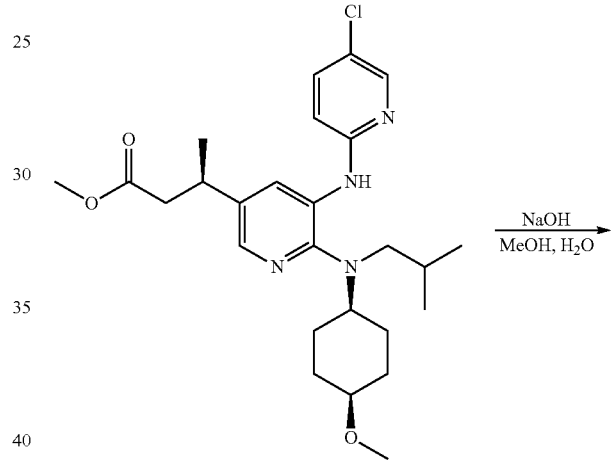

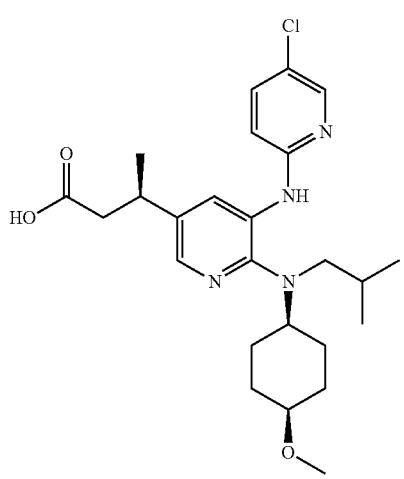

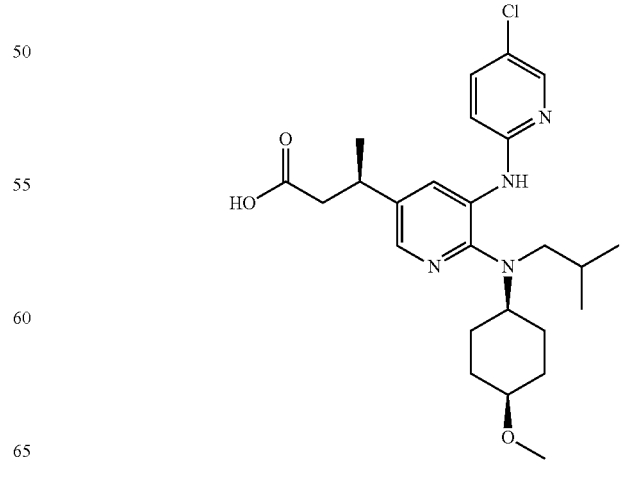

Preparation of methyl (R)-3-(5-((5-chloropyridin-2-yl)amino)-6-(isobutyl((1s,4S)-4-methoxycyclohexyl)amino)pyridin-3-yl)butanoate

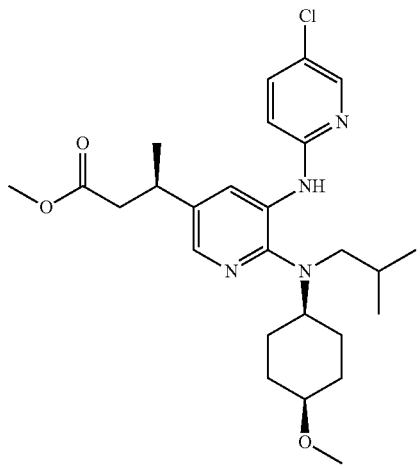 [SMILES: COC(=O)C[C@@H](C)c1cnc(N(CC(C)C)[C@H]2CC[C@@H](OC)CC2)c(Nc2ccc(Cl)cn2)c1]

A mixture of methyl (R)-3-(5-amino-6-(isobutyl((1s,4S)-4-methoxycyclohexyl)amino) pyridin-3-yl)butanoate (100 mg, 0.265 mmol), 2-bromo-5-chloropyridine (100 mg, 0.53 mmol), Pd$_2$(dba)$_3$ (50 mg, 0.053 mmol), Xantphos (75 mg, 0.106 mmol) and Cs$_2$CO$_3$ (175 mg, 0.53 mmol) in toluene (3 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (83 mg, 64% yield). LCMS (ESI) m/z calcd for C$_{26}$H$_{37}$ClN$_4$O$_3$: 488.26. Found: 489.42/491.39 (M/M+2)$^+$.

Preparation of (R)-3-(5-((5-chloropyridin-2-yl)amino)-6-(isobutyl((1s,4S)-4-methoxycyclohexyl)amino)pyridin-3-yl)butanoic acid

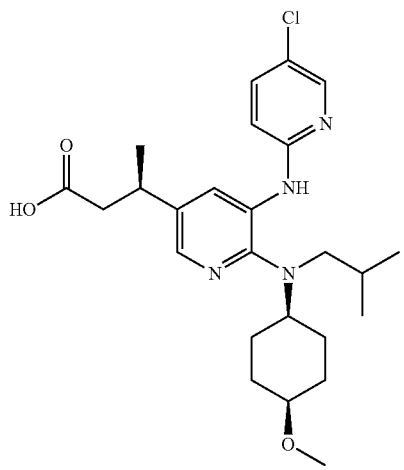 [SMILES: CO[C@H]1CC[C@@H](N(CC(C)C)c2ncc([C@H](C)CC(=O)O)cc2Nc2ccc(Cl)cn2)CC1]

To a solution of methyl (R)-3-(5-((5-chloropyridin-2-yl)amino)-6-(isobutyl((1s,4S)-4-methoxycyclohexyl)amino) pyridin-3-yl)butanoate (83 mg, 0.17 mmol) in MeOH (3 mL) was added 4N NaOH aq. (1.5 mL). After stirred at r.t for 5 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (47.5 mg, 59% yield) as a white powder. $^1$H NMR (400 MHz, CDCl$_3$) δ 8.41 (d, J=2.2 Hz, 1H), 8.15 (d, J=2.4 Hz, 1H), 7.83 (d, J=2.2 Hz, 1H), 7.62 (s, 1H), 7.41 (dd, J=8.8, 2.6 Hz, 1H), 6.60 (d, J=8.8 Hz, 1H), 3.32-3.15 (m, 5H), 2.95 (d, J=7.0 Hz, 2H), 2.72-2.53 (m, 3H), 1.92-1.86 (m, 2H), 1.76-1.66 (m, 2H), 1.54-1.47 (m, 2H), 1.38-1.27 (m, 4H), 1.22-1.13 (m, 2H), 0.77 (d, J=6.6 Hz, 6H). LCMS (ESI) m/z calcd for C$_{25}$H$_{35}$ClN$_4$O$_3$: 474.24. Found: 475.41/477.39 (M/M+2)$^+$.

Example 25

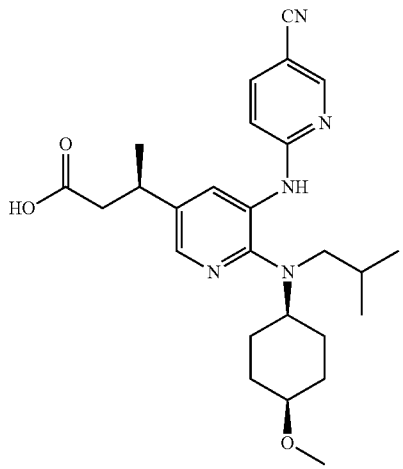 [SMILES: CO[C@H]1CC[C@@H](N(CC(C)C)c2ncc([C@H](C)CC(=O)O)cc2Nc2ccc(C#N)cn2)CC1]

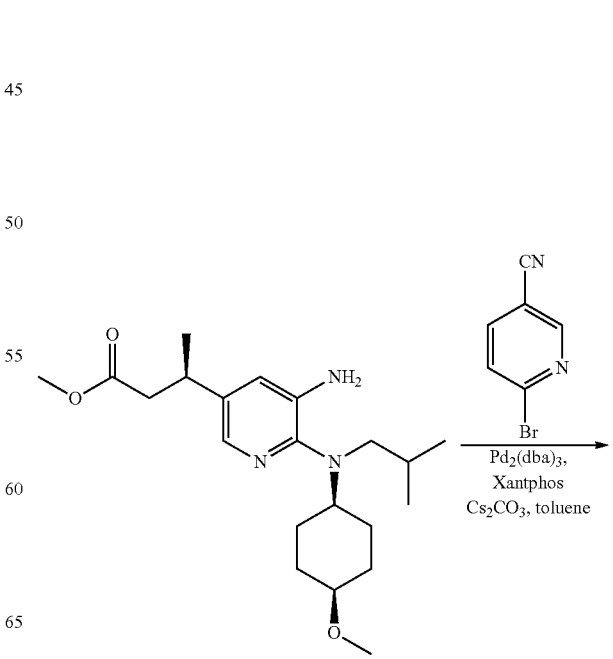

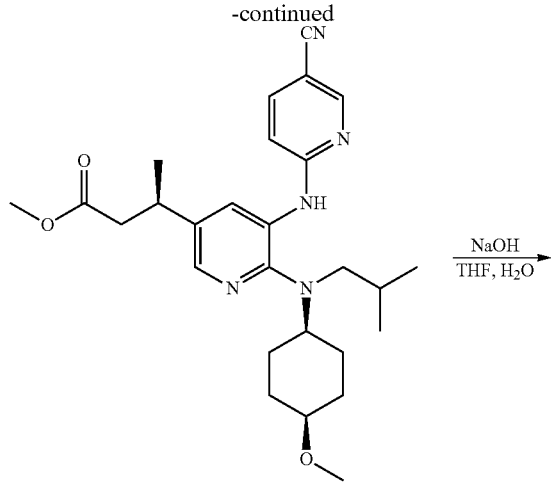

A mixture of methyl (R)-3-(5-amino-6-(isobutyl((1s,4S)-4-methoxycyclohexyl)amino) pyridin-3-yl)butanoate (100 mg, 0.265 mmol), 6-bromonicotinonitrile (95 mg, 0.53 mmol), Pd$_2$(dba)$_3$ (50 mg, 0.053 mmol), Xantphos (75 mg, 0.106 mmol) and Cs$_2$CO$_3$ (175 mg, 0.53 mmol) in toluene (3 mL) was stirred at 100° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (118 mg, 68% yield). LCMS (ESI) m/z calcd for C$_{27}$H$_{37}$N$_5$O$_3$: 479.29. Found: 480.49 (M+1)$^+$.

Preparation of (R)-3-(5-((5-cyanopyridin-2-yl)amino)-6-(isobutyl((1s,4S)-4-methoxycyclohexyl)amino)pyridin-3-yl)butanoic acid

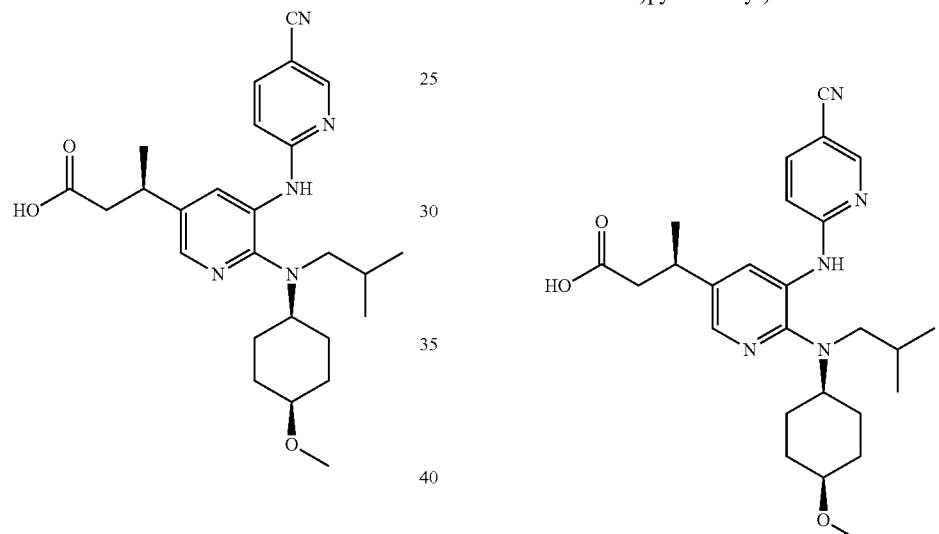

Preparation of methyl (R)-3-(5-((5-cyanopyridin-2-yl)amino)-6-(isobutyl((1s,4S)-4-methoxycyclohexyl)amino)pyridin-3-yl) butanoate

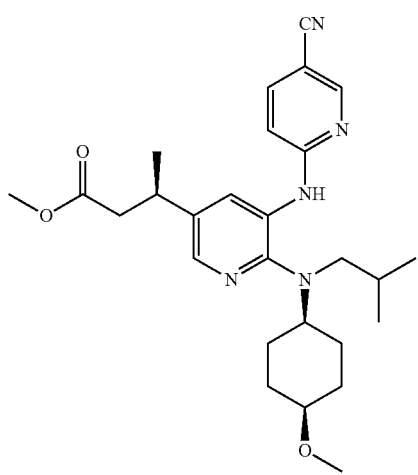 [SMILES: COC(=O)C[C@@H](C)c1cnc(N(CC(C)C)[C@H]2CC[C@@H](OC)CC2)c(Nc2ccc(C#N)cn2)c1]

To a solution of methyl (R)-3-(5-((5-cyanopyridin-2-yl)amino)-6-(isobutyl((1s,4S)-4-methoxycyclohexyl)amino) pyridin-3-yl)butanoate (118 mg, 0.246 mmol) in THF (5 mL) was added 4N NaOH aq. (1.5 mL). After stirred at r.t for 24 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (48 mg, 42% yield) as a white powder. $^1$H NMR (400 MHz, CDCl$_3$) δ 8.59-8.51 (m, 2H), 8.09 (s, 1H), 7.98 (d, J=2.3 Hz, 1H), 7.69 (dd, J=8.7, 2.3 Hz, 1H), 6.70 (d, J=8.7 Hz, 1H), 3.36-3.30 (m, 2H), 3.27 (s, 3H), 3.02 (d, J=7.0 Hz, 2H), 2.75-2.63 (m, 3H), 1.98-1.93 (m, 2H), 1.78-1.75 (m, 2H), 1.57-1.54 (m, 2H), 1.41-1.27 (m, 6H), 0.84 (d, J=6.6 Hz, 6H). LCMS (ESI) m/z calcd for C$_{26}$H$_{35}$N$_5$O$_3$: 465.27. Found: 466.50 (M+1)$^+$.

Example 26
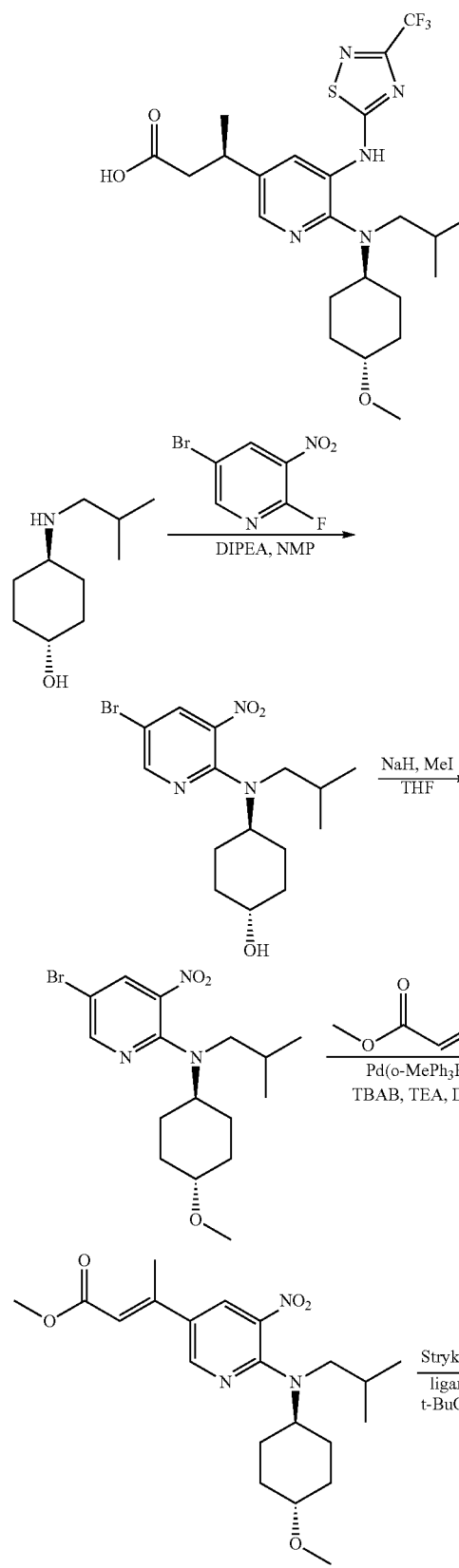
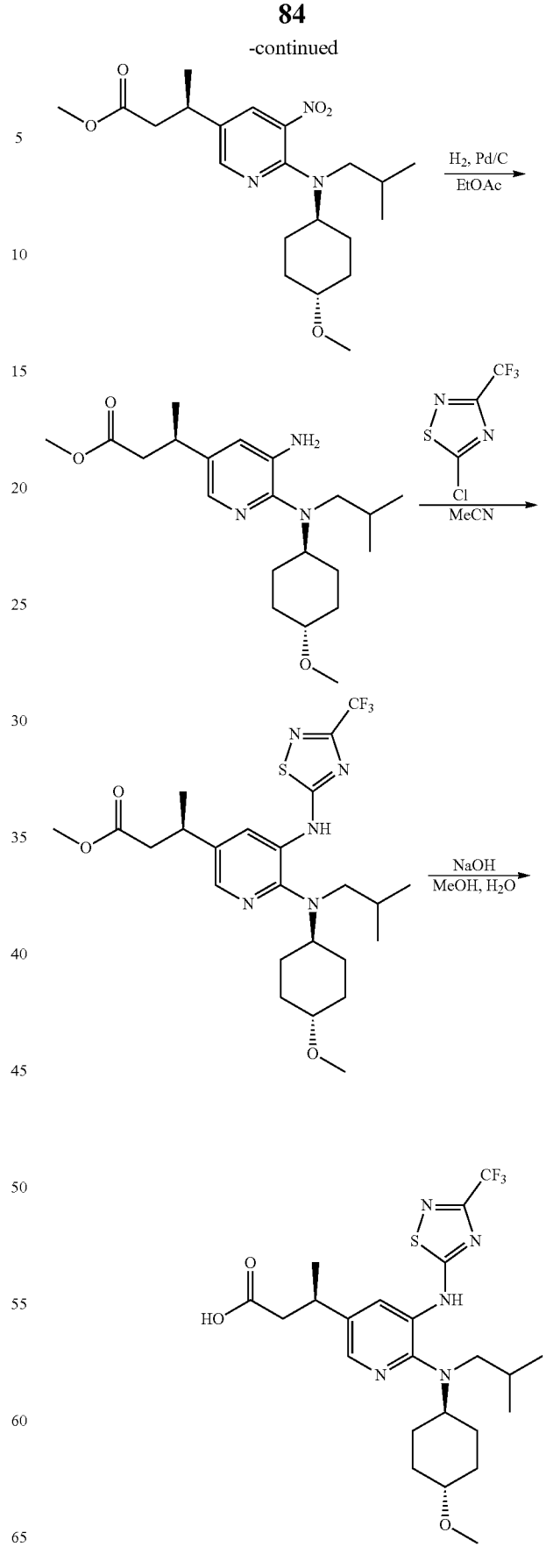

Preparation of (1r,4r)-4-((5-bromo-3-nitropyridin-2-yl)(isobutyl)amino)cyclo hexan-1-ol

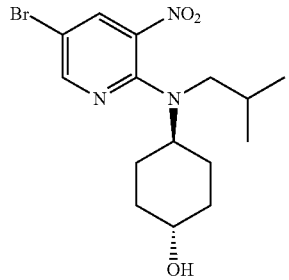 [SMILES: CC(C)CN(c1ncc(Br)cc1[N+](=O)[O-])[C@H]1CC[C@H](O)CC1]

A mixture of 5-bromo-2-fluoro-3-nitropyridine (9.5 g, 40.0 mmol), (1r,4r)-4-(isobutyl amino)cyclohexan-1-ol (10.0 g, 60.0 mmol) and DIPEA (13.9 mL, 80.0 mmol) in NMP (150 mL) was stirred at 130° C. under $N_2$ atmosphere for 6 hr. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (12.3 g, 83% yield) as a red oil. LCMS (ESI) m/z calcd for chemical Formula: $C_{15}H_{22}BrN_3O_3$: 371.08. Found: 372.24/374.24 $(M/M+2)^+$.

Preparation of 5-bromo-N-isobutyl-N-((1r,4r)-4-methoxycyclohexyl)-3-nitropyri din-2-amine

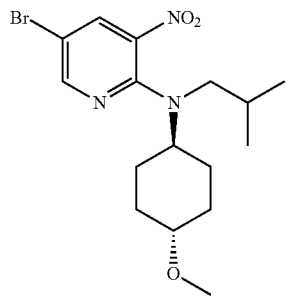 [SMILES: CO[C@H]1CC[C@H](N(CC(C)C)c2ncc(Br)cc2[N+](=O)[O-])CC1]

At 0° C., to a solution of (1r,4r)-4-((5-bromo-3-nitropyridin-2-yl)(isobutyl)amino)cyclo hexan-1-ol (7.2 g, 19.2 mmol) in THF (80 mL) was added NaH (60%, 4.6 g, 115 mmol). The reaction mixture was stirred at 0° C. for 2 hr before the addition of MeI (12 mL, 192 mmol). After stirred at r.t. overnight, the resulting mixture was quenched with sat. $NH_4Cl$ aq. solution and extracted with EtOAc. The organic layer was washed with brine, dried over $Na_2SO_4$, filtered and concentrated to give the crude product which was purified by flash chromatography (silica gel, 0-20% EtOAc in PE) to afford the title compound (4.0 g, 54% yield) as a red oil. LCMS (ESI) m/z calcd for $C_{18}H_{24}BrN_3O_3$: 385.10. Found: 386.41/388.40 $(M/M+2)^+$.

Preparation of methyl (E)-3-(6-(isobutyl((1r,4r)-4-methoxycyclohexyl)amino)-5-nitropyridin-3-yl)but-2-enoate

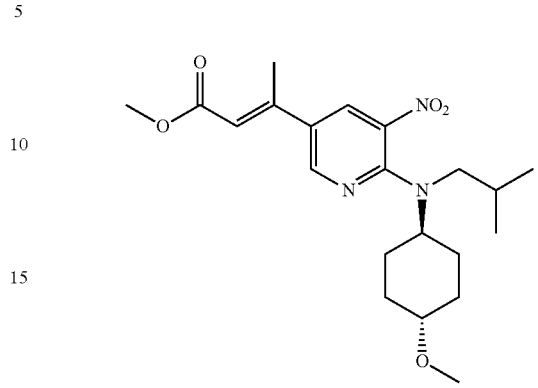

A mixture of 5-bromo-N-isobutyl-N-((1r,4r)-4-methoxycyclohexyl)-3-nitropyri din-2-amine (6.7 g, 17.4 mmol), methyl (E)-but-2-enoate (5.22 g, 52.2 mmol), TBAB (1.12 g, 3.48 mmol), Pd(o-MePh₃P)₄ (684 mg, 0.87 mmol) and TEA (4.87 mL, 34.8 mmol) in DMF (70 mL) was stirred at 100° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (3.9 g, 54% yield) as a red oil. LCMS (ESI) m/z calcd for $C_{21}H_{31}N_3O_5$: 405.23. Found: 406.48 $(M+1)^+$.

Preparation of methyl (R)-3-(6-(isobutyl((1r,4R)-4-methoxycyclohexyl)amino)-5-nitropyridin-3-yl)butanoate

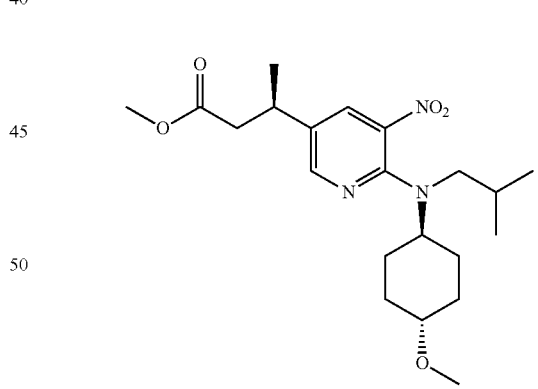

At −5° C., to a mixture of (CuHPh₃P)₆ (353 mg, 0.18 mmol) and (R,S)—PPF—P(tBu)₂ (355 mg, 0.654 mmol) in toluene (50 mL) was added PMHS (1.6 mL) and t-BuOH (1.1 mL) before the introduction of methyl (E)-3-(6-(isobutyl((1r,4r)-4-methoxycyclohexyl) amino)-5-nitropyridin-3-yl)but-2-enoate (3.8 g, 9.3 mmol). After stirred at r.t. overnight, the resulting mixture was quenched with sat. $NaHCO_3$ aq. solution and extracted with EtOAc. The organic layer was washed with brine, dried over $Na_2SO_4$, filtered and concentrated to give the crude product which was purified by flash chromatography (silica gel, 0-20% EtOAc in PE) to afford the title compound (2.8 g, 74% yield) as a yellow oil. LCMS (ESI) m/z calcd for $C_{21}H_{33}N_3O_5$: 407.24. Found: 408.68 (M+1)+.

Preparation of methyl (R)-3-(5-amino-6-(isobutyl ((1r,4R)-4-methoxycyclohexyl) amino)pyridin-3-yl) butanoate

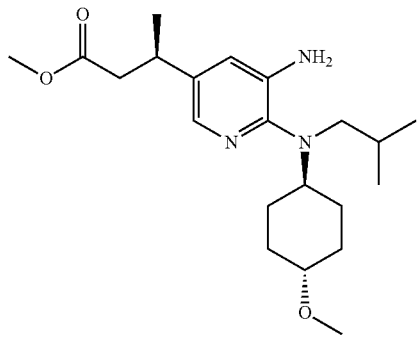 [SMILES: COC(=O)C[C@@H](C)c1cnc(N(CC(C)C)[C@H]2CC[C@H](OC)CC2)c(N)c1]

A mixture of methyl (R)-3-(6-(isobutyl((1r,4R)-4-methoxycyclohexyl)amino)-5-nitropyridin-3-yl)butanoate (2.8 g, 6.88 mmol) and 10% Pd/C (1.4 g) in EtOAc (10 mL) was purged with $H_2$ and stirred at 50° C. for 5 hr. The resulting mixture was filtered through a pad of Celite and the filtrate was concentrated under reduced pressure to give the crude product which was purified by flash chromatography (silica gel, 0-30% EtOAc in PE) to afford the title compound (1.7 g, 66% yield) as a yellow oil. LCMS (ESI) m/z calcd for $C_{21}H_{35}N_3O_3$: 377.27. Found: 378.15 (M+1)+.

Preparation of methyl (R)-3-(6-(isobutyl((1r,4R)-4-methoxycyclohexyl)amino)-5-((3-(trifluoromethyl)-1,2,4-thiadiazol-5-yl)amino)pyridin-3-yl)butanoate

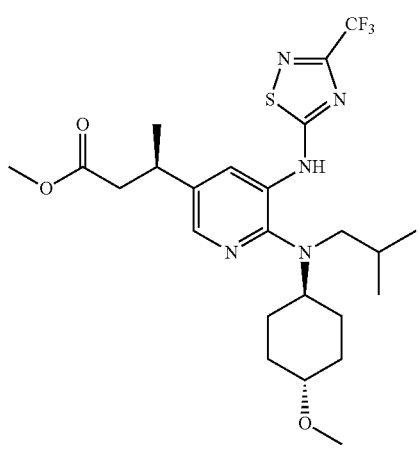 [SMILES: COC(=O)C[C@@H](C)c1cnc(N(CC(C)C)[C@H]2CC[C@H](OC)CC2)c(Nc2nc(C(F)(F)F)ns2)c1]

A mixture of methyl (R)-3-(5-amino-6-(isobutyl((1r,4R)-4-methoxycyclohexyl) amino) pyridin-3-yl)butanoate (100 mg, 0.27 mmol) and 5-chloro-3-(trifluoromethyl)-1,2,4-thiadiazole (101 mg, 0.54 mmol) in MeCN (2 mL) was stirred at 90° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (40 mg, 29% yield). LCMS (ESI) m/z calcd for $C_{24}H_{34}F_3N_5O_3S$: 529.23. Found: 530.49 (M+1)+.

Preparation of (R)-3-(6-(isobutyl((1r,4R)-4-methoxycyclohexyl)amino)-5-((3-(tri fluoromethyl)-1,2,4-thiadiazol-5-yl)amino)pyridin-3-yl)butanoic acid

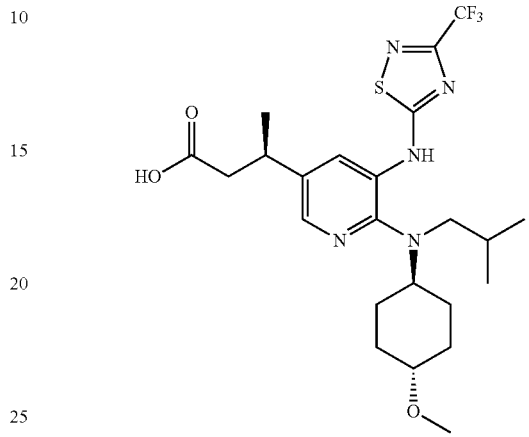

To a solution of methyl (R)-3-(6-(isobutyl((1r,4R)-4-methoxycyclohexyl)amino)-5-((3-(trifluoromethyl)-1,2,4-thiadiazol-5-yl)amino)pyridin-3-yl)butanoate (40 mg, 0.075 mmol) in MeOH (3 mL) was added 4N NaOH aq. (0.5 mL). After stirred at 50° C. for 5 hr, the resulting mixture was neutralized with 1N HCl and extracted with EtOAc. The organic layer was washed with brine, dried over $Na_2SO_4$, filtered and concentrated to give the crude product which was purified by HPLC (C18, 0-100% MeCN in $H_2O$ with 0.1% formic acid) to afford the title compound (19.3 mg, 50% yield) as a white powder. 1H NMR (400 MHz, CDCl3) δ 9.27 (s, 1H), 8.10 (d, J=2.1 Hz, 1H), 7.90 (d, J=1.9 Hz, 1H), 3.42-3.34 (m, 1H), 3.30 (s, 3H), 3.08-2.94 (m, 3H), 2.80-2.66 (m, 3H), 2.11-2.03 (m, 2H), 1.92-1.83 (m, 2H), 1.48-1.26 (m, 8H), 0.83 (d, J=6.6 Hz, 6H).). LCMS (ESI) m/z calcd for $C_{23}H_{32}F_3N_5O_3S$: 515.22. Found: 516.47 (M+1)+.

Example 27

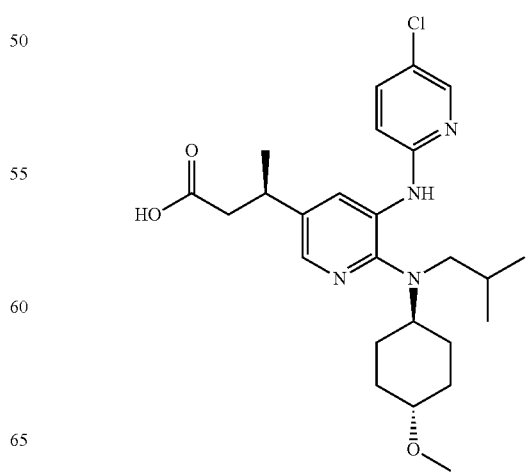

-continued

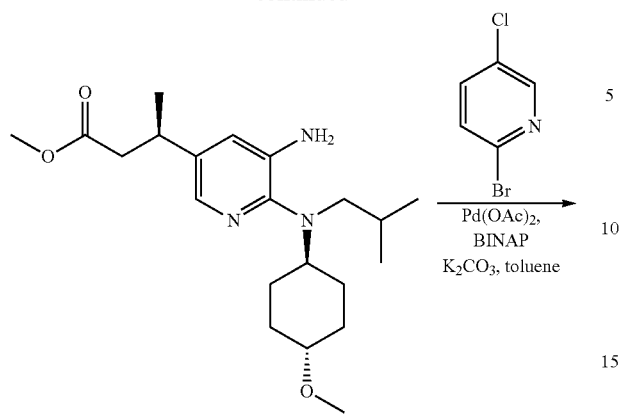

Preparation of methyl (R)-3-(5-((5-chloropyridin-2-yl)amino)-6-(isobutyl((1r,4R)-4-methoxycyclohexyl)amino)pyridin-3-yl)butanoate

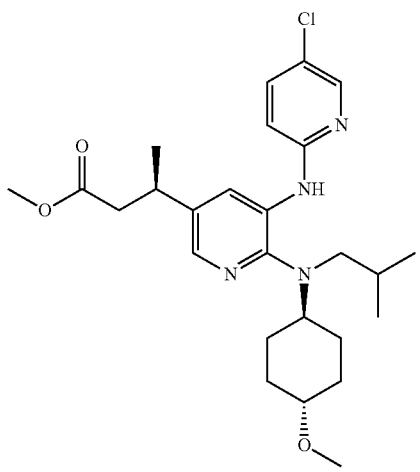 [SMILES: COC(=O)C[C@@H](C)c1cnc(N(CC(C)C)[C@H]2CC[C@H](OC)CC2)c(Nc2ccc(Cl)cn2)c1]

A mixture of methyl (R)-3-(5-amino-6-(isobutyl((1r,4R)-4-methoxycyclohexyl)amino) pyridin-3-yl)butanoate (100 mg, 0.27 mmol), 2-bromo-5-chloropyridine (104 mg, 0.54 mmol), Pd(OAc)$_2$ (2.6 mg, 0.0043 mmol), BINAP (3.1 mg, 0.0049 mmol) and K$_2$CO$_3$ (112 mg, 0.81 mmol) in toluene (2 mL) was stirred at 130° C. under N$_2$ atmosphere overnight. The resulting mixture was partitioned between EtOAc and H$_2$O. The organic layer was washed with brine, dried over Na$_2$SO$_4$, filtered and concentrated to give the crude product which was purified by flash chromatography (silica gel, 0-30% EtOAc in PE) to afford the title compound (80 mg, 62% yield). LCMS (ESI) m/z calcd for C$_{26}$H$_{37}$ClN$_4$O$_3$: 488.26. Found: 489.38/491.10 (M/M+2)$^+$.

Preparation of (R)-3-(5-((5-chloropyridin-2-yl)amino)-6-(isobutyl((1r,4R)-4-methoxycyclohexyl)amino)pyridin-3-yl)butanoic acid

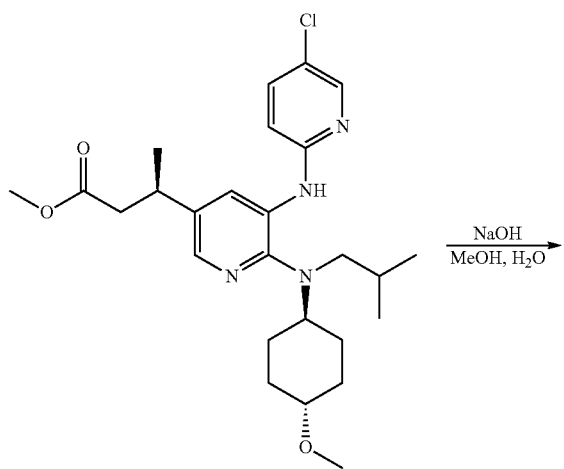

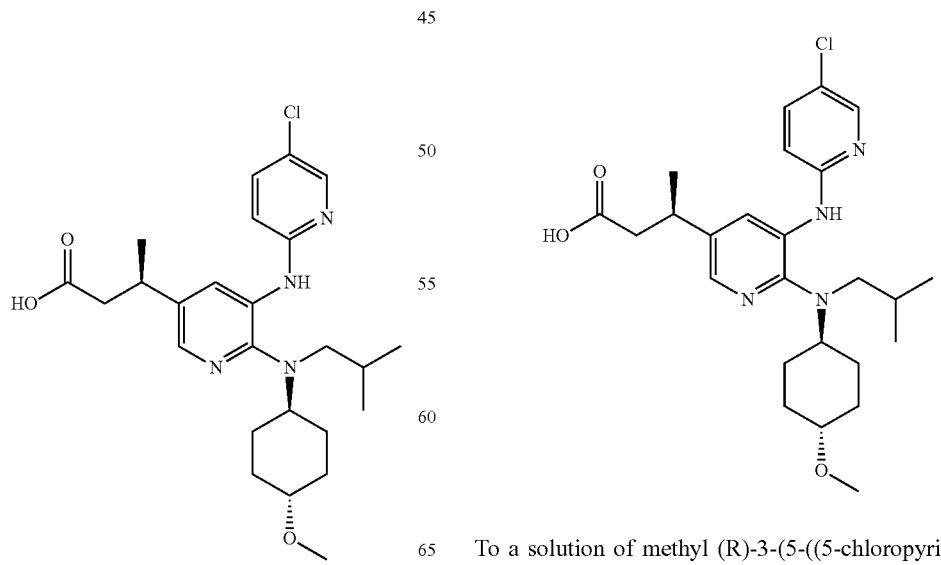

To a solution of methyl (R)-3-(5-((5-chloropyridin-2-yl)amino)-6-(isobutyl((1r,4R)-4-methoxycyclohexyl)amino) pyridin-3-yl)butanoate (80 mg, 0.164 mmol) in MeOH (3 mL) was added 4N NaOH aq. (0.5 mL). After stirred at r.t for 7 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (45 mg, 58% yield) as a white powder. $^1$H NMR (400 MHz, CDCl$_3$) δ 8.48 (s, 1H), 8.22 (d, J=2.4 Hz, 1H), 7.91 (d, J=1.9 Hz, 1H), 7.71 (s, 1H), 7.49 (dd, J=8.8, 2.5 Hz, 1H), 6.66 (d, J=8.8 Hz, 1H), 3.36-3.24 (m, 4H), 3.09-2.92 (m, 3H), 2.82-2.61 (m, 3H), 2.08-1.99 (m, 2H), 1.91-1.83 (m, 2H), 1.52-1.34 (m, 6H), 1.16-1.05 (m, 2H), 0.84 (d, J=6.6 Hz, 6H). LCMS (ESI) m/z calcd for C$_{25}$H$_{35}$ClN$_4$O$_3$: 474.24. Found: 475.20/477.57 (M/M+2)$^+$.

Example 28

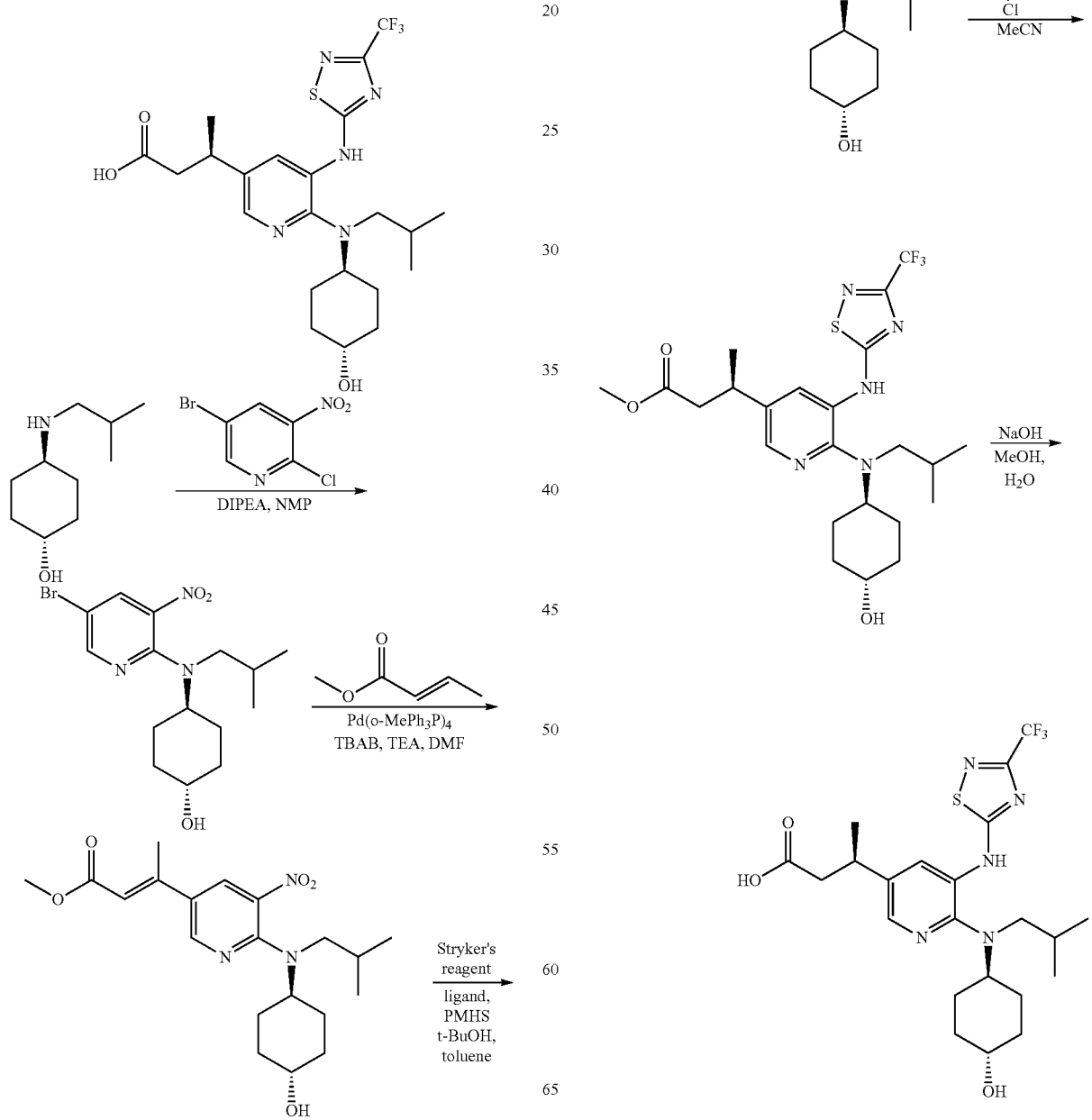

Preparation of (1r,4r)-4-((5-bromo-3-nitropyridin-2-yl)(isobutyl)amino)cyclo hexan-1-ol

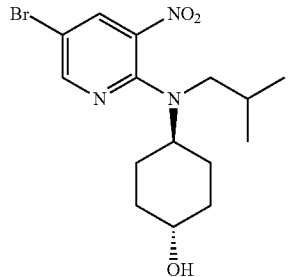 [SMILES: CC(C)CN(c1ncc(Br)cc1[N+](=O)[O-])[C@H]1CC[C@H](O)CC1]

A mixture of 5-bromo-2-chloro-3-nitropyridine (10 g, 42.1 mmol), (1r,4r)-4-(isobutyl amino)cyclohexan-1-ol (14 g, 84.2 mmol) and DIPEA (16 g, 12.6 mmol) in NMP (100 mL) was stirred at 140° C. under $N_2$ atmosphere for 6 hr. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (9 g, 62% yield) as a red oil. LCMS (ESI) m/z calcd for chemical Formula: $C_{15}H_{22}BrN_3O_3$: 371.08. Found: 372.21/374.19 (M/M+2)$^+$.

Preparation of methyl (E)-3-(6-(((1r,4r)-4-hydroxycyclohexyl)(isobutyl)amino)-5-nitropyridin-3-yl)but-2-enoate

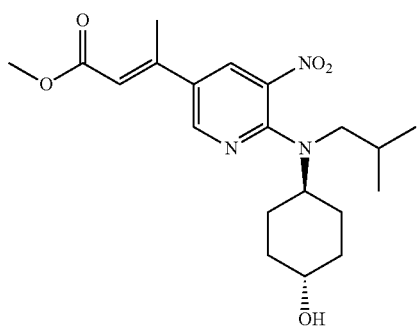 [SMILES: COC(=O)/C=C(\C)c1cnc(N(CC(C)C)[C@H]2CC[C@H](O)CC2)c([N+](=O)[O-])c1]

A mixture of (1r,4r)-4-((5-bromo-3-nitropyridin-2-yl)(isobutyl)amino)cyclohexan-1-ol (500 mg, 1.34 mmol), methyl (E)-but-2-enoate (403 mg, 4.03 mmol), TBAB (87 mg, 0.269 mmol), Pd(o-MePh$_3$P)$_4$ (131 mg, 0.27 mmol) and TEA (270 mg, 2.68 mmol) in DMF (5 mL) was stirred at 110° C. under $N_2$ atmosphere overnight. The resulting mixture was partitioned between EtOAc and $H_2O$. The layers were separated and the organic layer was washed with brine, dried over $Na_2SO_4$, filtered and concentrated to give the crude product which was purified by flash chromatography (silica gel, 0-20% EtOAc in PE) to afford the title compound (220 mg, 32% yield). LCMS (ESI) m/z calcd for $C_{20}H_{29}N_3O_5$: 391.21. Found: 392.27 (M+1)$^+$.

Preparation of methyl (R)-3-(6-(((1r,4R)-4-hydroxycyclohexyl)(isobutyl)amino)-5-nitropyridin-3-yl)butanoate

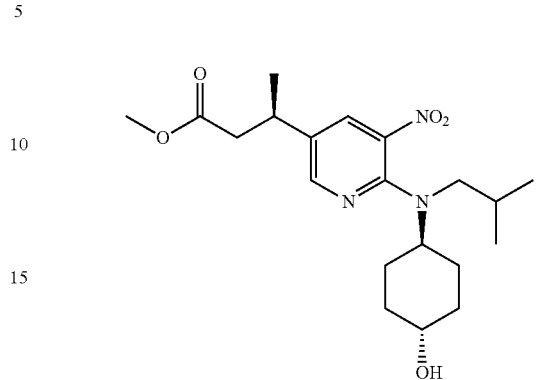

At −5° C., to a mixture of (CuHPh$_3$P)$_6$ (103 mg, 0.0527 mmol) and (R,S)—PPF—P(tBu)$_2$ (104 mg, 0.192 mmol) in toluene (13 mL) was added PMHS (0.27 mL) and t-BuOH (0.2 mL) before the introduction of methyl (E)-3-(6-(((1r,4r)-4-hydroxycyclohexyl) (isobutyl)amino)-5-nitropyridin-3-yl)but-2-enoate (670 mg, 1.71 mmol). After stirred at −5° C. for 4 hr, the resulting mixture was quenched with sat. NaHCO$_3$ aq. solution and extracted with EtOAc. The organic layer was washed with brine, dried over $Na_2SO_4$, filtered and concentrated to give the crude product which was purified by flash chromatography (silica gel, 0-20% EtOAc in PE) to afford the title compound (100 mg, 15% yield). LCMS (ESI) m/z calcd for $C_{20}H_{31}N_3O_5$: 393.23. Found: 394.40 (M+1)$^+$.

Preparation of methyl (R)-3-(5-amino-6-(((1r,4R)-4-hydroxycyclohexyl)(isobutyl) amino)pyridin-3-yl)butanoate

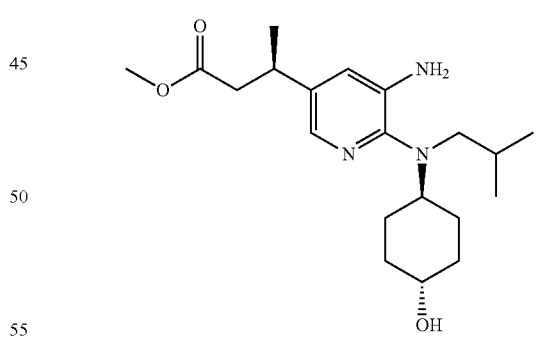

A mixture of methyl (R)-3-(6-(((1r,4R)-4-hydroxycyclohexyl)(isobutyl)amino)-5-nitropyridin-3-yl)butanoate (110 mg, 0.27 mmol) and 10% Pd/C (100 mg) in EtOAc (3 mL) was purged with $H_2$ and stirred at 50° C. for 2 hr. The resulting mixture was filtered through a pad of Celite and the filtrate was concentrated under reduced pressure to give the crude product which was purified by flash chromatography (silica gel, 0-30% EtOAc in PE) to afford the title compound (90 mg, 84% yield). LCMS (ESI) m/z calcd for $C_{20}H_{33}N_3O_3$: 363.25. Found: 364.48 (M+1)$^+$.

Preparation of methyl (R)-3-(6-(((1r,4R)-4-hydroxy-cyclohexyl)(isobutyl)amino)-5-((3-(trifluoromethyl)-1,2,4-thiadiazol-5-yl)amino)pyridin-3-yl)butanoate

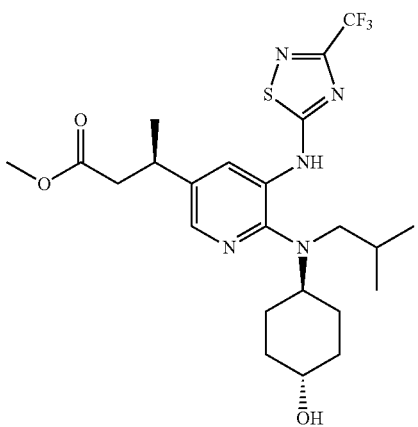 [SMILES: COC(=O)C[C@@H](C)c1cnc(N(CC(C)C)[C@H]2CC[C@H](O)CC2)c(Nc2nc(C(F)(F)F)ns2)c1]

A mixture of methyl (R)-3-(5-amino-6-(((1r,4R)-4-hydroxycyclohexyl)(isobutyl) amino)pyridin-3-yl)butanoate (90 mg, 0.247 mmol) and 5-chloro-3-(trifluoromethyl)-1,2,4-thiadiazole (93 mg, 0.49 mmol) in MeCN (2 mL) was stirred at 90° C. under N₂ atmosphere overnight. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-30% EtOAc in PE) to afford the title compound (42 mg, 33% yield). LCMS (ESI) m/z calcd for $C_{23}H_{32}F_3N_5O_3S$: 515.22. Found: 516.60 (M+1)⁺.

Preparation of (R)-3-(6-(((1r,4R)-4-hydroxycyclohexyl)(isobutyl)amino)-5-((3-(trifluoromethyl)-1,2,4-thiadiazol-5-yl)amino)pyridin-3-yl)butanoic acid

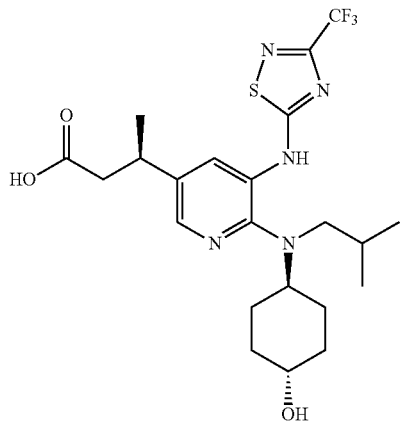 [SMILES: CC(C)CN(c1ncc([C@H](C)CC(=O)O)cc1Nc1nc(C(F)(F)F)ns1)[C@H]1CC[C@H](O)CC1]

To a solution of methyl (R)-3-(6-(((1r,4R)-4-hydroxycyclohexyl)(isobutyl)amino)-5-((3-(trifluoromethyl)-1,2,4-thiadiazol-5-yl)amino)pyridin-3-yl)butanoate (42 mg, 0.0815 mmol) in MeOH (3 mL) was added 4N NaOH aq. (0.5 mL). After stirred at r.t overnight, the resulting mixture was neutralized with 1N HCl and extracted with EtOAc. The organic layer was washed with brine, dried over Na₂SO₄, filtered and concentrated to give the crude product which was purified by HPLC (C18, 0-100% MeCN in H₂O with 0.1% formic acid) to afford the title compound (27 mg, 68% yield) as a white powder. ¹H NMR (400 MHz, CDCl₃) δ 9.00 (s, 1H), 8.09 (d, J=2.1 Hz, 1H), 7.89 (d, J=1.9 Hz, 1H), 3.57-3.51 (m, 1H), 3.41-3.34 (m, 1H), 2.97 (d, J=7.0 Hz, 2H), 2.78-2.67 (m, 3H), 2.01-1.96 (m, 2H), 1.88-1.84 (m, 2H), 1.51-1.35 (m, 7H), 1.27-1.19 (m, 2H), 0.83 (d, J=6.6 Hz, 6H). LCMS (ESI) m/z calcd for $C_{22}H_{30}F_3N_5O_3S$: 501.20. Found: 500.49 (M−1)⁻.

Example 29

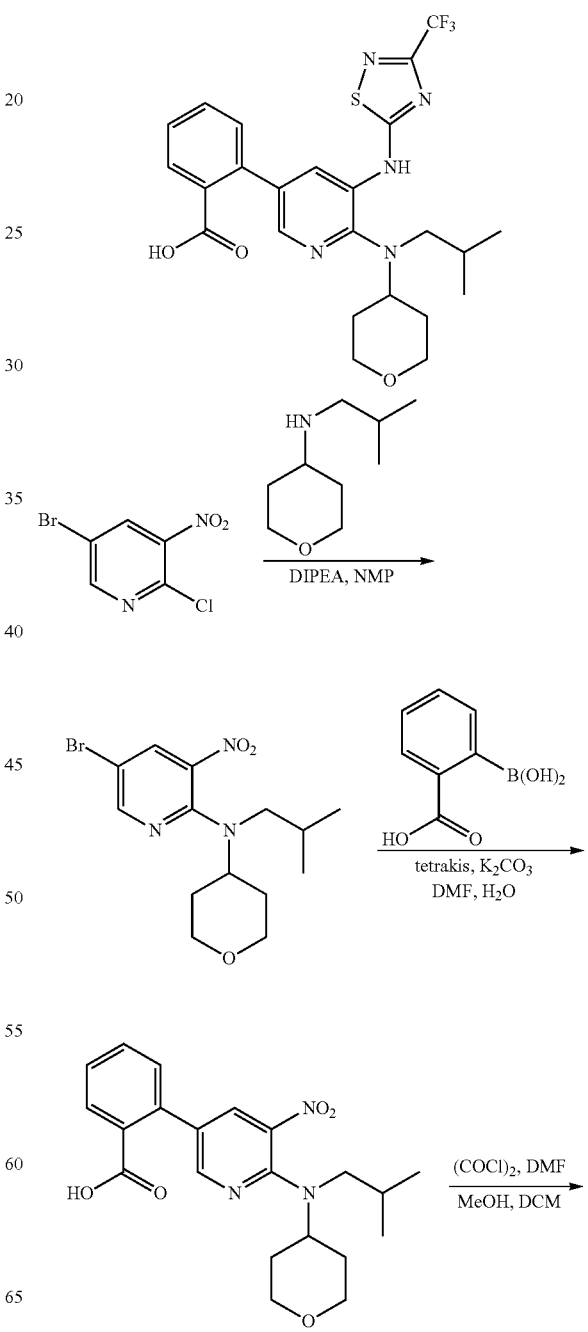

-continued

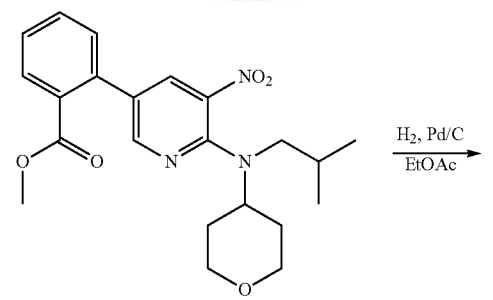

H₂, Pd/C
EtOAc

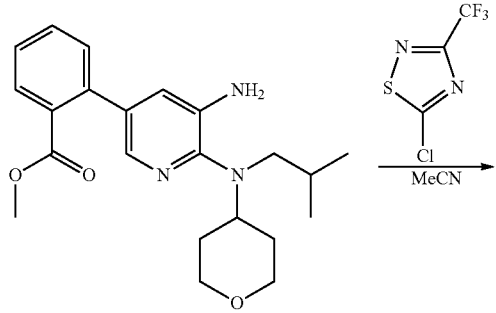

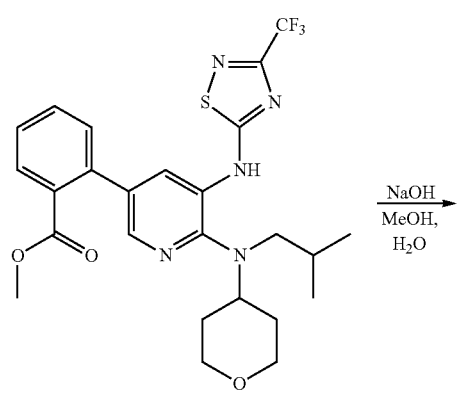

NaOH
MeOH,
H₂O

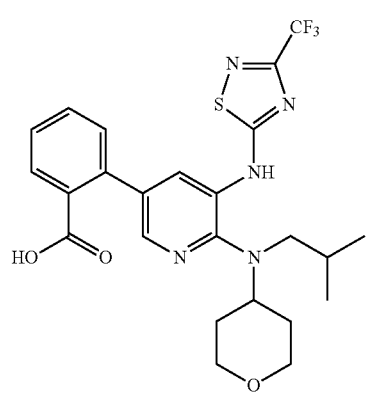

Preparation of 5-bromo-N-isobutyl-3-nitro-N-(tetrahydro-2H-pyran-4-yl)pyridin-2-amine

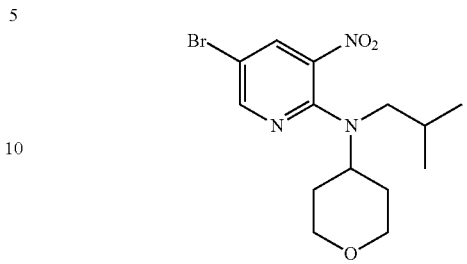

A mixture of 5-bromo-2-chloro-3-nitropyridine (15.3 g, 64.5 mmol), N-isobutyltetra hydro-2H-pyran-4-amine (15.2 g, 96.7 mmol) and DIPEA (22.5 mL, 129 mmol) in NMP (150 mL) was stirred at 140° C. for 4 hr. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-10% EtOAc in PE) to afford the title compound (9.7 g, 42% yield). LCMS (ESI) m/z calcd for $C_{14}H_{20}BrN_3O_3$: 357.07. Found: 358.24/360.22 (M/M+2)⁺.

Preparation of 2-(6-(isobutyl(tetrahydro-2H-pyran-4-yl)amino)-5-nitropyridin-3-yl) benzoic acid

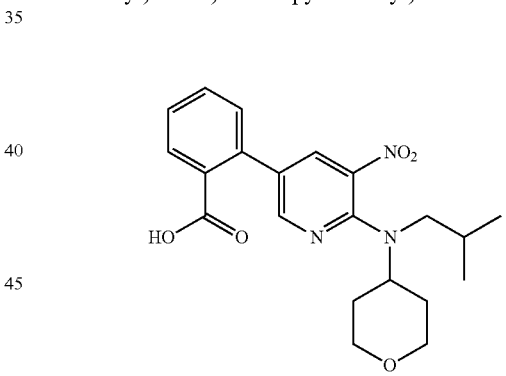

A mixture of 5-bromo-N-isobutyl-3-nitro-N-(tetrahydro-2H-pyran-4-yl)pyridin-2-amine (300 mg, 0.838 mmol), 2-boronobenzoic acid (208 mg, 1.257 mmol), tetrakis (77 mg, 0.067 mmol) and K₂CO₃ (232 mg, 1.676 mmol) in DMF (8 mL) and H₂O (1 mL) was stirred at 110° C. under N₂ atmosphere overnight. The resulting mixture was partitioned between EtOAc and H₂O. The layers were separated and the organic layer was washed with brine, dried over Na₂SO₄, filtered and concentrated to give the crude product which was purified by flash chromatography (silica gel, 0-5% MeOH in DCM) to afford the title compound (320 mg, 96% yield). LCMS (ESI) m/z calcd for $C_{21}H_{25}N_3O_5$: 399.18. Found: 400.27 (M+1)⁺.

Preparation of methyl 2-(6-(isobutyl(tetrahydro-2H-pyran-4-yl)amino)-5-nitro pyridin-3-yl)benzoate

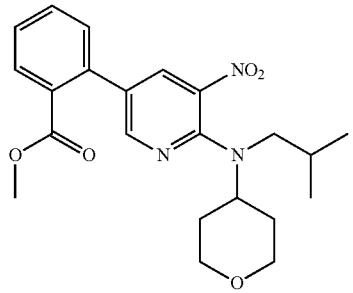 [SMILES: COC(=O)c1ccccc1-c1cnc(N(CC(C)C)C2CCOCC2)c([N+](=O)[O-])c1]

At 0° C., to a suspension of 2-(6-(isobutyl(tetrahydro-2H-pyran-4-yl)amino)-5-nitropyri din-3-yl) benzoic acid (1.44 g, 3.67 mmol) in DCM (15 mL) was added (COCl)$_2$ (0.61 mL, 7.21 mmol) and 1 drop DMF. The reaction mixture was stirred at r.t. for 5 hr before the addition of MeOH (10 mL). After stirred at r.t. for 1 hr, the resulting mixture was quenched with H$_2$O and extracted with DCM. The organic layer was washed with brine, dried over Na$_2$SO$_4$, filtered and concentrated to give the crude product which was purified by flash chromatography (silica gel, 0-20% EtOAc in PE) to afford the title compound (1.2 g, 81% yield). LCMS (ESI) m/z calcd for C$_{22}$H$_{27}$N$_3$O$_5$: 413.20. Found: 414.31 (M+1)$^+$.

Preparation of methyl 2-(5-amino-6-(isobutyl(tetrahydro-2H-pyran-4-yl)amino) pyridin-3-yl)benzoate

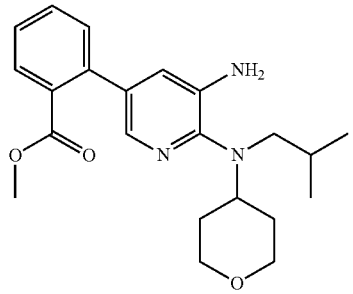 [SMILES: COC(=O)c1ccccc1-c1cnc(N(CC(C)C)C2CCOCC2)c(N)c1]

A mixture of methyl 2-(6-(isobutyl(tetrahydro-2H-pyran-4-yl)amino)-5-nitropyridin-3-yl) benzoate (800 mg, 1.93 mmol) and 10% Pd/C (240 mg) in EtOAc (10 mL) was stirred at 50° C. under H$_2$ atmosphere for 4 hr. The resulting mixture was filtered through a pad of Celite and the filtrate was concentrated under reduced pressure to give the crude product which was purified by flash chromatography (silica gel, 0-40% EtOAc in PE) to afford the title compound (520 mg, 70% yield) as a colorless oil. LCMS (ESI) m/z calcd for C$_{22}$H$_{29}$N$_3$O$_3$: 383.22. Found: 384.55 (M+1)$^+$.

Preparation of methyl 2-(6-(isobutyl(tetrahydro-2H-pyran-4-yl)amino)-5-((3-(trifluoromethyl)-1,2,4-thiadiazol-5-yl)amino)pyridin-3-yl)benzoate

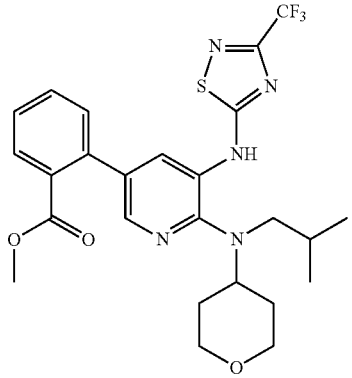 [SMILES: COC(=O)c1ccccc1-c1cnc(N(CC(C)C)C2CCOCC2)c(Nc2nc(C(F)(F)F)ns2)c1]

A mixture of methyl 2-(5-amino-6-(isobutyl(tetrahydro-2H-pyran-4-yl)amino)pyridin-3-yl)benzoate (70 mg, 0.183 mmol) and 5-chloro-3-(trifluoromethyl)-1,2,4-thiadiazole (52 mg, 0.275 mmol) in MeCN (3 mL) was stirred at 90° C. under N$_2$ atmosphere for a week. The resulting mixture was partitioned between EtOAc and H$_2$O. The layers were separated and the organic layer was washed with brine, dried over Na$_2$SO$_4$, filtered and concentrated to give the crude product which was purified by flash chromatography (silica gel, 0-40% EtOAc in PE) to afford the title compound (17 mg, 17% yield). LCMS (ESI) m/z calcd for C$_{25}$H$_{28}$F$_3$N$_5$O$_3$S: 535.19. Found: 536.61 (M+1)$^+$.

Preparation of 2-(6-(isobutyl(tetrahydro-2H-pyran-4-yl)amino)-5-((3-(trifluoro methyl)-1,2,4-thiadiazol-5-yl)amino)pyridin-3-yl)benzoic acid

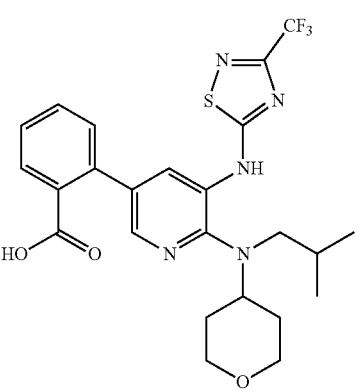 [SMILES: CC(C)CN(c1ncc(-c2ccccc2C(=O)O)cc1Nc1nc(C(F)(F)F)ns1)C1CCOCC1]

To a solution of methyl 2-(6-(isobutyl(tetrahydro-2H-pyran-4-yl)amino)-5-((3-(trifluoro methyl)-1,2,4-thiadiazol-5-yl)amino)pyridin-3-yl)benzoate (17 mg, 0.03 mmol) in MeOH (3 mL) was added 4N NaOH aq. (0.5 mL). After stirred at 50° C. for 24 hr, the resulting mixture was neutralized with 1N HCl and extracted with EtOAc. The organic layer was washed with brine, dried over Na$_2$SO$_4$, filtered and concentrated to give the crude product which was purified by HPLC (C18, 0-100% MeCN in H$_2$O with 0.1% formic acid) to afford the title compound (11 mg, 68% yield) as a white powder. $^1$H NMR (400 MHz, CDCl$_3$) δ

9.59 (s, 1H), 8.21 (d, J=2.1 Hz, 1H), 8.12 (dd, J=7.8, 1.0 Hz, 1H), 7.84 (d, J=1.9 Hz, 1H), 7.71-7.62 (m, 1H), 7.53 (t, J=7.1 Hz, 1H), 7.44 (d, J=6.9 Hz, 1H), 3.99-3.87 (m, 2H), 3.26-2.94 (m, 5H), 1.80-1.44 (m, 5H), 0.79 (d, J=6.6 Hz, 6H). LCMS (ESI) m/z calcd for $C_{24}H_{26}F_3N_5O_3S$: 521.17. Found: 522.32 $(M+1)^+$.

Example 30

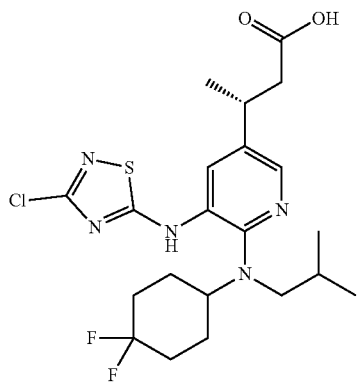 [SMILES: CC(C)CN(c1ncc([C@H](C)CC(=O)O)cc1Nc1nc(Cl)ns1)C1CCC(F)(F)CC1]

Preparation of (R)-3-(5-((3-chloro-1,2,4-thiadiazol-5-yl)amino)-6-((4,4-difluorocyclohexyl)(isobutyl)amino)pyridin-3-yl)butanoic acid Ethyl (R)-3-(5-amino-6-((4,4-difluorocyclohexyl)(isobutyl)amino)amino)pyridin-3-yl)butanoate (49 mg, 0.12 mmol), N-ethyl-N-isopropylpropan-2-amine (0.064 mL, 0.37 mmol), and 3,5-dichloro-1,2,4-thiadiazole (22.9 mg, 0.148 mmol) in acetonitrile (1 mL) were heated at 90° C. overnight in a sealed reaction vial. LC-MS showed starting material and the bis-arylated product. Additional 3,5-dichloro-1,2,4-thiadiazole (75 mg) starting material was added along with additional N-ethyl-N-isopropylpropan-2-amine (0.064 mL, 0.37 mmol). The mixture was continued to heat at 90° C. for 6 hours. The mixture was allowed to cool to room temperature and then injected onto a medium pressure reverse phase chromatography column. Elution with a gradient of 10% to 100% acetonitrile/water/0.1% formic acid followed by concentration of eluted peaks gave ethyl (R)-3-(5-(bis(3-chloro-1,2,4-thiadiazol-5-yl)amino)-6-((4,4-difluorocyclohexyl)(isobutyl)amino)pyridin-3-yl)butanoate (40 mg, 0.063 mmol, 51% yield). LCMS (ESI) m/z calculated for $C_{25}H_{31}Cl_2F_2N_7O_2S_2$: 633.13. Found: 634.58, 636.52, 638.31 (M+H)+.

1M Sodium hydroxide (0.63 mL, 0.63 mmol) was added to a solution of ethyl (R)-3-(5-(bis(3-chloro-1,2,4-thiadiazol-5-yl)amino)-6-((4,4-difluorocyclohexyl)(isobutyl)amino)pyridin-3-yl)butanoate (40 mg, 0.063 mmol) in tert-butanol (1 mL) and the mixture was stirred at 60° C. for 4 hours. The mixture was concentrated and the residue purified by reverse phase medium pressure chromatography (10% to 100% acetonitrile/water/0.1% formic acid). Fractions were concentrated until only water remained and then the mixture lyophilized to give (R)-3-(5-((3-chloro-1,2,4-thiadiazol-5-yl)amino)-6-((4,4-difluorocyclohexyl)(isobutyl)amino)pyridin-3-yl)butanoic acid (21 mg, 0.043 mmol, 68% yield) as a white solid. LCMS (ESI) m/z calculated for $C_{21}H_{28}ClF_2N_5O_2S$: 487.16. Found: 488.34, 490.27 (M+H)+. 1H NMR (400 MHz, METHANOL-d4) δ ppm 0.82 (d, J=6.59 Hz, 6H) 1.35 (d, J=6.96 Hz, 3H) 1.42-1.55 (m, 1H) 1.59-1.80 (m, 4H) 1.81-1.91 (m, 2H) 1.97-2.11 (m, 2H) 2.62 (d, J=7.33 Hz, 2H) 3.00 (d, J=6.59 Hz, 2H) 3.09-3.21 (m, 1H) 3.26-3.31 (m, 1H) 8.07 (s, 1H) 8.26 (s, 1 H).

Examples 31-84 were synthesized similarly to examples 1-30.

HPLC retention times and observed mass spec data listed below.

| | | IPQA $T_{elute}$ [min] | M + 1 | M − 1 |
|---|---|---|---|---|
| example 31 | 3-{6-[(2-methylpropyl)(oxan-4-yl)amino]-5-{[3-(trifluoromethyl)-1,2,4-thiadiazol-5-yl]amino}pyridin-3-yl}butanoic acid | 1.16 | 488.4 | |
| example 32 | 3-{6-[bis(2-methylpropyl)amino]-5-[(3-chloro-1,2,4-thiadiazol-5-yl)amino]pyridin-3-yl}butanoic acid | 1.19 | | 424.3 |
| example 33 | 3-{5-[(5-cyanopyridin-2-yl)amino]-6-[(2-methylpropyl)(oxan-4-yl)amino]pyridin-3-yl}butanoic acid | 0.92 | | 436.3 |
| example 34 | 3-{5-[(3-chloro-1,2,4-thiadiazol-5-yl)amino]-6-[(2-methylpropyl)(oxan-4-yl)amino]pyridin-3-yl}butanoic acid | 1.06 | 454.3 | |
| example 35 | 3-{5-[(5-chloropyridin-2-yl)amino]-6-[(2-methylpropyl)(oxan-4-yl)amino]pyridin-3-yl}butanoic acid | 1.04 | | 445.2 |
| example 36 | 3-{5-[(5-cyclopropyl-1,3,4-thiadiazol-2-yl)amino]-6-[(2-methylpropyl)(oxan-4-yl)amino]pyridin-3-yl}butanoic acid | 1.95 | | 458.3 |
| example 37 | 3-{5-[(3-cyclopropyl-1,2,4-thiadiazol-5-yl)amino]-6-[(2-methylpropyl)(oxan-4-yl)amino]pyridin-3-yl}butanoic acid | 1.09 | | 458.3 |
| example 38 | (3R)-3-{5-[(5-cyclopropyl-1,3,4-thiadiazol-2-yl)amino]-6-[(2-methylpropyl)(oxan-4-yl)amino]pyridin-3-yl}butanoic acid | 0.95 | | 458.3 |
| example 39 | (3R)-3-{5-[(3-chloro-1,2,4-thiadiazol-5-yl)amino]-6-[(2-methylpropyl)(oxan-4-yl)amino]pyridin-3-yl}butanoic acid | 1.07 | 454.3 | |
| example 40 | (3R)-3-{6-[bis(2-methylpropyl)amino]-5-{[3-(trifluoromethyl)-1,2,4-thiadiazol-5-yl]amino}pyridin-3-yl}butanoic acid | 1.28 | 460.8 | |
| example 41 | (3R)-3-{5-[(3-cyclopropyl-1,2,4-thiadiazol-5-yl)amino]-6-[(2-methylpropyl)(oxan-4-yl)amino]pyridin-3-yl}butanoic acid | 1.08 | 460.2 | |
| example 42 | (3R)-3-{6-[(2-methylpropyl)(oxan-4-yl)amino]-5-{[5-(trifluoromethyl)-1H-1,2,4-triazol-3-yl]amino}pyridin-3-yl}butanoic acid | 0.95 | 941.4 | |

-continued

HPLC retention times and observed mass spec data listed below.

| | | IPQA $T_{elute}$ [min] | M + 1 | M − 1 |
|---|---|---|---|---|
| example 43 | (3R)-3-{5-[(5-cyano-1H-1,2,4-triazol-3-yl)amino]-6-[(2-methylpropyl)(oxan-4-yl)amino]pyridin-3-yl}butanoic acid | 0.88 | | 426.3 |
| example 44 | (3R)-3-{5-[(5-carbamoyl-1H-1,2,4-triazol-3-yl)amino]-6-[(2-methylpropyl)(oxan-4-yl)amino]pyridin-3-yl}butanoic acid | 0.68 | 446.03 | |
| example 45 | (3R)-3-{6-[cyclohexyl(2-methylpropyl)amino]-5-[(5-methyl-1,3,4-thiadiazol-2-yl)amino]pyridin-3-yl}butanoic acid | 1.02 | 432.3 | |
| example 46 | (3RS)-3-{5-[(3-chloro-1,2,4-thiadiazol-5-yl)amino]-6-[(2-methylpropyl)[(1rs&,4rs&)-4-methoxycyclohexyl]amino]pyridin-3-yl}butanoic acid | 1.14 | 482.2 | |
| example 47 | (3RS)-3-(5-{[5-(methoxymethyl)pyridin-2-yl]amino}-6-[(2-methylpropyl)[(1rs&,4rs&)-4-methoxycyclohexyl]amino]pyridin-3-yl)butanoic acid | 0.87 | 485.3 | |
| example 48 | (3R)-3-{6-[(2-methylpropyl)(oxan-4-yl)amino]-5-{[4-(trifluoromethyl)-1H-imidazol-2-yl]amino}pyridin-3-yl}butanoic acid | 0.90 | 470.33 | |
| example 49 | (3R)-3-(5-{[5-(methoxymethyl)-1,3,4-thiadiazol-2-yl]amino}-6-[(2-methylpropyl)(oxan-4-yl)amino]pyridin-3-yl)butanoic acid | 0.88 | 464.3 | |
| example 50 | (3R)-3-(5-{[4-(methoxycarbonyl)-1H-imidazol-2-yl]amino}-6-[(2-methylpropyl)(oxan-4-yl)amino]pyridin-3-yl)butanoic acid | 0.72 | 460.2 | 458.3 |
| example 51 | (3R)-3-{6-[bis(2-methylpropyl)amino]-5-{[5-(trifluoromethyl)-1,3,4-thiadiazol-2-yl]amino}pyridin-3-yl}butanoic acid | 0.93 | 460.4 | |
| example 52 | (3R)-3-{6-[(2-methylpropyl)(oxan-4-yl)amino]-5-{[5-(trifluoromethyl)pyridin-2-yl]amino}pyridin-3-yl}butanoic acid | 1.12 | 481.4 | 479.3 |
| example 53 | (3RS)-3-{5-[(5-cyanopyridin-2-yl)amino]-6-[(2-methylpropyl)[(1rs&,4rs&)-4-methoxycyclohexyl]amino]pyridin-3-yl}butanoic acid | 0.98 | 466.4 | 464.4 |
| example 54 | (3R)-3-{6-[bis(2-methylpropyl)amino]-5-{[3-(propan-2-yl)-1,2,4-thiadiazol-5-yl]amino}pyridin-3-yl}butanoic acid | 1.28 | 434.5 | 432.3 |
| example 55 | (3R)-3-[6-({2-[(tert-butoxy)carbonyl]-2-azaspiro[3.3]heptan-6-yl}(2-methylpropyl)amino)-5-[2-(4-methylphenyl)acetamido]pyridin-3-yl]butanoic acid | 1.35 | 579.3 | |
| example 56 | (3R)-3-(5-{[3-(methoxymethyl)-1,2,4-thiadiazol-5-yl]amino}-6-[(2-methylpropyl)(oxan-4-yl)amino]pyridin-3-yl)butanoic acid | 0.92 | 464.1 | 462.4 |
| example 57 | (3R)-3-{5-[(5-cyanopyridin-2-yl)amino]-6-[(2-methylpropyl)(oxan-4-yl)amino]pyridin-3-yl}butanoic acid | 0.93 | 438.4 | |
| example 58 | (3R)-3-(5-{[5-(methoxymethyl)pyridin-2-yl]amino}-6-[(2-methylpropyl)[(1s,4s)-4-methoxycyclohexyl]amino]pyridin-3-yl)butanoic acid | 0.86 | 485.5 | |
| example 59 | (3RS)-3-{6-[(2-methylpropyl)[(1rs&,4rs&)-4-hydroxycyclohexyl]amino]-5-{[3-(trifluoromethyl)-1,2,4-thiadiazol-5-yl]amino}pyridin-3-yl}butanoic acid | 1.04 | 502.4 | 500.4 |
| example 60 | (3R)-3-{5-[(6-chloropyridazin-3-yl)amino]-6-[(2-methylpropyl)(oxan-4-yl)amino]pyridin-3-yl}butanoic acid | 0.88 | 448.1 | 446.1 |
| example 61 | (3R)-3-[6-({2-[(tert-butoxy)carbonyl]-2-azaspiro[3.3]heptan-6-yl}(2-methylpropyl)amino)-5-{[(3-methyl-1,2-oxazol-5-yl)carbamoyl]amino}pyridin-3-yl]butanoic acid | 1.08 | 571.4 | |
| example 62 | (3R)-3-{5-[(6-cyanopyridin-3-yl)amino]-6-[(2-methylpropyl)(oxan-4-yl)amino]pyridin-3-yl}butanoic acid | 0.90 | 438.1 | 436.3 |
| example 63 | (3R)-3-{5-[(5-carbamoyl-1,3,4-thiadiazol-2-yl)amino]-6-[cyclohexyl(2-methylpropyl)amino]pyridin-3-yl}butanoic acid | 0.98 | | 459.3 |
| example 64 | (3R)-3-{6-[cyclohexyl(2-methylpropyl)amino]-5-{[5-(methylcarbamoyl)-1,3,4-thiadiazol-2-yl]amino}pyridin-3-yl}butanoic acid | 1.04 | | 473.3 |
| example 65 | (3R)-3-{5-[(2-cyanopyrimidin-5-yl)amino]-6-[(2-methylpropyl)(oxan-4-yl)amino]pyridin-3-yl}butanoic acid | 0.93 | | 437.4 |
| example 66 | (3R)-3-{6-[(2-methylpropyl)(oxan-4-yl)amino]-5-{[6-(trifluoromethyl)pyridazin-3-yl]amino}pyridin-3-yl}butanoic acid | 0.99 | | 480.3 |
| example 67 | (3R)-3-{5-[(5-cyanopyrazin-2-yl)amino]-6-[(2-methylpropyl)(oxan-4-yl)amino]pyridin-3-yl}butanoic acid | 0.96 | 439.8 | 437.3 |
| example 68 | (3R)-3-{5-[(5,6-dichloropyridin-2-yl)amino]-6-[(2-methylpropyl)(oxan-4-yl)amino]pyridin-3-yl}butanoic acid | 1.20 | 481.3 | |
| example 69 | (3R)-3-{5-[(5-chloro-6-methylpyridin-2-yl)amino]-6-[(2-methylpropyl)(oxan-4-yl)amino]pyridin-3-yl}butanoic acid | 1.16 | 461.3 | |

HPLC retention times and observed mass spec data listed below.

| | | IPQA $T_{elute}$ [min] | M + 1 | M − 1 |
|---|---|---|---|---|
| example 70 | (3R)-3-{5-[(5-chloro-6-cyanopyridin-2-yl)amino]-6-[(2-methylpropyl)(oxan-4-yl)amino]pyridin-3-yl}butanoic acid | 1.08 | 472.3 | |
| example 71 | (3R)-3-{5-[(5-chloropyridin-2-yl)amino]-6-[(2,2-difluoroethyl)(2-methylpropyl)amino]pyridin-3-yl}butanoic acid | 1.21 | 425.3 | |
| example 72 | 3-{6-[bis(2-methylpropyl)amino]-5-{[3-(trifluoromethyl)-1,2,4-thiadiazol-5-yl]amino}pyridazin-3-yl}butanoic acid | 0.95 | 461.6 | |
| example 73 | (3R)-3-{5-[(6-carbamoylpyridazin-3-yl)amino]-6-[(2-methylpropyl)(oxan-4-yl)amino]pyridin-3-yl}butanoic acid | 0.70 | 455.4 | |
| example 74 | (3R)-3-{5-[(6-cyanopyridazin-3-yl)amino]-6-[(2-methylpropyl)(oxan-4-yl)amino]pyridin-3-yl}butanoic acid | 0.86 | 439.5 | 437.3 |
| example 75 | (3R)-3-{5-[(5-chloropyridin-2-yl)amino]-6-[(3,3-difluorocyclobutyl)(2-methylpropyl)amino]pyridin-3-yl}butanoic acid | 1.25 | 453.2 | |
| example 76 | (3R)-3-{5-[(5-chloropyridin-2-yl)amino]-6-[(2-methylpropyl)(3,3,3-trifluoropropyl)amino]pyridin-3-yl}butanoic acid | 1.28 | 457.3 | |
| example 77 | (3R)-3-{5-[(5-chloropyrazin-2-yl)amino]-6-[(2-methylpropyl)(oxan-4-yl)amino]pyridin-3-yl}butanoic acid | 1.02 | 446.2 | |
| example 78 | (3R)-3-{5-[(5-chloropyridin-2-yl)amino]-6-[(2-methylpropyl)(oxan-4-yl)amino]pyridin-3-yl}-N-hydroxybutanamide | 0.89 | 460.3 | |
| example 79 | (3R)-3-{5-[(5-chloropyridin-2-yl)amino]-6-[(2-methylpropyl)(oxan-4-yl)amino]pyridin-3-yl}-N-methanesulfonylbutanamide | 1.06 | 522.3 | |
| example 80 | (3R)-3-{5-[(5-chloropyridin-2-yl)amino]-6-[(2-methylpropyl)(oxan-4-yl)amino]pyridin-3-yl}-N-(dimethylsulfamoyl)butanamide | 1.13 | 551.4 | |
| example 81 | (3R)-3-{5-[(3-chloro-1,2,4-thiadiazol-5-yl)amino]-6-[(3,3-difluorocyclobutyl)(2-methylpropyl)propyamino]pyridin-3-yl}butanoic acid | 1.19 | 460.2 | |
| example 82 | (3R)-3-{4-[(5-chloropyridin-2-yl)amino]-5-[(2-methylpropyl)(oxan-4-yl)amino]pyridin-2-yl}butanoic acid | 0.81 | 447.2 | |
| example 83 | (3R)-3-{6-[(5-aminopentyl)(oxan-4-yl)amino]-5-[(5-chloropyridin-2-yl)amino]pyridin-3-yl}butanoic acid | 0.68 | 476.4 | |
| example 84 | (3R)-3-{5-[(5-chloropyridin-2-yl)amino]-6-{[5-({[(4E)-cyclooct-4-en-1-yloxy]carbonyl}amino)pentyl](oxan-4-yl)amino}pyridin-3-yl}butanoic acid | 1.16 | 628.3 | |

To understand its toxicokinetics and potential effect on hepatic functions, EXAMPLE 6 was orally dosed to Beagle dogs for 7 consecutive days. The detailed study design is presented as follows:

| Category | Item | Description |
|---|---|---|
| Species | Beagle Dog | non-naïve, N = 1 male and N = 1 female, fasted overnight and fed 8 hr post dosing, collecting 8 hr sample before returning food |
| Compound | EXAMPLE 6 | |
| Formulation | PO | 1% methylcellulose (MC) |
| In-life | 20 mg/kg, 10 mL/kg, BID (twice a day) for 7 days | 2/timepiont<br>Sampling plasma for TK: at predose, 0.5, 1, 2, 4, 6, 8, 12 (prior to $2^{nd}$ dosing), 24 hr on Day 1 and 7.<br>Sampling serum for clinical chem:<br>Day −2 and −1: at 0 hr before first meal;<br>Day 1 and 7: at predose, 0.5, 1, 2, 4, 6, 8, 12 hr (prior to $2^{nd}$ dosing);<br>Day 2, 3, 4, 5, 6, 8: at 0 hr prior to the $1^{st}$ dose. |

Results and Conclusions:

EXAMPLE 6 was quantifiable in plasma for up to 24 hours post the start of the oral dose on Days 1 and 7. $T_{max}$ occurred at 0.5 hours post dose on Days 1 and 7. The systemic exposure (i.e. $C_{max}$ and $AUC_{0-12}$ values) was similar on Days 1 and 7 for the male dog. Meanwhile, comparable $C_{max}$ was also observed for the female dog, however, ~3-fold increase in $AUC_{0-12}$ was noticed following 7 day repeat dosing. On Day 7, an average of ~147- and ~34-fold therapeutic coverage in Cmax and AUC, respectively, was achieved for the predicted human efficacious dose (see Table 1).

Figure 2:
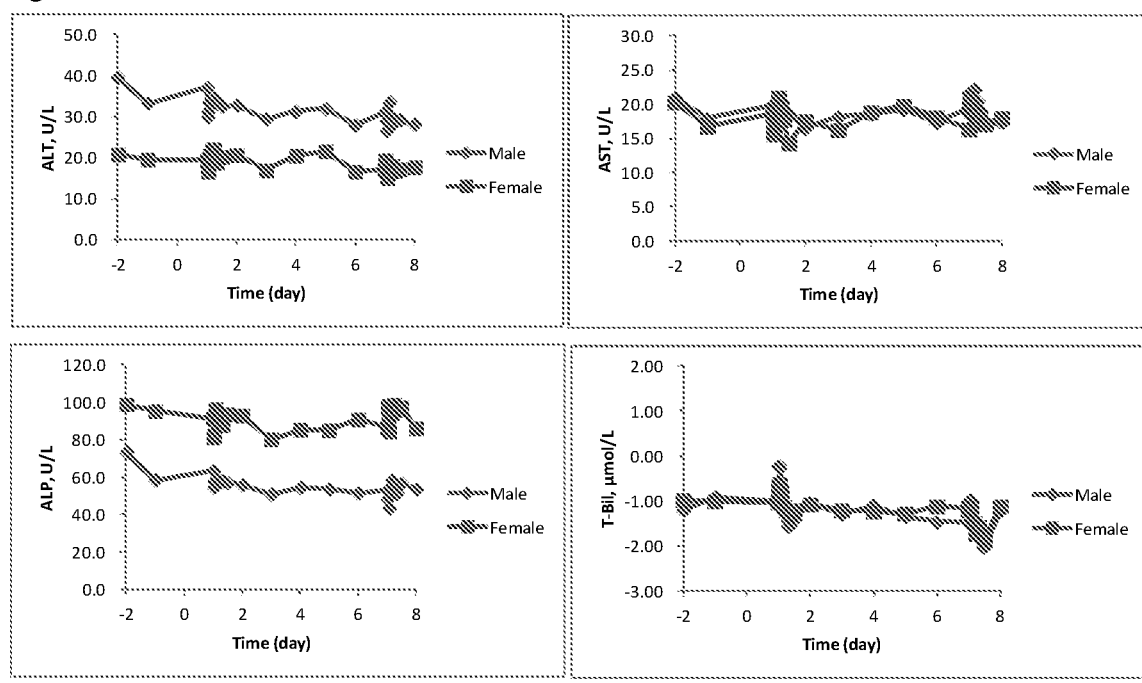
FIG. 2 is daily hepatic enzyme levels of Beagle dogs during the study: ALT (alanine aminotransferase), AST (aspartate aminotransferase), ALP (alkaline phosphatase) and T-Bil (total bilirubin) for example 6, 20 mg/kg PO BID dose.

EXAMPLE 6 was well tolerated throughout the study and no clinical observations were made. Body weights were constant for both male and female dogs over the study as shown in FIG. 1. Hepatic functions measured by serum ALT (alanine aminotransferase), AST (aspartate aminotransferase), ALP (alkaline phosphatase) and T-Bil (total bilirubin) levels were determined to be in the normal variable ranges (see FIG. 2).

APPENDIX

TABLE 1

Summary, of EXAMPLE 6 toxicokinetics in Beagle dogs following 7 day repeat oral administration

| Period | Dose mg/kg | Sex | Subject | $T_{max}$ hr | $C_{max}$ µg/mL | AUC (0-12 hr) µg * hr/mL | Therapeutic Index[1] AUC $C_{max}$ | (0-12 hr) |
|---|---|---|---|---|---|---|---|---|
| Day1 | 20 | Male | 1 | 0.5 | 10.2 | 8.7 | 237 | 25 |
| Day1 | 20 | Female | 1 | 0.5 | 3.7 | 5.2 | 86 | 15 |
| Day7 | 20 | Male | 1 | 0.5 | 8.2 | 6.5 | 191 | 18 |
| Day7 | 20 | Female | 1 | 0.5 | 4.4 | 17.9 | 102 | 51 |

1. Predicted human efficacious exposures: Cmax = 0.043 µg/mL; AUC(0-12) = 0.354 ug*hr/mL

CETSA

Cellular Thermal Shifting assays were used to directly monitor the ligand binding to target proteins in cells. Hela cells were transduced with BacMam virus expressing ePL tagged IDO1 overnight. The cells were then plated over the compounds for 3 hours at 37° C. in cell culture medium containing 1% FBS. The plates were then sealed and heated at 53° C. for 3 min. InCell Hunter reagents were added and luminescence was read in 90 min.

REFERENCES

1. Molina, D. M., et al. Monitoring drug target engagement in cells and tissues using the cellular thermal shift assay. *Science* 2013, 341 (6141), 84-87.
2. Jafari, R., et al. The cellular thermal shift assay for evaluating drug target interactions in cells. *Nature Protocols* 2014, 9 (9), 2100-2122.
3. Jensen, A. J., et al. CETSA: A target engagement assay with potential to transform drug discovery. *Future Medicinal Chemistry* 2015, 7 (8), 975-978.
4. Martinez Molina, D.; Nordlund, P. The Cellular Thermal Shift Assay: A Novel Biophysical Assay for in Situ Drug Target Engagement and Mechanistic Biomarker Studies. In *Annual Review of Pharmacology and Toxicology*, 2016; Vol. 56, pp 141-161.

|  | pXC50_1 | pXC50_2 |
|---|---|---|
| example 3 | 6.79 | 6.73 |
| example 6 | 6.24 | 6.12 |
| example 57 | 5.3 | 5.51 |

IDO1 HeLa RapidFire MS Assay

Compounds of the present invention were tested via high-throughput cellular assays utilizing detection of kynurenine via mass spectrometry and cytotoxicity as endpoints. For the mass spectrometry and cytotoxicity assays, human epithelial HeLa cells (CCL-2; ATCC®, Manassas, Va.) were stimulated with human interferon-γ (IFN-γ) (Sigma-Aldrich Corporation, St. Louis, Mo.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 1 mM or 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ) HeLa cells for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ) HeLa cells for both the mass spectrometry and cytotoxicity assays.

Frozen stocks of HeLa cells were washed and recovered in DMEM high glucose medium with HEPES (Thermo Fisher Scientific, Inc., Waltham, Mass.) supplemented with 10% v/v certified fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 100,000 cells/mL in the supplemented DMEM medium. 50 µL of either the cell suspension, for the mass spectrometry assay, or medium alone, for the cytotoxicity assay, were added to the low control wells, on the previously prepared 384-well compound plates, resulting in 5,000 cells/well or 0 cells/well respectively. IFN-γ was added to the remaining cell suspension at a final concentration of 10 nM, and 50 µL of the stimulated cells were added to all remaining wells on the 384-well compound plates. The plates, with lids, were then placed in a 37° C., 5% CO2 humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 10 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled H$_2$O in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula 100−(100*((U−C2)/(C$_1$−C$_2$))), where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula 100−(100*((U−C2)/(C$_1$−C$_2$))), where U was the unknown value, C1 was the average of the high (0% cytotoxicity) control wells and C2 was the average of the low (100% cytotoxicity) control wells.

Curve fitting was performed with the equation y=A+((B−A)/(1+(10x/10C)D)), where A was the minimum response, B was the maximum response, C was the log(XC50) and D was the Hill slope. The results for each test compound were recorded as pIC50 values for the mass spectrometry assay and as pCC50 values for the cytoxicity assay (−C in the above equation).

IDO1 PBMC RapidFire MS Assay

Compounds of the present invention were tested via high-throughput cellular assays utilizing detection of kynurenine via mass spectrometry and cytotoxicity as endpoints. For the mass spectrometry and cytotoxicity assays, human peripheral blood mononuclear cells (PBMC) (PB003F; AllCells®, Alameda, Calif.) were stimulated with human interferon-γ (IFN-γ) (Sigma-Aldrich Corporation, St. Louis, Mo.) and lipopolysaccharide from *Salmonella minnesota* (LPS) (Invivogen, San Diego, Calif.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 1 mM or 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ/−LPS) PBMCs for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ/+LPS) PBMCs for both the mass spectrometry and cytotoxicity assays.

Frozen stocks of PBMCs were washed and recovered in RPMI 1640 medium (Thermo Fisher Scientific, Inc., Waltham, Mass.) supplemented with 10% v/v heat-inactivated fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 1,000,000 cells/mL in the supplemented RPMI 1640 medium. 50 µL of either the cell suspension, for the mass spectrometry assay, or medium alone, for the cytotoxicity assay, were added to the low control wells, on the previously prepared 384-well compound plates, resulting in 50,000 cells/well or 0 cells/well respectively. IFN-γ and LPS were added to the remaining cell suspension at final concentrations of 100 ng/ml and 50 ng/ml respectively, and 50 µL of the stimulated cells were added to all remaining wells on the 384-well compound plates. The plates, with lids, were then placed in a 37° C., 5% CO2 humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 40 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled H2O in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula 100−(100*((U−C2)/($C_1$−$C_2$))), where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula 100−(100*((U−C2)/($C_1$−$C_2$))), where U was the unknown value, C1 was the average of the high (0% cytotoxicity) control wells and C2 was the average of the low (100% cytotoxicity) control wells.

Curve fitting was performed with the equation y=A+((B−A)/(1+(10x/10C)D)), where A was the minimum response, B was the maximum response, C was the log(XC50) and D was the Hill slope. The results for each test compound were recorded as pIC50 values for the mass spectrometry assay and as pCC50 values for the cytoxicity assay (−C in the above equation).

Potencies of Examples 1 to 84

|  | IDO1 PBMC PXC50 |  | PBMC_TOX PXC50 |  | IDO1 HeLa PXC50 |  | HELA_IDO1_TOX_PXC50 |
|---|---|---|---|---|---|---|---|
| Example 1 | = | 8.4 | < | 5.0 | = | 8 | < | 5 |
| Example 2 | = | 8.4 | < | 5.0 | = | 8 | < | 5 |
| Example 3 | = | 8.9 | < | 5.0 | = | 8 | < | 5 |
| Example 4 | = | 8.4 | < | 5.0 | = | 8 | < | 5 |
| Example 5 | = | 8.1 | < | 5.0 | = | 7.8 | < | 5 |
| Example 6 | = | 8.3 | < | 5.0 | = | 8.1 | < | 5 |
| Example 7 | = | 8.2 | < | 5.0 | = | 7.9 | < | 5 |
| Example 8 | = | 8 | < | 5.0 |  |  |  |  |
| Example 9 | = | 7.7 | < | 5.0 |  |  |  |  |
| Example 10 | = | 8 | < | 5.0 |  |  |  |  |
| Example 11 | = | 9 | < | 5.0 |  |  |  |  |

-continued

| | | IDO1 PBMC PXC50 | | PBMC_TOX PXC50 | | IDO1 HeLa PXC50 | | HELA_IDO1_TOX_PXC50 |
|---|---|---|---|---|---|---|---|---|
| Example 12 | = | 8.6 | < | 5.0 | | | | |
| Example 13 | = | 8.8 | < | 5.0 | | | | |
| Example 14 | = | 8.5 | < | 5.0 | | | | |
| Example 15 | = | 8.3 | < | 5.5 | | | | |
| Example 16 | = | 8.1 | < | 5.2 | | | | |
| Example 17 | = | 8.8 | < | 5.0 | | | | |
| Example 18 | = | 8.4 | < | 5.0 | | | | |
| Example 19 | = | 8.2 | < | 5.0 | | | | |
| Example 20 | = | 8.1 | < | 5.0 | = | 7.9 | < | 5 |
| Example 21 | = | 8.3 | < | 5.0 | | | | |
| Example 22 | = | 8.9 | < | 5.4 | | | | |
| Example 23 | = | 8.4 | < | 5.0 | | | | |
| Example 24 | = | 8.3 | < | 5.0 | | | | |
| Example 25 | = | 8.1 | < | 5.0 | | | | |
| Example 26 | = | 8.5 | < | 5.0 | | | | |
| Example 27 | = | 8.1 | < | 5.0 | | | | |
| Example 28 | = | 8.3 | < | 5.0 | | | | |
| Example 29 | = | 8.3 | < | 5.0 | = | 7.8 | < | 5 |
| Example 30 | = | 8.4 | < | 5.0 | = | 7.4 | < | 5 |
| Example 31 | = | 8.7 | < | 5.0 | = | 8.3 | < | 5 |
| Example 32 | = | 7.7 | < | 5.0 | = | 6.2 | < | 5 |
| Example 33 | = | 8 | < | 5.0 | = | 7.7 | < | 5 |
| Example 34 | = | 7.9 | < | 5.0 | = | 6.5 | < | 5 |
| Example 35 | = | 8.5 | < | 5.0 | = | 8.1 | < | 5 |
| Example 36 | = | 8.2 | < | 5.0 | = | 8.1 | | |
| Example 37 | = | 7.7 | < | 5.0 | | | | |
| Example 38 | = | 7.7 | < | 5.0 | | | | |
| Example 39 | = | 7.9 | < | 5.0 | | | | |
| Example 40 | = | 6.8 | < | 5.6 | = | 8.1 | < | 5 |
| Example 41 | = | 7.7 | < | 5.0 | | | | |
| Example 42 | = | 6.8 | < | 5.0 | | | | |
| Example 43 | = | 5.5 | < | 5.0 | | | | |
| Example 44 | = | 5.2 | < | 5.0 | | | | |
| Example 45 | = | 7.8 | < | 5.0 | | | | |
| Example 46 | = | 7.9 | < | 5.0 | | | | |
| Example 47 | = | 6.6 | < | 5.0 | | | | |
| Example 48 | = | 6.7 | < | 5.0 | | | | |
| Example 49 | = | 6.1 | < | 5.0 | | | | |
| Example 50 | = | 6.8 | < | 5.0 | | | | |
| Example 51 | = | 7.4 | < | 5.0 | | | | |
| Example 52 | = | 7.7 | < | 5.0 | | | | |
| Example 53 | = | 7.4 | < | 5.0 | | | | |
| Example 54 | = | 7.2 | < | 5.0 | | | | |
| Example 55 | = | 5.7 | < | 5.0 | | | | |
| Example 56 | = | 7 | < | 5.0 | | | | |
| Example 57 | = | 7.6 | < | 5.0 | | | | |
| Example 58 | = | 6.7 | < | 5.0 | | | | |
| Example 59 | = | 7.4 | < | 5.0 | | | | |
| Example 60 | = | 7.8 | < | 5.0 | | | | |
| Example 61 | = | 5.7 | < | 5.0 | | | | |
| Example 62 | = | 7.8 | < | 5.0 | | | | |
| Example 63 | = | 7.9 | < | 5.0 | | | | |
| Example 64 | = | 7.6 | < | 5.0 | | | | |
| Example 65 | = | 7.6 | < | 5.0 | | | | |
| Example 66 | = | 7.9 | < | 5.0 | | | | |
| Example 67 | = | 7.2 | < | 5.0 | | | | |
| Example 68 | = | 7.5 | < | 5.0 | | | | |
| Example 69 | = | 6.6 | < | 5.0 | | | | |
| Example 70 | = | 6.8 | < | 5.0 | | | | |
| Example 71 | = | 7.7 | < | 5.0 | | | | |
| Example 72 | < | 5 | < | 5.0 | | | | |
| Example 73 | = | 5 | < | 5.0 | | | | |
| Example 74 | = | 6.9 | < | 5.0 | | | | |
| Example 75 | = | 7.4 | < | 5.0 | | | | |
| Example 76 | = | 7.2 | < | 5.0 | | | | |
| Example 77 | = | 7.7 | < | 5.0 | | | | |
| Example 78 | = | 6.8 | < | 5.0 | | | | |
| Example 79 | = | 7.6 | < | 5.0 | | | | |
| Example 80 | = | 7.9 | < | 5.0 | | | | |
| Example 81 | = | 7.7 | < | 5.0 | | | | |
| Example 82 | = | 8.1 | < | 5.0 | | | | |
| Example 83 | < | 5 | < | 5.0 | = | 8 | < | 5 |
| Example 84 | = | 6.9 | < | 5.0 | = | 8 | < | 5 |

What is claimed is:
1. The compound
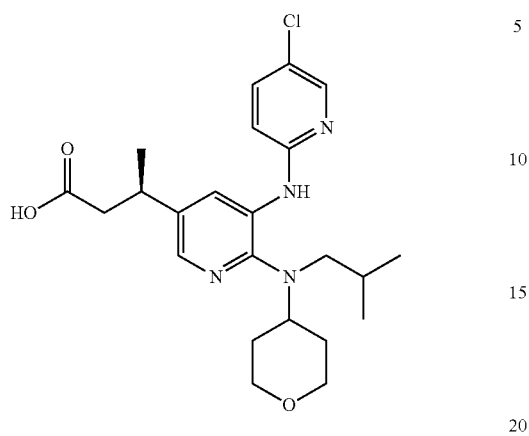
or a pharmaceutically acceptable salt thereof.
2. A pharmaceutical composition comprising a compound or salt according to claim 1.
* * * * *